(12) United States Patent
Zhang

(10) Patent No.: US 6,399,787 B1
(45) Date of Patent: Jun. 4, 2002

(54) CATALYTIC ASYMMETRIC HYDROGENATION, HYDROFORMYLATION, AND HYDROVINYLATION VIA TRANSITION METAL CATALYSTS WITH PHOSPHINES AND PHOSPHITES

(75) Inventor: Xumu Zhang, State College, PA (US)

(73) Assignee: Penn State Research Foundation, University Park, PA (US)

( * ) Notice: Subject to any disclaimer, the term of this patent is extended or adjusted under 35 U.S.C. 154(b) by 0 days.

(21) Appl. No.: 09/685,028

(22) Filed: Oct. 10, 2000

Related U.S. Application Data

(60) Division of application No. 09/313,665, filed on May 18, 1999, now abandoned, which is a continuation-in-part of application No. 08/876,120, filed on Jun. 13, 1997, now Pat. No. 6,037,500.
(60) Provisional application No. 60/085,786, filed on May 18, 1998, and provisional application No. 60/090,164, filed on Jun. 22, 1998.

(51) Int. Cl.⁷ ............................................. C07D 209/04
(52) U.S. Cl. ..................... 548/469; 546/184; 564/149; 562/450; 562/512; 568/715; 568/814
(58) Field of Search ............................... 564/215, 149; 562/400, 8, 512; 548/452, 469, 470; 546/184; 568/814, 715

(56) References Cited

U.S. PATENT DOCUMENTS

| | | |
|---|---|---|
| 3,105,096 A | 9/1963 | Welcher |
| 3,400,163 A | 9/1968 | Mason et al. |
| 3,896,047 A | 7/1975 | Aycock et al. |
| 5,004,845 A | 4/1991 | Bradley et al. |
| 5,008,457 A | 4/1991 | Burk |
| 5,171,892 A | 12/1992 | Burk |
| 5,177,230 A | 1/1993 | Burk |
| 5,258,553 A | 11/1993 | Burk |
| 5,426,223 A | 6/1995 | Burk |
| 5,491,266 A | 2/1996 | Babin et al. |
| 5,596,114 A | 1/1997 | Burk |
| 5,936,127 A | 8/1999 | Zhang |
| 6,037,500 A | 3/2000 | Zhang |

FOREIGN PATENT DOCUMENTS

| | | |
|---|---|---|
| WO | WO 95/05354 | 2/1995 |
| WO | WO 95/06025 | 3/1995 |
| WO | WO 97/13763 | 4/1997 |
| WO | WO 97/47633 | 12/1997 |
| WO | WO 99/24443 | 5/1999 |

OTHER PUBLICATIONS

CA:85:63122 abs of J Organomet. Chem by Hayashi et al 113(2) pp127–37 1976.*
CA:95:186518 abs of Kreuzfeld et al React. Kinet. Catal. Lett. 16(2–3), pp 229–32 1981.*
CA:90:204443 abs of Tetrahedron by Glaser et al 34(15) pp 2405–8 1978.*
CA:101: 37807 abs of Bull. Chem. Soc. Jpn by Yatagai et al 57(3) pp 739–46 1984.*
CA:126:343683 abs of WO9713763 Apr. 1997.*
CA:127:50726 abs of J. Org. Chem by Chen et al 62(13) pp 4521–4523 1997.*
CA:126:305335 abs of J. Am. Chem. Soc. by Zhu et al 119(16) pp 3836–3837 1997.*
CA:126:8188 abs of Tetrahedron Lett. by Hamada et al 37(42) pp 7565–7568 1996.*
CA:124:56975 abs of WO9515938 Jun. 1995.*
Achiwa, K., "Asymmetric Hydrogenation with New Chiral Functionalized Bisphosphine–Rhodium Complexes," J. Am. Chem. Soc., vol. 98, No. 25, pp. 8265–8266 (1976).
Ager, D.J., et al., "The Synthesis of Carbohydrate Derivatives from Acyclic Precursors," Tetrahedron, vol. 49, No. 26, pp. 5683–5765 (1993).
Arco, M.J., et al., "Synthesis of (±)–Nonactic Acid," J. Org. Chem., vol. 41, No. 12, pp. 2075–2083 (1976).
Brown, J.M., et al., "The Mechanism of Asymmetric Hydrogenation," J. Chem. Soc., Perkin Transactions II, No. 4, pp. 489–497 (1982).
Brown, H.C., et al., "Hydroboration," J. Org. Chem., vol. 47, pp. 5074–5083 (1982).
Brunner, H., "Enantioselective Synthesis with Optically Active Transition–Metal Catalysts," J. Heterocyclic Chem., Reviews, pp. 645–654 (Sep. 1988).
Burk, M.J., et al., "A Convenient Asymmetric Synthesis of α–1–Arylalkylamines through the Enantioselective Hydrogenation of Enamides," J. Am. Chem. Soc., vol. 118, pp. 5142–5143 (1996).
Burk, M.J., et al., "Highly Regio– and Enantioselective Catalytic Hydrogenation . . . ," J. Am. Chem. Soc., No. 120, pp. 657–663 (1998).
Burk, M.J., et al., "Highly Enantioselective Hydrogenation of β–Keto Esters Under Mild Conditions," J. Am. Chem. Soc., vol. 117, pp. 4423–4424 (1995).
Burk, M.J., et al., "Preparation and Use of $C_2$–Symmetric Bis(phospholanes): Production of α–Amino Acid Derivatives via Highly Enantioselective Hydrogenation Reactions," J. Am. Chem. Soc., vol. 115, pp. 10125–10138 (1993).
Burk, M.J., "$C_2$–Symmetric Bis(phospholanes) and Their Use in Highly Enantioselective Hydrogenation Reactions," J. Am. Chem. Soc., vol. 113, pp. 8518–8519 (1991).

(List continued on next page.)

Primary Examiner—Jean F. Vollano
(74) Attorney, Agent, or Firm—Finnegan, Henderson, Farabow, Garrett & Dunner, L.L.P.

(57) ABSTRACT

Novel transition metal catalysts with conformationally rigid chiral phosphines and phosphites are developed for asymmetric carbon-hydrogen and carbon—carbon bond formation. The invention emphasizes synthesis of chiral amines, β-amino acids and related compounds via catalytic asymmetric hydrogenation based on chiral monodentate and bidentate phosphines with cyclic ring structures. The ligands contain rigid ring structures.

17 Claims, 2 Drawing Sheets

OTHER PUBLICATIONS

Burk, M.J., et al., "New Electron–Rich Chiral Phosphines for Asymmetric Catalysis," Organometallics, vol. 9, pp. 2653–2655 (1990).

Cannarsa, M.J., "Single enantiomer drugs: new strategies and directions," Chem & Ind., vol. 10, pp. 374–378 (1996).

Chan, A.S., et al., "Novel Spiro Phosphinite Ligands and Their Application in Homogeneous Catalytic Hydrogenation Reactions," J. Am. Chem. Soc., vol. 119, pp. 9570–9571 (1997).

Chen, Z., et al., "Asymmetric Synthesis and Metalation of $C_2$–Symmetric Annulated Bicyclooctylcyclopentadienes," Organometallics, vol. 10, pp. 3449–3458 (1991).

Chen, Z., et al., "Syntheses of Novel Chiral Monophosphines, 2,5–Dialkyl–7–phenyl–7–phosphabicyclo[2.2.1] heptanes, and Their Application in Highly Enantioselective Pd–Catalyzed Allylic Alkylations," J. Org. Chem., vol. 62, pp. 4521–4523 (1997).

Consiglio, G., et al., "Enantioselective Homogeneous Catalysis Involving Transition–Metal–Allyl Intermediates," Chem. Rev., vol. 89, pp. 257–276 (1989).

Corey, E.J., et al., "New Reagants for the Intermolecular and Intramolecular Pinacolic Coupling of Ketones and Aldehydes," J. Org. Chem., vol. 41, No. 2, pp. 260–265 (1976).

Czarnocki, Z., et al., "Diastereoselective Reduction of Derivatives of 3,4–dihydro–1–methylidene–2–tartaroylisoquinoline," Heterocycles, vol. 34, No. 5, pp. 943–953 (1992).

Fryzuk, M.D., et al., "Asymmetric Synthesis. Production of Optically Active Amino Acids by Catalytic Hydrogenation," J. Am. Chem. Soc., vol. 99, No. 19, pp. 6262–6267 (1977).

Fryzuk, M.D., et al., "Asymmetric Synthesis," J. Am. Chem. Soc., vol. 100, No. 17, pp. 5491–5494 (1978).

Genet, J.P., et al., "Novel, General Synthesis of the Chiral Catalysts . . . ,"Tetrahedron, vol. 5, No. 4, pp. 665–674 (1994).

Greidinger, D.S., et al., "Alicyclic Studies," J. Org. Chem., vol. 22, pp. 1408–1410 (1957).

Halterman, R.L., et al., "A Designed, Enantiomerically Pure, Fused Cyclopentadienyl Ligand with $C_2$ Symmetry: Synthesis and Use in Enantioselective Titanocene–Catalyzed Hydrogenations of Alkenes," J. Am. Chem. Soc., vol. 109, pp. 8105–8107 (1987).

Hamada, Y., et al., "New Monodentate Chiral Phosphine . . . ,"Tetrahedron Letters, vol. 37, No. 42, pp. 7565–7568 (1996).

Hayashi, T., et al., "Catalytic asymmetric synthesis of optically active alcohols via hydrosilation of olefins with a chiral monophosphine–palladium catalysts,"Pure & Appl. Chem., vol. 64, No. 12, pp. 1911–1916 (1992).

Hayashi, T., et al., "Asymmetric Synthesis Catalyzed by Transition–Metal Complexes with Functionalized Chiral Ferrocenylphosphine Ligands,"Acc. Chem. Res., vol. 15, pp. 395–401 (1982).

Hayashi, T., "MOP: A Monodentate Chiral Phoshine Ligand for Catalytic Asymmetric Reactions," J. Synth. Org. Chem., Jpn., vol. 52, No. 11, pp. 900–911 (1994).

Hayashi, T., et al., Fundamental Research in Homogeneous Catalysis (Ishii, Y., et al., Eds.) vol. 2, p. 159 (Plenum, 1978).

Hughes, L., "The Mitsunobu Reaction,"Organic Reactions, vol. 42, pp. 387–388 (1992).

Ito, Y., et al., "Catalytic Asymmetric Aldol Reaction," J. Am. Chem. Soc., vol. 108, pp. 6405–6406 (1986).

Jacobsen, E.N., "Asymmetric Catalytic Epoxidation of Unfunctionalized Olefins,"Catalytic Asymmetric Synthesis, Ch. 4.2, pp. 159–202 (1993).

Jiang, Q., et al., "Highly Enantioselective Hydrogenation of Simple Ketones Catalyzed by a Rh–PennPhos Complex, "Angew. Chem. Int. Ed., vol. 37, No. 8, pp. 1100–1103 (1998).

Kagan, H.B., et al., "Asymmetric Catalytic Reduction with Transition Metal Complexes," J. Am. Chem. Soc., vol. 94, No. 18, pp. 6429–6433 (1972).

Kagan, H.B., et al., "Reduction Asymetrique Catalysee Par Des Complexes De Metaux De Transition,"J. Organomet. Chem., vol. 90, pp. 353–365 (1975).

Kitamura M., et al., "General Asymmetric Synthesis of Isoquinoline Alkaloids,"J. Org. Chem., vol. 59, pp. 297–310 (1994).

Kitamura, M., et al., "Conformational Study on 2–Acyl–1–alkylidene–1,2,3,4–tetrahydroisoquinolines, "Bull. Chem. Soc. Jpn., vol. 69, No. 6, pp. 1695–1700 (1996).

Knowles, W.S., "Asymmetric Hydrogenation,"Acc. Chem. Res., vol. 16, pp. 106–112 (1983).

Knowles, W.S., et al., "Catalytic Asymmetric Hydrogenation,"J.C.S., Chem. Comm., pp. 10–11 (1972).

Koenig, K.E., et al., "Asymmetric Hydrogenation of Geminal–Substituted Vinyl Acetates," J. Org. Chem., vol. 45, pp. 2362–2365 (1980).

Kohmura, Y., et al., "Benzylic and Allylic Amination,"Synlett, Letters, No. 12, pp. 1456–1458 (1997).

Lee, N.E., et al., "Asymmetric Hydrogenation of Enamines with a Chiral Titanocene Catalyst,"J. Am. Chem. Soc., vol. 116, pp. 5985–5986 (1994).

Lenz, G.R., "The Photochemistry of Enamides,"Synthesis, pp. 489–518 (1978).

MacNeil, P.A., et al., "Asymmetric Synthesis. Asymmetric Catalytic Hydrogenation Using Chiral Chelating Six–Membered Ring Diphosphines,"J. Am. Chem. Soc., vol. 103, pp. 2273–2280 (1981).

Miyashita, A., et al., "2,2 –Bis(diphenylphosphine)–1–1'–binaphthyl (BINAP),"Tetrahedron, vol. 40, No. 8, pp. 1245–1253 (1984).

Miyashita, A., et al., "Synthesis of 2,2'–bis(diphenylphosphino)–1,1'–binaphthyl (BINAP), an Atropisomeric Chiral Bis(triaryl)phosphine, and Its Use in the Rhodium(I)–Catalyzed Asymmetric Hydrogenation of α–(Acylamino)acrylic Acids,"J. Am. Chem. Soc., vol. 102, pp. 7932–7934 (1980).

Morimoto, T., et al., "An Improved Diphosphine–Iridium(I) Catalyst System for the Asymmetric Hydrogenation of Cyclic Imines . . . ,"Tetrahedron: Asymmetry, vol. 6, No. 11, pp. 2661–2664 (1995).

Morimoto, T., et al., "Effects of the Diarylphosphino Groups of Modified DIOPS on the Enantioselectivity and the Catalytic Activity of their Rhodium(I) Complexes . . . ,"Chem. Pharm. Bull, vol. 40, No. 10, pp. 2894–2896 (1992).

Morimoto, T., et al., "Synthesis of a New Chiral Bisphosphine Ligand . . . ,"Tetrahedron: Asymmetry, vol. 6, No. 1, pp. 75–78 (1995).

Munchhof, M.J., et al., "A Novel Route to Chiral, Nonracemic 1–Alkyl– and 1–Aryl– Substituted Tetrahydroisoquinolines,"J. Org. Chem., vol. 60, pp. 7086–7087 (1995).

Nagel, U., et al., "Synthese N–substituierter (R,R)–3,4–Bis–(dyphenylphosphino) . . . ," Chem. Ber., vol. 119, pp. 3326–3343 (1986).

Nagel, U., et al., CA105:209056 (abstract of Chem. Ber. (1986) document).

Noyori, R., et al., "BINAP: An Efficient Chiral Element for Asymmetric Catalysts," Acc. Chem. Res., vol. 23, pp. 345–350 (1990).

Noyori, R., et al., "Stereoselective Hydrogenation via Dynamic Kinetic Resolution,"J. Am. Chem. Soc., vol. 111, pp. 9134–9135 (1989).

Noyori, R., "Chiral Metal Complexes as Discriminating Molecular Catalysts,"Science, vol. 248, pp. 1194–1199 (1990).

Noyori, R., et al., "Asymmetric Synthesis of Isoquinoline Alkaloids by Homogeneous Catalysis,"J. Am. Chem. Soc., vol. 108, pp. 7117–7119 (1986).

Nozaki, K., et al., "Highly Enantioselective Alternating Copolymerization of Propene with Carbon Monoxide Catalyzed by a Chiral Phosphine–Phosphite Complex of Palladium (II)," J. Am. Chem. Soc., vol. 117, pp. 9911–9912 (1995).

Nozaki, K., et al., "Highly Enantioselective Hydroformylation of Olefins Catalyzed by Rhodium(I) Complexes,"J. Am. Chem. Soc., vol. 119, pp. 4413–4423 (1997).

Nugent, W.A., et al., "Beyond Nature's Chiral Pool: Enantioselective Catalysis in Industry,"Science, vol. 259, pp. 479–483 (1993).

Ojima, I., et al., "N–Carbamoyl–4–diphenyl-phosphino–2–diphenylphospinomethylpyrrolidines (CAPP). Efficient New Chiral Ligands for Asymmetric Hydrogenation,"Tetrahedron Letters, vol. 21, pp. 1051–1054 (1980).

Okada, Y., et al, "The First Synthesis of Chiral Phosphinocarboxylic Acid Ligands, Trans–2–(dyphenylphosphino)cycloalkanecarboxylic Acids," Tetrahedron Letters, vol. 31, No. 27, pp. 3905–3908 (1990).

Pfaltz, A., "Chiral Semicorrins and Related Nitrogen Heterocycles as Ligands in Asymmetric Catalysts,"Acc. Chem. Res., vol. 26, pp. 339–345 (1993).

Reddy, K.L., et al., "From Styrenes to Enatiopure α–Arylglycines in Two Steps,"J. Am. Chem. Soc., vol. 120, pp. 1207–1217 (1998).

Sakai, N., et al., "Highly Enantioselective Hydroformylation of Olefins Catalyzed by New Phosphinephosphite–Rh(I) Complexes,"J. Am. Chem. Soc., vol. 115, pp. 7033–7034 (1993).

Sawamura, M., et al., "An Enantioselective Two–Component Catalyst System,"J. Am. Chem. Soc., vol. 118, pp. 3309–3310 (1996).

Sawamura, M., et al., "Trans–Chelating Chiral Diphosphane Ligands Bearing Flexible P–Alkyl Substituents...,"Angew. Chem. Int. Ed. Engl., vol. 33, No. 1, pp. 111–113 (1994).

Selke, R., et al., "Phosphinites of Carbohydrates as Chiral Ligands for Asymmetric Synthesis Catalyzed by Complexes,"J. of Mol. Cat., vol. 37, pp. 213–225 (1986).

Sinou, D., et al., "Catalyse Asymetrique par le Complexe Cationique,"J. Organomet. Chem., vol. 114, pp. 325–337 (1976).

Spindler, F., et al., "A Technically Useful Catalyst for the Homogeneous Enantioselective Hydrogenation of N–Aryl Imines: A Case Study,"(Proceedings of the Conference on) Catalysis of Organic Reactions, Paper No. 63, pp. 153–166 (1996).

Sutton, B.M., et al., "An Alternative Synthesis, X–Ray Crystal Structure and P388 Activity of 1,2–Bis(dibenzophospholyl–1)ethane [1],"J. Heterocyclic Chem., vol. 27, No. 4, pp. 1123–1126 (1990).

Takaya, H., et al., "Synthesis of Biaryls via Palladium–Catalyzed Cross Coupling...,"Org. Synth., vol. 66, pp. 67–74 (1988).

Takaya, H., et al., "Practical Synthesis of (R)– or (S)–2,2'–Bis(diarylphosphino)–1,1 binaphthyls (BINAPs),"J. Org. Chem., vol. 51, pp. 629–635 (1986).

Takaya, H., et al., "(R)–(+)– and (S)–(–)–2,2 –BINAP,"Org. Syntheses, pp. 57–63 (1989).

Takaya, H., et al., "Asymmetric Hydrogenation,"Catalytic Asymmetric Synthesis, Ch. 1, pp. 1–39 (1993).

Togni, A., "Planar–Chiral Ferrocenes: Synthetic Methods and Applications," Angew. Chem. Int. Ed. Engl., vol. 35, No. 13/14, pp. 1475–1477 (1996).

Trost, B.M., et al., "Asymmetric Transition Metal–Catalyzed Allylic Alkylations,"Chem. Rev., vol. 96, pp. 395–422 (1996).

Tschaen, D.M., et al., "Asymmetric Synthesis of MK–0499,"J. Org. Chem., vol. 60, pp. 4324–4330 (1995).

Uozumi, Y., et al., "Catalytic Asymmetric Synthesis of Optically Active 2–Alkanols...,"J. Am. Chem. Soc., vol. 113, pp. 9887–9888 (1991).

Vineyard, B.D., et al., "Asymmetric Hydrogenation. Rhodium Chiral Bisphosphine Catalyst,"J. Am. Chem. Soc., vol. 99, No. 18, pp. 5946–5952 (1977).

Zhang, X., et al., "Asymmetric Hydrogenation of Cycloalkanones Catalyzed by BINAP–Ir(I)–Aminophosphine Systems,"J. Am. Chem. Soc., vol. 115, pp. 3318–3319 (1993).

Zhu, G., et al., "Highly Enantioselective Rhodium–Catalyzed Hydrogenation of Dehydroamino Acids with New Chiral Bisphosphinites,"J. Org. Chem., vol. 63, pp. 3133–3136 (1998).

Zhu, G., et al., "Asymmetric [3+2] Cycloaddition of 2,3–Butadienoates with Electron–Deficient Olefins...,"J. Am. Chem. Soc., vol. 119, pp. 3836–3837 (1997).

Zhu, G., et al., "Highly Enantioselective Rh–Catalyzed Hydrogenations wtih a New Chiral 1,4–Bisphosphine...,"J. Am. Chem. Soc., vol. 119, pp. 1799–1800 (1997).

Bosnich, B., Ed., *Asymmetric Catalysis* (Martinus Nijhoff, 1986).

Koenig, K.E., *Asymmetric Synthesis*, vol. 5, Ch. 3 (Academic Press, 1985).

Noyori, R., *Modern Synthetic Methods*, vol. 5, p. 115 (Scheffold, R., Ed., Springer–Verlag; Berlin Heidelberg, 1989).

Noyori, R., *Asymmetric Catalysts in Organic Synthesis* (John Wiley & Sons, Inc., 1994).

Ojima, I., Ed., *Catalytic Asymmetric Synthesis* (VCH, 1993).

Zhu et al., *J. Amer. Chem. Soc.* 119 (7) pp. 1799–1800, abstract, (1997).

Hamada et al., *Tetrahedron Lett*, 37 (42) pp. 7565–7568, abstract (1996).

* cited by examiner

CATALYTIC ASYMMETRIC HYDROGENATION, HYDROFORMYLATION, AND HYDROVINYLATION VIA TRANSITION METAL CATALYSTS WITH PHOSPHINES AND PHOSPHITES

This is a division of application Ser. No. 09/313,665 filed on May 18, 1999, abandoned, which is a continuation-in-part of application Ser. No. 09/313,655 filed May 18, 1999, now U.S. Pat. No. 6,192,995, which is a continuation-in-part of application Ser. No. 08/876,120 filed on Jun. 13, 1997, now U.S. Pat. No. 6,037,500, and claims priority to U.S. Provisional Application Nos. 60/090,164 and 60/085,786 filed on May 18, 1998, filed on Jun. 22, 1998. All prior applications are herein incorporated by reference.

BACKGROUND OF THE INVENTION

1. Field of the Invention

The present invention relates to chiral phosphine ligands for asymmetric catalysis.

2. Description of Related Arts

Molecular chirality plays a very important role in science and technology. The biological activities of many pharmaceuticals, fragrances, food additives and agrochemicals are often associated with their absolute molecular configuration. While one enantiomer gives a desired biological function through interactions with natural binding sites, another enantiomer usually does not have the same function and sometime has deleterious side effects.

The sale of enantiomerically pure pharmaceuticals was about $61 billion in 1995, about 26 percent of the $240 billion total market for final formulation pharmaceuticals (Cannaesa, M. S. Symposium, Chiral '97, Matrix, 1997; Cannarsa, M. J. Chemistry & Industry, 1996, May 20, page 374). There is a growing demand in the pharmaceutical and fine chemicals industries to develop cost-effective processes for the manufacture of single-enantiomeric products.

To meet this fascinating challenge, chemists have explored many approaches for acquiring enantiomerically pure compounds ranging from optical resolution and structural modification of naturally occurring chiral substances to asymmetric catalysis using synthetic chiral catalysts and enzymes. Among these methods, asymmetric catalysis is perhaps the most efficient because a small amount of a chiral catalyst can be used to produce a large quantity of a chiral target molecule. During the last two decades, great attention has been devoted to discovering new asymmetric catalysts and many commercial industrial processes have used asymmetric catalysis as the key step in the production of enantiomerically pure compounds. See (a) Morrison, J. D., Ed. Asymmetric Synthesis Academic Press: New York, 1985, Vol. 5; (b) Bosnich, B., Ed. Asymmetric Catalysis Martinus Nijhoff Publishers: Dordrecht, The Netherlands, 1986; (c) Brunner, H. Synthesis 1988, 645; (d) Noyori, R.; Kitamura, M. In Modern Synthetic Methods; Scheffold, R., Ed.; Springer-Verlag: Berlin Hedelberg, 1989, Vol. 5, p 115: (f) Nugent, W. A., RajanBabu, T. V., Burk, M. J. Science 1993, 259, 479; (g) Ojima, I., Ed. Catalytic Asymmetric Synthesis, VCH: New York, 1993; and (h) Noyori, R. Asymmetric Catalysis In Organic Synthesis, John Wiley & Sons, Inc: New York, 1994.

In order to develop efficient synthetic methods that have a real impact in the pharmaceutical industry, it is useful to categorize the chiral building blocks according to their functionality and analyze what is needed in each area. A recent survey by Technology Catalysts International shows that amino acid derivatives, chiral amines, and chiral alcohols comprise over 40 percent of developmental enantiomerically pure pharmaceuticals. Asymmetric hydrogenation plays a dominant role in the manufacture of enantiomerically pure compounds. Major pharmaceutical and fine chemical companies have devoted significant effort in developing and commercializing asymmetric hydrogenation technology. The key element of the research is developing chiral phosphine ligands to increase reaction selectivity and activity.

In fact, asymmetric hydrogenation accounts for major part of all asymmetric synthesis on a commercial scale. Many important advances have been achieved based on the discovery of structurally different chiral phosphine motifs. Some dramatic examples of industrial applications of asymmetric synthesis include Monsanto's L-DOPA synthesis (asymmetric hydrogenation of a dehydroamino acid, 94% ee, 20,000 turnovers with a Rh-DIPAMP complex) (Knowles, W. S., Acc. Chem. Res. 1983, 16, 106), Takasago's L-menthol synthesis (asymmetric isomerization, 98% ee, 300,000 turnovers with a Rh-BINAP complex) (Noyori, R. Science 1990, 248, 1194; Noyori, R. et al., Acc. Chem. Res. 1990, 23, 345) and Ciba-Geigy's (S)-Metolachlor synthesis (asymmetric hydrogenation of an imine, 80% ee, 1,000,000 turnovers with an Ir-ferrocenyl phosphine complex) (see Proceeding of the Conference on Catalysis of Organic Reactions, Spindler, F., et al., Altanta, 1996; Chem. Ind. (Dekker), 1996, 63; Tongni, A. Angew. Chem. lnt. Ed. Engl. 1996, 356, 14575).

Chiral ligands for transition metal-catalyzed reactions play a critical role in asymmetric catalysis. Not only the enantioselectivity depends on the framework of chiral ligands; reactivities can often be altered by changing the steric and electronic structure of the ligands. Since small changes in the ligand can influence the (delta)(delta)G of the rate determining step, it is very hard to predict which ligand can be effective for any particular reaction or substrate. The majority of breakthroughs in asymmetric catalysis have come from the empirical match of the right ligands with the right transition metals. Perusal of the literature shows that over 100 chiral phosphines were investigated to discover the original L-Dopa asymmetric hydrogenation catalyst.

While ideas based on conformational analysis or steric and electronic properties are useful for ligand design and for generating working hypotheses, overemphasis on these ideas can potentially misguide and hinder the development of truly efficient ligands. Creation of a new ligand motif and fine-tuning (trouble-shooting) established chiral ligand systems are equally important in asymmetric catalysis. For example, many chiral diphosphines have similar chemical structures (e.g., chelating bis-diphenyl phosphine with chiral backbones), yet most of these ligands have different profiles in terms of enantioselectivity and activity for transition metal-catalyzed reactions. Understanding of the subtle changes which makes a particular ligand more effective for a certain reaction than another similar ligand is the intellectual frontier of current study in asymmetric catalysis. In the process of creating low molecular weight catalysts with enzymatic properties, the invention of effective chiral ligands is analogous to generating new enzyme frameworks.

The development of chiral phosphines has had a profound impact in the field of asymmetric catalysis. FIG. 1 shows several important chiral phosphines studied during the last three decades. Knowles' DIPAMP (Knowles, W. S. et al., J. Chem. Soc., Chem. Commun. 1972, 10; Vineyard, B. D. et al., J. Am. Chem. Soc. 1977, 99, 5946) and Kagan's Diop (Kagan, H. B.; Dang, T.-P. J. Am. Chem. Soc. 1972, 94, 6429) ligands were reported for Rh (I) catalyzed asymmetric hydrogenation at about the same time. The great success in asymmetric hydrogenation of a-acylaminoacrylic acids stimulated continuing research on new chiral phosphine ligands.

Various bidentate chiral diphosphines such as Chiraphos (Fryzuk, M. D. et al., J. Am. Chem. Soc. 1977, 99, 6262), BPPM (Achiwa, K. J. Am. Chem. Soc. 1976, 98, 8265; Ojima, I., Tetrahedron Lett. 1980, 21, 1051), DegPhos (Nagel, U., et al., Chem. Ber. 1986, 119, 3326) and ferrocenyl chiral phosphines (Hayashi, T. et al., Fundamental Research in Homogeneous Catalysis, Ishii, Y. et al., (Eds.) Plenum: New York, 1978; Vol. 2, p 159; Hayashi, T., et al., Acc.. Chem. Res. 1982, 15, 395; Ito, Y., et al., Am. Chem. Soc. 1986, 108, 6405) were discovered in both academic labs and in industry. Two benchmark ligands come out of extensive ligand studies: BINAP (Miyashita, A., et al., J. Am. Chem. Soc. 1980, 102, 7932; Miyashita, A., et al., Tetrahedron 1984, 40, 1245; Takaya, H., et al., J. Org. Chem. 1986, 51, 629; Takaya, H., et al., Org. Synth. 1988, 67, 20) in the early 80's is one of the most frequently used bidentate chiral phosphines, and DuPhos (Burk, M. J., et al., Organometallics 1990, 9, 2653; Burk, M. J. J. Am. Chem. Soc. 1991, 113, 8518; Burk, M. J., et al., J. Am. Chem. Soc. 993, 115, 10125) in the early 90's has also shown impressive enantioselectivities.

The Rh, Ru and Ir complexes of these ligands have been used as catalysts for asymmetric hydrogenation of olefins, ketones and imines. These ligands are also useful for other asymmetric reactions such as isomerization, hydroacylation, Heck reaction, and Grignard coupling. However, there are still a variety of reactions in which only modest enantioselectivity has been achieved with these ligands, and substrate scope is limited both for hydrogenation and for other reactions. Complementary classes of chiral ligands are needed.

Due to the critical role of chiral ligands in reaction activity and selectivity, many new phosphine ligands were invented in the 90's. The major feature of the new chiral phosphine ligands is their structural diversity where different structural motif is created, ligand complexity increases, and the steric and electronic properties of ligands are more tunable. Some of these ligands include monodentate chiral phosphines (MOP) (Hayashi, T. J. Syhth. Org. Chem., Jpn. 1994, 901; Uozumi, Y. et al., J. Am. Chem. Soc. 1991, 113, 9887; Hayashi, T., et al., Pure & Appl. Chem. 1992, 64, 1911), ferrocenyl phosphine bearing two different phosphine groups (Togni, supra), Trost's chiral bisphosphines (Trost, B. M., et al., Chem. Rev. 199 , 96, 395), mixed N-P ligands (Pfaltz, A. Acc. Chem. Res. 1993, 26, 339 and Helmchen), Trans diphosphines (TRAP) (Sawamura, M., et al., J. Am. Chem. Soc. 1996, 118, 3309; Sawamura, M., et al., Angew. Chem. Int. Ed.Engl. 1994, 33, 111) and phosphine-phosphite ligand (BINAPHOS) (Nozaki, K., et al., J. Am. Chem. Soc. 1995, 117, 9911; Sakai, N., et al., J. Am. Chem. Soc. 1993, 115, 7033). These new ligands are effective for several asymmetric reactions: hydrosilylation, hydrogenation of imines, allylic alkylation, Michael addition and hydroformylation. It is important to note that many basic catalytic reactions have been discovered and extensively studied for all these important asymmetric reactions. Even with a good understanding of the basic reaction mechanism, discovering effective chiral phosphine ligands for transition metal-catalyzed reactions is still a tremendous challenge.

The development of chiral ligands to control catalytic activity and enantioselectivity remains as one of the most exciting and challenging subjects in research on catalytic asymmetric synthesis. Most chiral phosphines prepared so far are bisphosphines. The bidentate chelation of the ligand is effective for many asymmetric reactions. On the other hand, only a limited number of monodentate chiral phosphines have been prepared and studied. The general view is that monodentate chiral phosphines have little practical utility. However, there are many transition metal-catalyzed reactions where metal complexes with bisphosphines are not effective because of low activity and selectivity and therefore chiral monophosphines are required. This situation is particularly true for certain Ni and Pd-catalyzed reactions. So far, the most well-studied monodentate phosphines are Hayashi's MOP, 2-(diphenylphosphino)-2'-methoxy-1,1'-binaphthyl and its analogs. Several effective asymmetric reactions were achieved with Pd-MOP catalyst: asymmetric hydrosilylation of alkyl-substituted terminal olefins, asymmetric 1,4-hydroboration of 1,3-enynes, and asymmetric reduction of allylic esters with formic acid.

While high selectivities were obtained in many reactions using some of the chiral diphosphine ligands in FIG. 1, there are many reactions where these ligands are not very efficient in terms of activity and selectivity. There are many disadvantages associated with these ligands, which hinder their applications. For DIPAMP, the phosphine chiral center is difficult to make. This ligand is only useful for limited application in asymmetric hydrogenation. For BPPM, DIOP, and Skewphos, the methylene group in the ligands causes conformational flexibility and enantioselectivities are moderate for many catalytic asymmetric reactions. DEGPHOS and CHIRAPHOS coordinate transition metals in five-membered ring. The chiral environment created by the phenyl groups is not close to the substrates and enantioselectivities are moderate for many reactions. BINAP, DuPhos and BPE ligands are good for many asymmetric reactions. However, the rotation of the aryl—aryl bond makes BINAP very flexible. The flexibility is an inherent limitation in the use of phosphine ligand. Furthermore, because the phosphine of BINAP contains three adjacent aryl groups, it is less electron-donating than a phosphine that has less aryl groups. This is an important factor influencing reaction rates. For hydrogenation reactions, electron-donating phosphines are more active. For the more electron-donating DUPHOS and PBE ligands, the five-membered ring adjacent to the phosphines is flexible.

Chiral bidentate phosphites with a rigid backbone are rare in the literature. The strategy of rigidifying chiral phosphines can be applied to make new chiral phosphites. An example is to rigidify the Union Carbide chiral bisphosphite ligands with a BICP diol. This will be useful to develop asymmetric hydroformylation reactions. There are only few reports about asymmetric catalysis with transition metal complexes with chiral monophosphines. Bulky and conformationally rigid chiral monophosphines as well as their hemilabile version of these ligands are made for asymmetric catalytic reactions.

There remains a need to develop and apply chiral phosphine ligands to a variety of asymmetric reactions such as hydrogenation, hydride transfer reaction, hydrosilylation, hydroboration, hydrovinylation, olefin metathesis, hydroformylation, hydrocarboxylation, allylic alkylation, cyclopropanation, Diels-Alder reaction, Aldol reaction, Heck reaction and Michael addition are explored based on these innovative ligand systems. Success would lead to efficient and practical methods for producing important chiral drugs for anti-hypertensive, antihistamine, cardiovascular, and central nervous system therapies.

Much effort has been devoted to the development of efficient asymmetric synthetic methods for the preparation of enantiomerically enriched compounds. Among various methods for the enantiomerically selective synthesis of chiral organic compounds from prochiral precursors, enantioselective catalytic hydrogenation of dehydro precursors has been extensively developed. In fact, asymmetric hydrogenation is one of the most practical methods in asymmetric synthesis, accounting for 70% of all procedures used on a commercial scale. However, most asymmetric catalytic hydrogenation systems only hydrogenate electron deficient olefins with high enantioselectivity and high reactivity. In contrast, electron-rich olefins, such as simple enamides and enolates, are generally poor substrates for asymmetric hydrogenation with most known systems (T. Monmoto, M., et al., Chem. Pharm. Bull. 1992, 40, 2894; H. B. Kagan, et al., J. Organomet. Chem. 1975, 90, 353; D. Sinou, et al., J. Organomet. Chem. 1976, 114, 325; highly enantioselective hydrogenation of enamines was achieved using a chiral titanocene catalyst: N. E. Lee, et al., J. Am. Chem. Soc., 1994, 116, 5985; J. M. Brown, et al., J. Chem. Soc. Perkin II 1982, 489; K. E. Koenig, et al., J. Org. Chem. 1980, 45, 2362; R. Selke, et al., J. Mol. Catal. 1986, 37, 213; M. D. Fryzuk, et al., J. Am. Chem. Soc. 1978, 100, 5491; K. E. Koenig in Asymmtric Synthesis; Vol 5 (Ed: J. D. Morrison), Academic Press, New York, 1985, Chapter 3). Since enamides and enolates upon asymmetric hydrogenation can be converted to enantiomerically pure amines and alcohols, it would be extremely desirable to have a general and efficient method for this transformation. It was difficult to synthesize isomerically pure enamides using older methods. Recently, Burk and coworkers have reported that Rh-complexes bearing the electron-rich DuPhos and BPE type ligands were efficient catalysts for the asymmetric hydrogenation of enamides and enolates (M. J. Burk, et al., J. Am. Chem. Soc. 1996, 118, 5142; M. J. Burk, et al., J. Am. Chem. Soc. 1991, 113, 8518). They reported that analogous Rh-chiral bisphosphines bearing diphenylphosphino groups (e.g., BINAP, DIOP and CHIRAPHOS) led to significantly lower enantioselectivities in the reduction of enamides (<60% ee).

We have been interested in elucidating the steric and electronic effects of various diphenylphosphino-bearing chiral ligands in asymmetric hydrogenation processes. Recently a new chiral 1,4-bisphosphine, (2R,2'R)-bis (diphenylphosphino)-(1R,1'R)-dicyclopentane ((R,R)-BICP), was reported from our laboratory as an excellent ligand for the Rh-catalyzed asymmetric hydrogenation of dehydroamino acids (G. Zhu, et al., J. Am. Chem. Soc. 1997, 119, 1799). In this new ligand, four stereogenic centers are introduced in a conformationally rigid bicyclic backbone, which is fundamentally different from either axially dissymmetric BINAP or bisphosphines with two stereogenic centers. Among chiral bisphosphines with diphenylphosphino groups, the BICP ligand gives high enantioselectivity for the rhodium-catalyzed asymmetric hydrogenation of simple enamides.

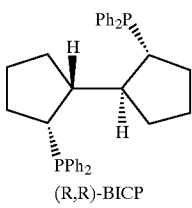
(R,R)-BICP

SUMMARY OF THE INVENTION

One aspect of the invention is in providing a chiral compound selected from L1, L2, L3, and L4 and corresponding enantiomers:

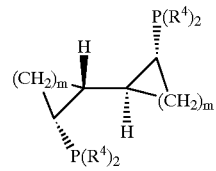
(L1)

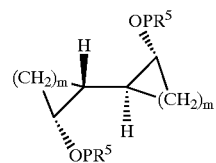
(L2)

wherein m ranges from 1 to 8 to form a ring, wherein the ring may be unsubstituted or substituted and may be part of a fused ring; $R^4$ is unsubstituted or substituted aryl or alkyl;

$R^5$ is

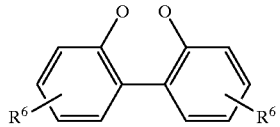

wherein each $R^6$ independently represents two substituents which are independently C1–C5 alkyl or alkoxy groups, each meta to the bond joining the phenyl rings;

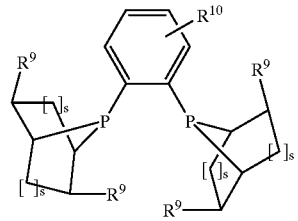
(L3)

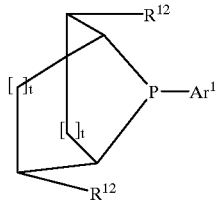
(L4)

wherein s ranges from 1 to 4; t ranges from 1 to 4; $R^9$ is unsubstituted or substituted aryl or alkyl; $R^{10}$ is hydrogen, or one or more unsubstituted or substituted aryl or alkyl groups; $R^{12}$ is one or more unsubstituted or substituted aryl or alkyl groups; and $Ar^1$ is unsubstituted or substituted aryl.

Another aspect of the invention is in providing a catalyst comprising one of the above compounds at an optical purity of at least 85% ee and a transition metal.

The present invention further provides a process comprising subjecting a substrate to an asymmetric reaction in the presence of such a catalyst, wherein said asymmetric reaction is a hydrogenation, hydride transfer, hydrosilylation, hydroboration, hydrovinylation, olefin metathesis, hydroformylation, hydrocarboxylation, allylic alkylation, cyclopropanation, Diels-Alder, Aldol, Heck, [m+n] cycloaddition, or Michael addition reaction.

The ligands of the invention in FIG. 2 have at least four chiral centers in their backbones and can form chelating rings with many transition metals.

BICP has four stereogenic carbon centers in the backbone. This structure is fundamentally different from either axially dissymmetric BINAP or bisphosphines with two stereogenic carbon centers in their backbone such as Chiraphos, DIOP and BPPM.

The rigid, fused phosphabicyclo[2.2.1]heptane structure in ligands such as PennPhos is a new structural motif.

There are many transition metal catalyzed reactions that do not work with chelating bidentate ligands. Efficient chiral monophosphines of the present invention are clearly needed.

The availability of chiral phosphines is always a worthwhile consideration for practical applications of the chemistry. Early phosphine systems such as Diop, DegPhos and BPPM relied on chiral pool species for the origin of ligand chirality. This approach necessarily permits only limited structural diversity in the ligands. Other chiral phosphine ligands, e.g., DIPAMP, BINAP and DuPhos, were made by chiral resolution and asymmetric synthesis. Ligand synthesis is often a challenging synthetic task. We choose our ligand synthesis routes based on readily available starting materials such as cyclopentanone and paraxylene.

Fine-tuning the steric and electronic properties of chiral phosphine ligands is important. With the chiral phosphabicyclo[2.2.1]heptane systems, varying alkyl substituents is easy and this variation will provide a different steric environment around the transition metal. For the diphenylphosphine systems bearing chiral backbones, electronic properties can be altered by substituting phenyl with other aromatic groups. Finally, changing the chiral backbones of the phosphines adds another dimension to varying steric and electronic properties. The bite angle P-M-P is different from one ligand to another.

Accordingly, an advantage of the invention is to provide new chiral ligand structural motifs. A further advantage of the invention is to provide new chiral ligand structural motifs allowing greater ligand structural diversity.

A further advantage of the invention is to provide new chiral monodentate phosphine ligands.

A further advantage of the invention is to provide methods of carrying out asymmetric synthesis using chiral phosphine and phosphite ligands.

A further advantage of the invention is to provide methods for efficient asymmetric carbon-hydrogen bond formation.

A further advantage of the invention is a method of performing the asymmetric hydrogenation of enamides and cyclic enamides using chiral catalysts.

A further advantage of the invention is to provide methods for efficient asymmetric hydrogenation of imines, enol acetates, enol ethers, or alkenes.

A further advantage of the invention is to provide methods for efficient asymmetric carbon—carbon bond formation.

A further advantage of the invention is to provide methods for efficient asymmetric hydroformylation or hydrovinylation.

Additional advantages of the invention will be set forth in part in the description that follows, and in part will be obvious from the description, or may be learned by practice of the invention. The objects and advantages of the invention will be realized and attained by means of the elements and combinations particularly pointed out in the appended claims. Both the foregoing general description and the following detailed description of the invention are exemplary and explanatory only and are not necessarily restrictive of the claimed invention.

DETAILED DESCRIPTION OF THE INVENTION

Figure 1:
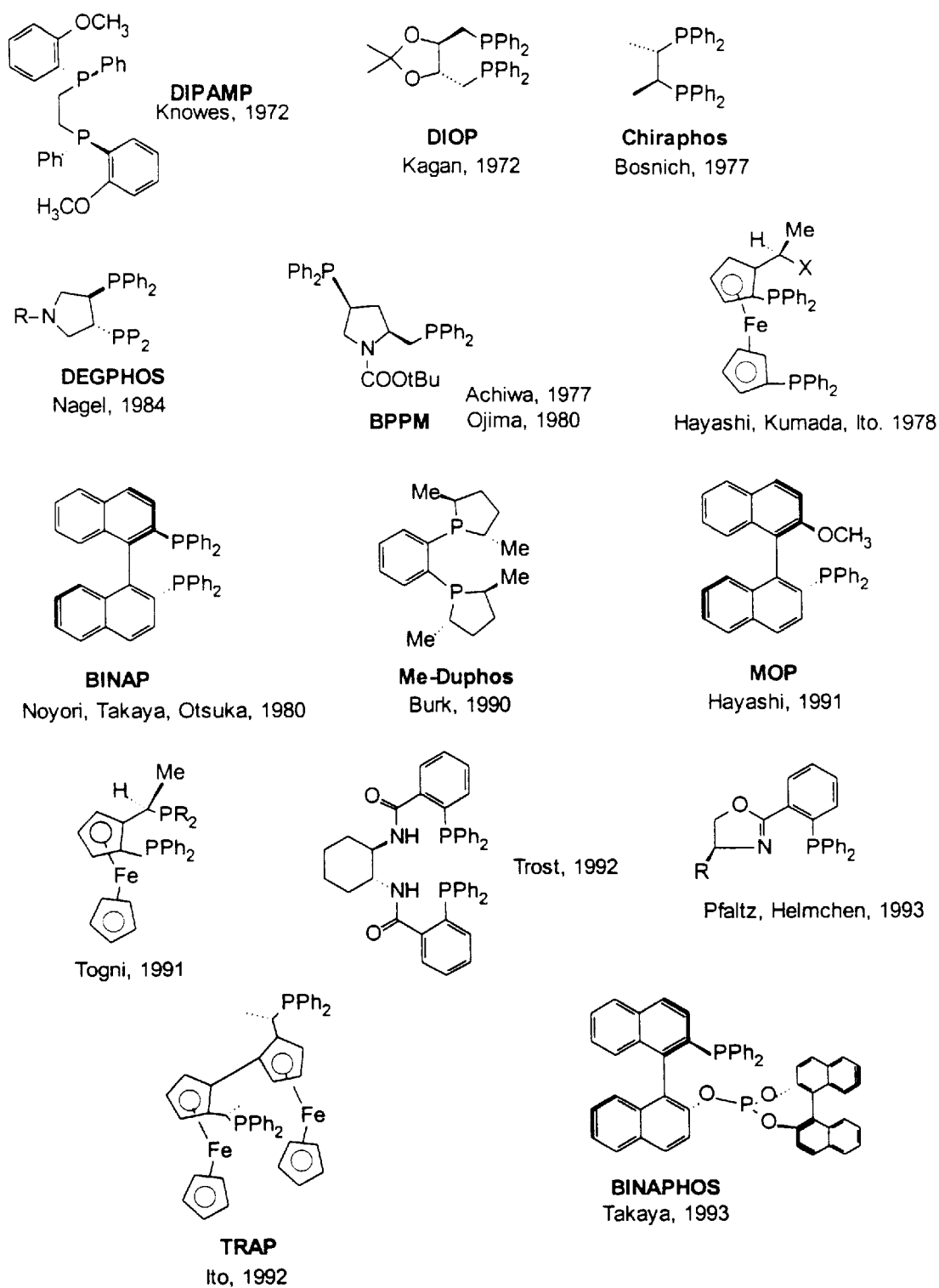
FIG. 1 shows structures of poor art ligands.
Figure 2:
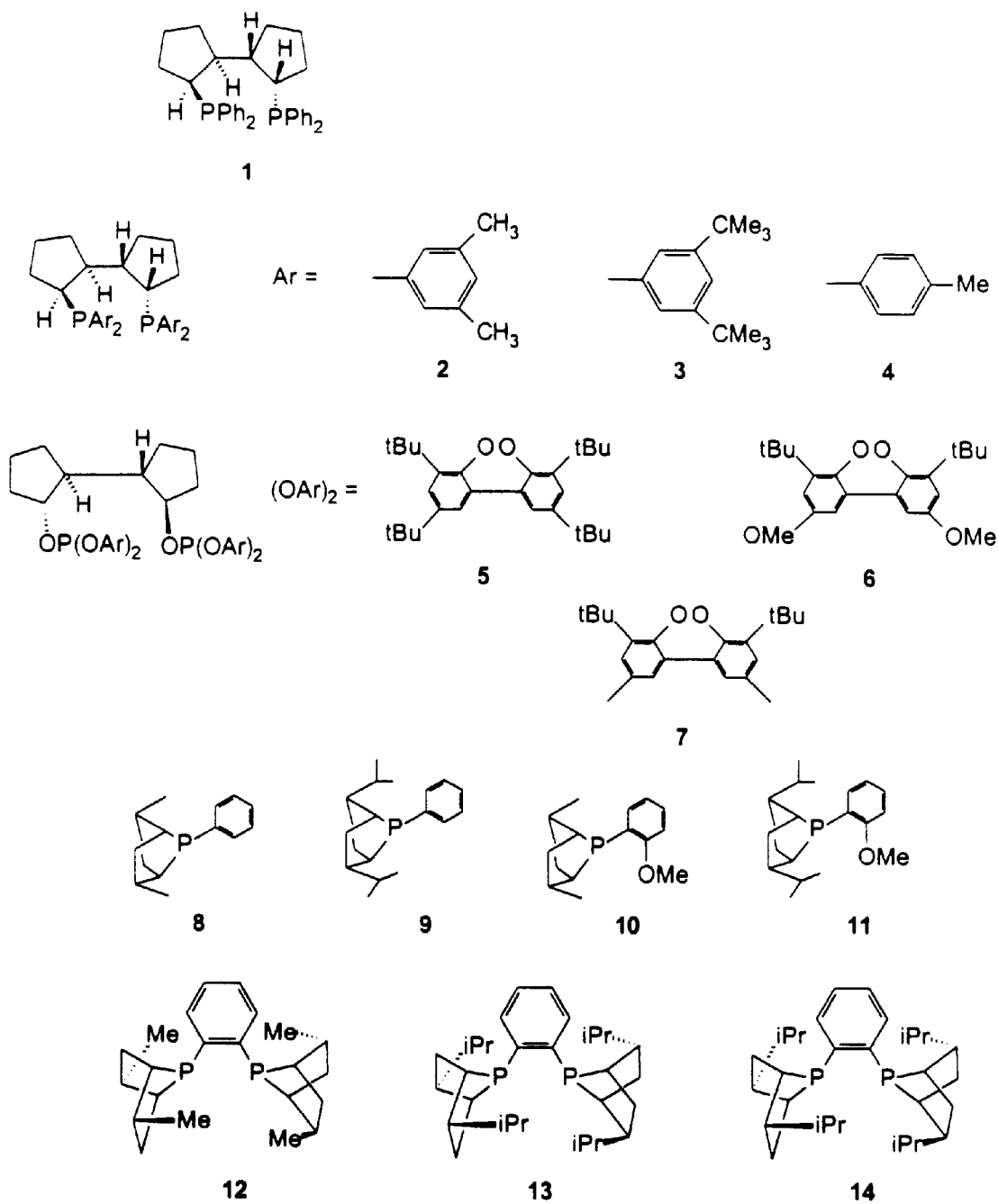
FIG. 2 shows structures of new chiral ligands.

The following definitions are used. Other abbreviations well known to persons of skill in the art of asymmetric synthesis are also used in this specification.

% ee: enantiomeric excess, (% S−% R)/(% S+% R) or (% R−% S)/(% S+% R)
acac: acetylacetonate
COD: 1,5-cyclooctadiene
HMPA: hexamethylphosphoramide
Ipc: isopinocampheyl
MOM: methoxymethyl
Otf: trifluoromethanesulfonate
DBA: dibenzylideneacetone The chiral ligands L1–L4 of the present invention may contain alkyl and aryl groups. These alkyl and aryl groups may be substituted without particular restriction, provided that the substituents do not have an adverse effect on the asymmetric reaction, and are inert to the reaction conditions or are thereby converted in a desirable manner.

The substrates of the asymmetric synthesis of the invention may be a wide range of compounds, e.g., compounds containing C=C, C=O, or C=N bonds. These substrates may also contain alkyl and aryl groups that may be unsubstituted or substituted.

By alkyl is meant any straight, branched, or cyclic alkyl group. The number of carbons in the alkyl group is not particularly limited. Preferably, alkyl refers to C1–C20, more preferably C1–C8, even more preferably C1–C4 alkyl groups. Examples of such alkyl groups include, but are not limited to, methyl, ethyl, propyl, isopropyl, butyl, sec-butyl, tert-butyl, pentyl, isopentyl, tert-pentyl, hexyl, isohexyl, and cyclopropyl, cyclobutyl, cyclopentyl, and cyclohexyl, and isomers of heptyl, octyl, and nonyl. Alkyl groups may be substituted with without particular restriction, provided that the substituents do not have an adverse effect on the asymmetric reaction, and are inert to the reaction conditions or are thereby converted in a desirable manner. Examples of such substituents include, but are not limited to, aryl, heterocyclo, alkoxy, halo, haloalkyl, amino, alkylamino, dialkylamino, nitro, amido, and carboxylic ester groups, and any suitable combination thereof.

By aryl is meant any aromatic or heteroaromatic ring, including such rings fused to other aliphatic, aromatic or heteroaromatic rings. Examples of aromatic rings include, but are not limited to, phenyl, naphthyl, anthryl, fluorenyl, indenyl, and phenanthryl. Heteroaromatic rings may contain one or more heteroatoms, preferably one or more atoms of nitrogen, oxygen, or sulfur. Examples of heteroaromatic rings include, but are not limited to, pyrrole, pyridine, quinoline, isoquinoline, indole, furan, and thiophene. Aryl groups may be substituted without particular restriction, provided that the substituents do not have an adverse effect on the asymmetric reaction, and are inert to the reaction conditions or are thereby converted in a desirable manner. Examples of such substituents include, but are not limited to, alkyl, aryl, heterocyclo, alkoxy, halo, haloalkyl, amino, alkylamino, dialkylamino, nitro, amido, and carboxylic ester groups, and any suitable combination thereof.

Substrates undergoing asymmetric reactions may also contain non-aromatic heterocyclic rings. These may be fused rings and may contain, besides carbon atoms, one or more atoms of nitrogen, oxygen, or sulfur. Examples include, but are not limited to, pyrrolidine, piperidine, piperazine, indoline, and tetrahydrofuran.

The optical purity of the ligand is preferably at least about 85% ee, more preferably at least about 90% ee, more preferably at least about 95% ee, even more preferably at least about 98% ee, and even more preferably about 100% ee.

As is well known to a person skilled in the art of asymmetric synthesis, a chiral ligand can exist as two enantiomers of opposite configuration. A person skilled in the art will recognize that for any given asymmetric reaction, each enantiomer will produce products of opposite configuration from the other, but with the same conversion and optical purity. In this specification, ligand and product structures are shown for one enantiomer for convenience. Of course, the disclosure also applies to the corresponding enantiomers of opposite configuration, and a person skilled in the art can select the appropriate enantiomer to achieve the desired product configuration.

In chiral ligands L1 and L2 of the present invention, m preferably ranges from 2 to 6, more preferably from 3 to 4. In chiral ligand L1, $R^4$ preferably represents unsubstituted or substituted phenyl. In chiral ligand L2, $R^6$ preferably represents at least a C1–C4 alkyl group ortho to the oxygen-bearing carbon on each phenyl ring.

In chiral ligand L3, s preferably ranges from 1–2, $R^9$ is preferably C1–C8 alkyl, more preferably C1–C4 alkyl, even more preferably unsubstituted C1–C4 alkyl, and $R^{10}$ is preferably hydrogen.

In chiral ligand L4, t preferably ranges from 1–2, $R^{12}$ is preferably unsubstituted or substituted C1–C8 alkyl, more preferably C1–C4 alkyl, even more preferably unsubstituted C1–C4 alkyl. $Ar^1$ is preferably unsubstituted or substituted phenyl, more preferably phenyl substituted with C1–C4 alkyl or alkoxy, even more preferably phenyl ortho-substituted with C1–C4 alkyl or alkoxy.

The chiral ligands L1–L4 provide an asymmetric catalyst with a transition metal. The catalyst preferably comprises a Group VIII transition metal, more preferably rhodium, iridium, ruthenium, nickel, platinum or palladium.

The catalyst preferably comprises a Group VIII transition metal and one of the following compounds 1–14:

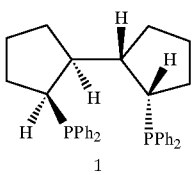

1

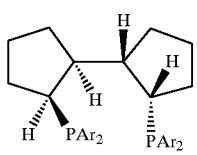

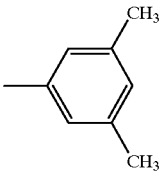

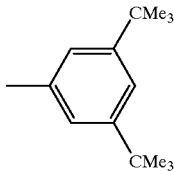

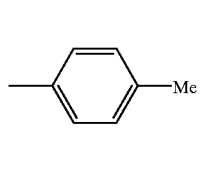

2  3  4

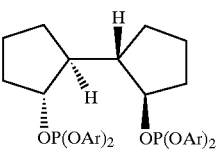

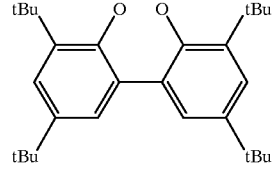

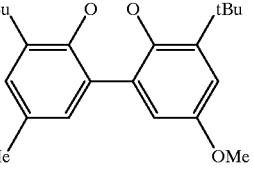

5  6

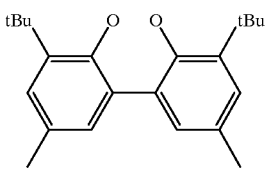

7

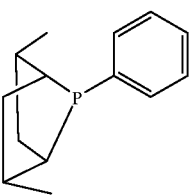

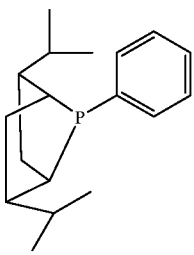

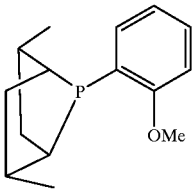

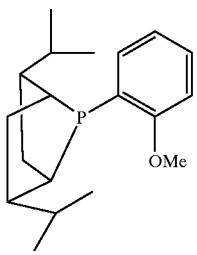

8  9  10  11

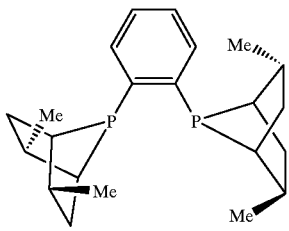

12

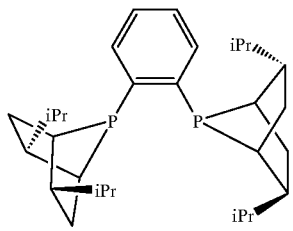

13

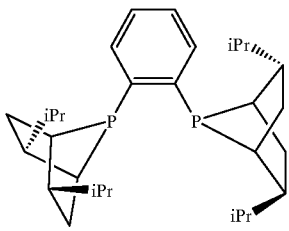

14

In one embodiment of the invention, the catalyst may be prepared in situ by reacting a compound of claim 1 and a precursor complex of a Group VIII transition metal and ligand. Examples of precursor complex ligands include, but are not limited to, DBA, OAc, COD, acac, methylallyl, and aryl ligands. Preferably, the precursor complex is $Pd_2(DBA)_3$, $Pd(OAc)_2$; $[Rh(COD)Cl]_2$, $[Rh(COD)_2]X$, $Rh(acac)(CO)_2$; $RuCl_2(COD)$, $Ru(COD)(methylallyl)_2$, $Ru(Ar)Cl_2$, wherein Ar is an aryl group, unsubstituted or substituted with an alkyl group; $[Ir(COD)Cl]_2$, $[Ir(COD)_2]X$; or Ni(allyl)X, wherein X is a counterion. The counterion X may generally be any suitable anion for use in asymmetric synthesis. A person of skill in the art can readily determine what such a suitable counterion would be for any particular set of ligands, reaction conditions and substrates. Examples of suitable counterions include, but are not limited to, halogen ions (including $Cl^-$, $Br^-$, and $I^-$), $BF_4^-$, $ClO_4^-$, $SbF_8^-$, $CF_3SO_3^-$, $BAr_4^-$ (wherein Ar is aryl), and $Otf^-$.

A substrate may be subjected to many asymmetric reactions in the presence of such a catalyst. Examples of such asymmetric reactions include, but are not limited to, hydride transfer, hydrosilylation, hydroboration, hydrovinylation, olefin metathesis, hydroformylation, hydrocarboxylation, allylic alkylation, cyclopropanation, Diels-Alder, Aldol, Heck, [m+n] cycloaddition, and Michael addition reactions.

The process is generally suitable for asymmetric carbon-hydrogen bond formation. In particular, the process is suitable for hydrogenation of a ketone, imine, or olefin. The process is also suitable for hydrogenation of an enamide, β-keto ester, enol acetate, or enol ether.

One embodiment of the invention is a hydrogenation process comprising subjecting a substrate to an asymmetric reaction in the presence of such a catalyst.

Hydrogen is generally maintained at a pressure ranging from about 1 atm to about 100 atm, preferably from about 1 atm to about 10 atm, more preferably from about 1 atm to about 5 atm. The reaction is preferably carried out at a temperature of ranging from about −20° C. to about 100° C., more preferably from about 0° C. to about 50° C., even more preferably at about room temperature.

For hydrogenation, the substrate may be of formula (S1) or (S2) to provide a product of formula (P1) or (P2):

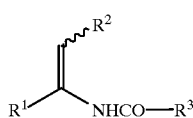

(S1)

(P1)

(S2)

(P2)

wherein:

$R^1$ is hydrogen, or unsubstituted or substituted alkyl or aryl; $R^2$ is hydrogen, unsubstituted or substituted C1–C12 alkyl, unsubstituted or substituted aryl, —$COOR^{18}$ wherein $R^{18}$ is unsubstituted or substituted C1–C12 alkyl or aryl, or $OR^{19}$ wherein $R^{19}$ is a hydroxy protecting group; $R^3$ is hydrogen, unsubstituted or substituted C1–C12 alkyl, or unsubstituted or substituted aryl; and n ranges from 0 to 6 to form unsubstituted or substituted ring, wherein the ring may contain an atom of N, O, or S and wherein said ring may be fused to a second ring of 3 to 10 carbons, wherein said second ring may be aliphatic or aromatic and may contain an atom of N, O, or S.

In another embodiment of the invention, the substrate may S1

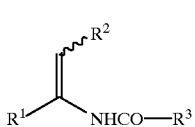

(S1)

wherein $R^1$ is unsubstituted or substituted phenyl or naphthyl; $R^2$ is unsubstituted or substituted C1–C5 alkyl, —$COOR^{18}$ wherein $R^{18}$ is unsubstituted or substituted C1–C5 alkyl, or $OR^{19}$ wherein $R^{19}$ is a hydroxy protecting group; and $R^3$ is unsubstituted C1–C5 alkyl; and the catalyst comprises rhodium and

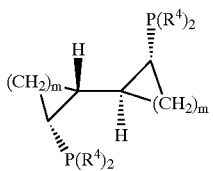

wherein m ranges from 3 to 4 to form an unsubstituted or substituted ring; $R^4$ is unsubstituted or substituted phenyl.

In another embodiment of the invention, the substrate is

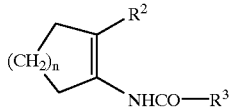

wherein n ranges from 1 to 3 to form an unsubstituted or substituted ring, wherein the ring may contain an atom of N, O, or S and wherein said ring may be fused to a second ring of 3 to 10 carbons, wherein said second ring may be aliphatic or aromatic and may contain an atom of N, O, or S; $R^2$ is hydrogen or unsubstituted C1–C5 alkyl; and $R^3$ is unsubstituted C1–C5 alkyl; and the catalyst comprises rhodium and

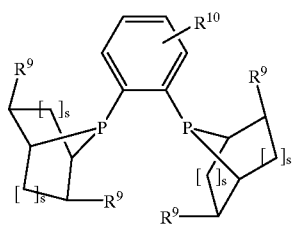

wherein s ranges from 1 to 2; $R^9$ is unsubstituted or substituted C1–C4 alkyl; and $R^{10}$ is hydrogen.

In another embodiment of the invention, the product formed is an aminotetralin or an aminoindan.

In another embodiment of the invention, the substrate is a compound of formula (S3) to provide a compound of formula (P3):

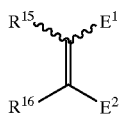

(S3)

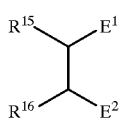

(P3)

wherein E1 and E2 are independently O—(C=O)>$R^{18}$, COOR$^{18}$, HN(C=O)R$^{18}$, or O—R$^{19}$, wherein $R^{18}$ is hydrogen, or unsubstituted or substituted aryl or alkyl, and $R^{19}$ is hydrogen, unsubstituted or substituted aryl or alkyl, or a hydroxy protecting group; and $R^{15}$ and $R^{16}$ are independently hydrogen, or unsubstituted or substituted aryl or alkyl; wherein $R^{15}$ and $R^{16}$ or $R^{16}$ and E2 together may form an unsubstituted or substituted ring of 3 to 10 carbons, wherein said ring may contain an atom of N, O, or S and wherein said ring may be fused to a second ring of 3 to 10 carbons, wherein said second ring may be aliphatic or aromatic and may contain an atom of N, O, or S.

In another embodiment of the invention, the substrate is a β-keto ester and the catalyst comprises a compound of formula L1,

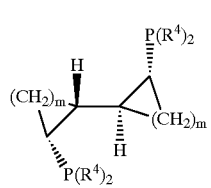

(L1)

wherein m ranges from 2 to 4 to form an unsubstituted ring; and $R^4$ is a phenyl group substituted with at least one C1–C5 alkyl group in the meta or para positions.

The process is generally suitable for asymmetric carbon—carbon bond formation. In another embodiment of the invention, the process is part of a hydroformylation reaction. In this embodiment, the catalyst preferably comprises ruthenium and a compound of formula L2,

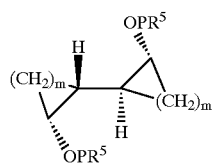

(L2)

wherein m ranges from 2 to 4 to form an unsubstituted ring; and

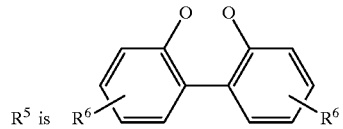

wherein each $R^6$ independently represents two substituents which are independently C1–C5 alkyl or alkoxy groups, each meta to the bond joining the phenyl rings.

In another embodiment of the invention, the process is part of a hydrovinylation reaction. In this embodiment the catalyst preferably comprises nickel and a compound of formula L4,

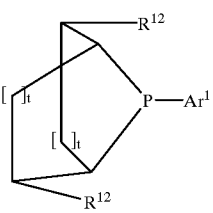

(L4)

wherein t ranges from 1 to 2; $R^{12}$ is a C1–C5 alkyl; and $Ar^1$ is phenyl, unsubstituted or substituted by C1–C4 alkyl.

In another embodiment of the invention, the substrate is an imine. In this embodiment, the catalyst preferably comprises iridium and a compound of formula L1. The substrate is preferably a compound of formula (S4):

(S4)

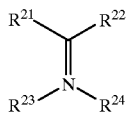

wherein $R^{21}$, $R^{22}$, $R^{23}$, and $R^{24}$ are independently hydrogen, or unsubstituted or substituted aryl or alkyl; wherein $R^{21}$ and $R^{22}$ together may form an unsubstituted or substituted ring of 3 to 10 carbons, wherein said ring may contain an atom of N, O, or S and wherein said ring may be fused to a second ring of 3 to 10 carbons, wherein said second ring may be aliphatic or aromatic and may contain an atom of N, O, or S, and wherein $R^{21}$ and $R^{23}$, $R^{22}$ and $R^{24}$, or $R^{23}$ and $R^{24}$ may together form an unsubstituted or substituted ring containing 3 to 10 carbons in addition to the imine nitrogen, wherein said ring may be fused to a second ring, wherein said second ring is as defined above.

Imine hydrogenation may be carried out at hydrogen pressures well over 100 psi. For example, hydrogen pressure ranging from 800 to 1200 psi may be used, or 900 to 1100 psi.

Imine hydrogenation is preferably carded out with up to about 20% of an additive. The actual amount added will depend on the specific additive, but can be as little as about 0.5%. The amount used will generally range from about 1% to about 15%. The additive is preferably an imide. Examples of suitable additives include, but are not limited to, phthalimide, phthalimide, phthalimide, phthalimide, phthalimide, phthalimide, phthalimide, phthalimide, phthalimide, succinimide, hydanton, 2,3-naphthalene-dicarboximide, 4,5-dichlorophthalimide, N—Me-phthalimide, N—K-phthalimide, N—Br-phthalimide, phthalic anhydride, and 1,3-indandione.

The present invention is further illustrated by the following examples, which are designed to teach those of ordinary skill in the art how to practice the invention. The following examples are illustrative of the invention and should not be construed as limiting the invention as claimed.

EXAMPLES

LIGAND SYNTHESIS

Unless otherwise indicated, all reactions were carried out under nitrogen. THF and ether were freshly distilled from sodium benzophenone ketyl. Toluene and 1,4-dioxane were freshly distilled from sodium. Dichloromethane and hexane were freshly distilled from $CaH_2$. Methanol was distilled from magnesium and $CaH_2$. Reactions were monitored by thin-layer chromatography (TLC) analysis. Column chromatography was performed using EM silica gel 60 (230–400 mesh). $^1H$ NMR were recorded on Bruker ACE 200, WP 200, AM 300 and WM 360 spectrometers. Chemical shifts are reported in ppm downfield from tetramethylsilane with the solvent resonance as the internal standard ($CDCl_3$, δ 7.26 ppm). $^{13}C$, $^{31}P$ and $^1H$ NMR spectra were recorded on Bruker AM 300 and WM 360 or Varlan 200 or 500 spectrometers with complete proton decoupling. Chemical shifts are reported in ppm downfield from tetramethylsilane with the solvent resonance as the internal standard ($CDCl_3$, δ 77.0 ppm). Optical rotation was obtained on a Perkin-Elmer 241 polarimeter. MS spectra were recorded on a KRATOS mass spectrometer MS 9/50 for LR-El and HR-El. GC analysis were carried on Hewlett-Packard 5890 gas chromatograph with a 30-m Supelco β-DEX™ column. HPLC analyses were carried on Waters™ 800 chromatograph with a 25-cm CHIRALCEL OD column.

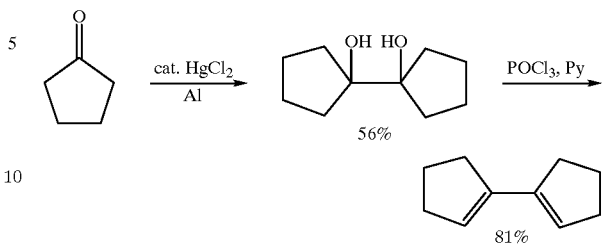

1,1'-Dihydroxy-1,1'-dicyclopentyl

To a 2 L three-necked round bottom flask, mercuric chloride (20 g, 73 mmol) and benzene (300 ml) was added. Coarse aluminum powder (40 g, 1.48 mol) was added to this mixture at the rate of keeping benzene at refluxing. The mixture was stirred at room temperature for 15 min. Cyclopentanone (200 g, 2.4 mol) was added dropwise to the suspension of Al—Hg alloy in benzene (~8 h) and the mixture was stirred for additional 2 h. The reaction mixture was cooled at 0° C. and iced water (100 mL) was added. Diethyl ether (300 mL) was added to extract products. The mixture was filtered through a celite and the filtrate was washed with ether. The combined organic phase was dried over $Na_2SO_4$ and evaporated under vacuum. 1,1'-Dihydroxy-1,1'-dicyclopentyl (1) (120 g) was obtained as a white solid, yield 56%.

1,1'-dicyclopentenyl

To a 250 mL Schlenk flask under $N_2$, pyridine (84 mL, dried over NaOH), $POCl_3$ (17 mL) and 1,1'-Dihydroxy-1,1'-dicyclopentyl (1, 17 g) was added. The mixture was heated until the reaction took place (vigorous initiation as an exothermic reaction). The mixture was then cooled at an ice bath to prevent overheating. The mixture was heated to 100° C. for 6 h. Ice water (300 mL) was added to this mixture and stir at room temperature for 30 minutes. The mixture was extracted with pentane (3×200 mL) and the pentane extracts was washed with 10% hydrochloric acid (3×20 mL), aqueous sodium bicarbonate (30 mL), water (30 mL) and the dried over sodium sulfate. Removal of the pentane followed by distillation gave the product (55° C. at 1 mm) as a light yellow liquid. Yield=81%. $^1H$ NMR ($CDCl_3$): 5.6 (s, 4H), 2.52–2.41 (m), 1.96–1.83 (m) ppm.

Ligand Example 1, BICP: (2R,2'R)-Bis(diphenylphosphino)-(1R,1'R)-dicyclopentane (1R,1'R)-Bicyclopentyl-(2S,2'S)-diol This compound was synthesized by asymmetric hydroboration of bi-1-cyclopenten-1-yl using (+)-monoisopinocampheylborane ((4)-$IpcBH_2$) according to the literature procedure (Brown, H. C.; Jadhav, P. K., Mandal, A. K. J. Org. Chem. 1982, 47, 5074). The solution of enantiomerically pure (+)-$IpcBH_2$ (0.6 M, 200 mmol, 300 mL in ether) was cooled to −20° C. and HCl in ether (200 mL, 1.0 M, 200 mmol) was slowly added to this solution. The mixture was allowed to stir for 30 min at 0° C. and then was cooled to −25° C. 1,1'-dicyclopentyl (10 g, 75 mmol) was added and the mixture was stirred at −25° C. for 24 h.

The mixture was warmed to 0° C. and stirred for another 24 h. The reaction was quenched with methanol at −25° C. Usual hydroperoxide work-up was performed according to H. C. Brown's procedure. The crude mixture was purified by chromatography (first hexane/ethyl acetate (5:1), then hexane/ethyl acetate (3:1). The first component is pinene alcohol, the second component is desired diol (2.56 g, yield 18.3%, 93% ee) and the third component is meso diol (7.3 g, yield 58%). The absolute configuration of the diol was assigned based on the asymmetric hydroboration of trisubstituted olefins (e.g. methylcyclopentene) using (+)-IpcBH$_2$. 1H NMR (CDCl$_3$, 300 MHz) δ 4.04 (br, 2H), 3.84 (m, 2H), 2.02 (m, 2H), 1.66–1.22 (m, 10H), 1.21 (m, 2H); $^{13}$C NMR δ 78.6, 52.2, 33.6, 29.2, 20.5; MS m/z 170 (M+, 0.35), 152, 134, 108, 95, 84, 68; HRMS calcd for C$_{10}$H$_{18}$O$_2$: 170.1307 (M$^+$); found: 170.1315. Enantiomeric excess was determined by a chiral capillary GC column (Supelco TM γ-DEX 225, 160° C. t meso diol=19.88 min, (1R,1'R, 2S,2'S) diol=20.92 min, (1S,1'S,2R,2'R) diol=21.42 min).

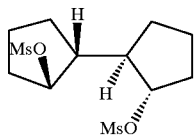

(1R,1'R)-Bicyclopentyl-(2S,2'S)-diol bis(methanesulfonate)

To a solution of (1R,1'R)-bicyclopentyl-(2S,2'S)-diol (0.8 g, 4.65 mmol) and triethylamine (1.68 mL, 12.09 mmol) in CH$_2$Cl$_2$ (30 mL) was added dropwise a solution of methanesulfonyl chloride (0.76 mL, 9.92 mmol) in CH$_2$Cl$_2$ (2 mL) at 0° C. The reaction mixture was stirred at 0° C. for 30 min, and at room temperature for 2 h, then quenched by saturated aqueous ammonium chloride solution (25 mL). The aqueous layer was extracted with CH$_2$Cl$_2$ (3×20 mL) and the combined organic solution was dried over Na$_2$SO$_4$. After evaporation of the solvent, a white solid was obtained, which was used directly for the next step. $^1$H NMR (CDCl$_3$, 200 MHz) δ 5.01 (m, 2H), 3.04 (s, 6H), 2.17 (m, 2H), 2.15–1.65 (m, 10H), 1.43–1.52 (m, 2H); $^{13}$C NMR δ 86.8, 48.2, 38.4, 32.8, 27.4, 22.5.

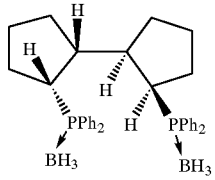

(1R,1'R,2R,2'R)-1,1'-Bis(2diphenylphosphino)cyclopentyl bisborane

Diphenylphosphine (1.25 mL, 7.0 mmol) in THF (80 mL) was cooled to −78° C. To this solution, n-BuLi in hexane (4.1 mL, 6.6 mmol) was added via syringe over 5 min. The resulting orange solution was warmed to room temperature and stirred for 30 min. After cooling the mixture to −78° C., (1R,1'R,2S,2'S)-1,1'-bicyclopentyl-2,2'-diol bismesylate (1.01 g, 3.1 mmol) in THF (20 mL) was added over 20 min. The resulting orange solution was warmed to room temperature and stirred overnight. The white suspension solution was hydrolyzed with saturated aqueous NH$_4$Cl solution. The aqueous layer was extracted with CH$_2$Cl$_2$ (2×20 mL). The combined organic solution was dried over anhydrous Na$_2$SO$_4$. After removal of the solvents under reduced pressure, the residue was dissolved in CH$_2$Cl$_2$ (50 mL), then treated with BH$_3$·THF (10 mL, 10 mmol) at room temperature and the mixture was stirred overnight. The reaction mixture was added to NH$_4$Cl aqueous solution, and extracted with CH$_2$Cl$_2$ (2×50 mL). The combined organic solution was dried over anhydrous Na$_2$SO$_4$. After evaporation of the solvent under reduced pressure, the residue was subjected to column chromatography on silca gel, eluting with CH$_2$Cl$_2$/hexane (1:5) and then CH$_2$Cl$_2$/hexane (2:3) affording the product as a white solid. Yield: 0.36 g (21%). $^1$H-NMR (CDCl$_3$) δ 7.80–7.30 (m, 20H, Ph), 2.55–2.35 (m, 2H, CHP(BH$_3$)Ph$_2$), 1.95–1.35 (m, 14H, CH$_2$ and CH), 1.7–0.5 (broad, 6H, BH3). $^{31}$P-NMR (CDCl$_3$): δ P=17.5 (br). $^{13}$C-NMR (CDCl$_3$) δ 133.43 (d, $^2$J(PC)=8.5 Hz, C$_{ortho}$), 132.25 (d, $^2$J(PC)=8.5 Hz, C$_{ortho}$), 132.08 (d, $^1$J(PH)=50.0 Hz, C$_{ipso}$), 130.67 (d, $^4$J(PC)=2.1 Hz, C$_{para}$), 130.57 (d,$^4$J(PC)=2.1 Hz, C$_{para}$), 129.71 (d, $^1$J(PC)=56.5 Hz, C$_{ipso}$), 128.39 (d, $^3$J(PC)=9.4 Hz, C$_{meta}$), 128.29 (d, $^3$J(PC)=9.1 Hz, C$_{meta}$), 46.28 (dd, J(PC)=2.1 and 4.8 Hz, C$_{1,1}$'), 36.26 (d, $^1$J(PC)=30.6 Hz, C$_{2,2}$'),31.19 (CH$_2$), 29.52 (CH$_2$), 22.51 (CH$_2$); MS m/z 520 (8.95), 506 (3.55), 429 (19.10), 321 (100), 253 (7.45), 185 (26.64), 108 (43.68), 91 (11.99), 77 (6.88), HRMS cacld for C$_{28}$H$_{31}$ P$_2$ (M+—B$_2$H$_6$—Ph): 429.1901, found: 429.1906.

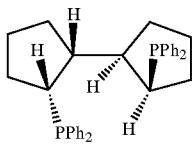

BICP: (2R,2'R)-Bis(diphenylphosphino)-(1R,1'R)-dicyclopentane

To a solution of the above borane complex of the phosphine (0.24 g, 0.45 mmol) in CH$_2$Cl$_2$ (4.5 mL) was added tetrafluoroboric acid-dimethyl ether complex (0.55 mL, 4.5 mmol) dropwise via syringe at −5° C. After the addition, the reaction mixture was allowed to warm slowly to room temperature, and stirred for 20 h. The mixture was diluted with CH$_2$Cl$_2$, and neutralized with saturated aqueous NaHCO$_3$ solution. The aqueous layer was extracted with CH$_2$Cl$_2$. The combined organic solution was washed with brine, followed by water, and dried over Na$_2$SO$_4$. Evaporation of the solvent gave the pure phosphine. Yield: 0.21 9 (93%). $^1$H NMR (CDCl$_3$, 360 MHz) δ 7.52–7.27 (m, 20H), 2.53 (m, 2H), 2.27 (m, 2H), 1.93 (m, 2H), 1.72 (m, 2H), 1.70–1.43 (m, 8 H); $^{13}$C NMR (CDCl$_3$) δ 39–127 (Ph), 45.9 (d, J=12.1 Hz), 45.8 (d, J=12.0 Hz), 40.34 (d, J=14.0 Hz), 30.9 (m), 23.8 (m); $^{31}$P NMR (CDCl$_3$) δ −14.6. This phosphine was fully characterized by its borane complex.

Ligand Example 1a. Synthesis of Modified BICP Ligand

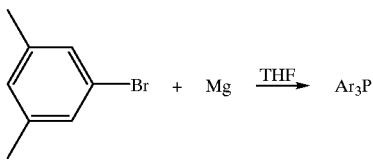

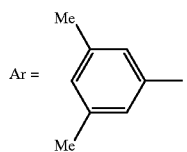

To a mixture of Mg (6.70 g, 0.275 mmol) in THF (150 mL) was added a solution of bromide (50 g, 0.262 mmol) in THF (50 mL) dropwise. After addition, the mixture was cooled to room temperature, and then stirred at room temperature for another hour. The reaction mixture was cooled to 0° C., a solution of PCl$_3$ (5.08 mL, 58 mmol) in THF (10 mL) was added slowly. Then the reaction mixture was heated at reflux for 2 hr. The reaction mixture was quenched by NH$_4$Cl (sat. aq.) at 0° C. Extracted by benzene, combined organic layer was washed by NaHCO$_3$, and brine. After dried over sodium sulfate, the solvent was removed under reduced pressure. The product was obtained by recrystallization from EtOH, 10.5 g.

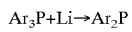

To a solution of triaryl phosphine (28.0 g, 80.8 mmol) in THF (210 mL) was added Li (1.17 g, 2.08 eq) in portions. Then the reaction was stirred at room temperature for two days. The reaction was quenched by adding water at 0° C., and stirred until all solid was dissolved. Extracted with ether (3×40 mL). Combined organic layer was washed with HCl (1–2% aq., followed by water (40 mL×3). Dried over Na$_2$SO$_4$, after the solvent was evaporated, the product was obtained by distillation: 16.0 g, 160–165° C./0.2 mm Hg.

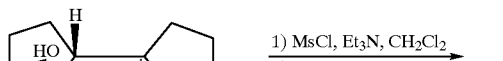

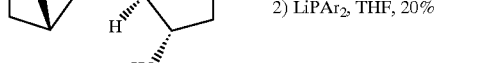

(1R,1'R)-Bicyclopentyl-(2S,2'S)-diol bis(methanesulfonate)

To a solution of (1R,1'R)-bicyclopentyl-(2S,2'S)-diol (1 g, 5.87 mmol) and triethylamine (2.13 mL) in CH$_2$Cl$_2$ (40 mL) was added dropwise a solution of methanesulfonyl chloride (0.973 mL) in CH$_2$Cl$_2$ (2 mL) at 0° C. After 30 min at 0° C., the reaction mixture was stirred for additional 2 h at room temperature, then quenched by saturated aqueous ammonium chloride solution (25 mL). The aqueous layer was extracted with CH$_2$Cl$_2$ (3×20 mL) and the combined organic solution was dried over Na$_2$SO$_4$. After evaporation of the solvent, a white solid was obtained which was used directly for the next step. $^1$H NMR (CDCl$_3$, 200 MHz) δ 5.01 (m, 2H), 3.04 (s, 6H), 2.17 (m, 2H), 2.15–1.65 (m, 10H), 1.43–1.52 (m, 2H); $^{13}$C NMR δ 86.8, 48.2, 38.4, 32.8, 27.4, 22.5.

(1R,1'R,2R,2'R)-1,1'-Bis(2-diarylphosphino)cyclopentyl bisborane

To a solution of diarylphosphine (3.19 g) in THF (140 mL) was added n-BuLi in hexane (7.7 mL, 1.6 M) at –78° C. over 5 min via syringe. The resulting orange solution was warmed to room temperature and stirred for 30 min. After cooling the mixture to –78° C., (1R,1'R,2S,2'S)-1,1'-bicyclopentyl-2,2'-diol bismesylate in THF (20 mL) was added over 30 min. The resulting orange solution was warmed to room temperature and stirred overnight. The white suspension solution was hydrolyzed with saturated aqueous NH$_4$Cl solution. The aqueous layer was extracted with CH$_2$Cl$_2$ (3×20 mL), and the combined organic solution was dried over anhydrous Na$_2$SO$_4$. After removal of the solvents under reduced pressure, the residue was dissolved in CH$_2$Cl$_2$ (90 mL), then treated with BH$_3$·THF (19 mL) at room temperature and the mixture was stirred overnight. The reaction mixture was added to NH$_4$Cl aqueous solution, and extracted with CH$_2$Cl$_2$ (3×50 mL). The combined organic solution was dried over anhydrous Na$_2$SO$_4$. After evaporation of the solvent under reduced pressure, the residue was subjected to column chromatography on silica gel. Yield: 1.0 g, [α]$_D^{25}$=–9.63 (c 1.36, CHCl$_3$); $^1$H NMR (CDCl$_3$, 300 MHz) δ 7.25~7.21 (m, 4H), 7.07 (s, 2H), 7.00~6.98 (m, 4H), 6.94 (s, 2H), 2.40 (s, 12H), 2.34 (s, 12H), 2.33~2.19 (m, 2H), 1.83~1.29 (m, 14H); $^{13}$C NMR (CDCl$_3$) δ 139.9~125.2 (Ph), 47.6~47.1 (m), 39.1 (d, 14.0 Hz), 30.9 (m), 22.4 (m), 21.4, 21.3; $^{31}$P NMR(CDCl$_3$) δ –16.9.

(2R,2'R)-Bis(diarylphosphino)-(1R,1'R)-dicyclopentane (1). To a solution of the above borane complex of the phosphine (0.95 g mmol) in CH$_2$Cl$_2$ (14.6 mL) was added tetrafluoroboric acid-dimethyl ether complex (1.79 mL) dropwise via syringe at –5° C. After the addition, the reaction mixture was allowed to warm slowly to room temperature, and stirred for 20 h. The mixture was diluted with CH$_2$Cl$_2$, and neutralized with saturated aqueous NaHCO$_3$ solution. The aqueous layer was extracted with CH$_2$Cl$_2$. The combined organic solution was washed with brine, followed by water, and dried over Na$_2$SO$_4$. Evaporation of the solvent gave the pure phosphine.

Ligand Example 2. (1R,2S,4R,5S)-(+)-2,5-Dimethyl-7-phenyl-7-phosphabicyclo[2.2.1]heptane borane

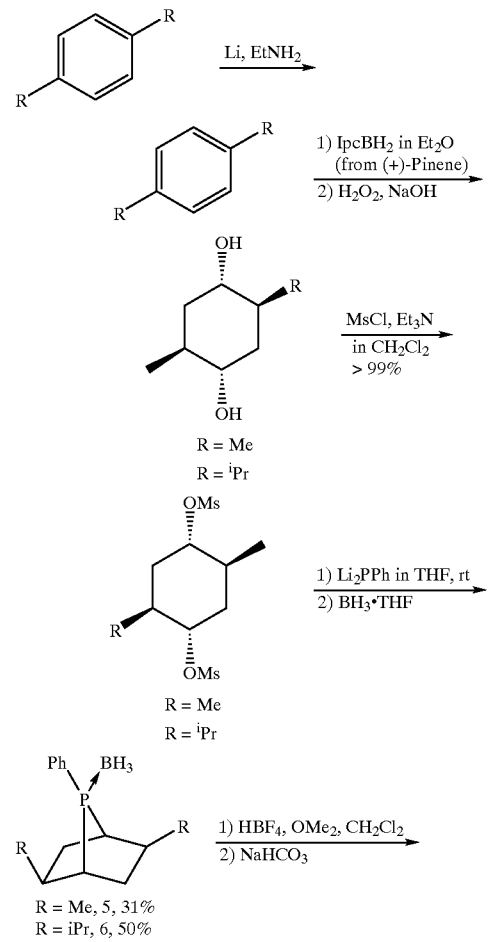

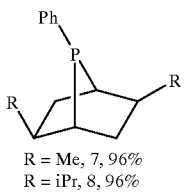

R = Me, 7, 96%
R = iPr, 8, 96%

1,4-Dimethylcyclohexane-1,4-diene

To an 1 L flask fitted with cooling finger (−78° C.) and a stirring bar was charged with 250 ml ethylamine and the solution was cooled to 0° C. Then anhydrous p-xylene (54.9 g, 64 ml, 517 mmol) was added followed by the addition of ethyl alcohol (3×60 ml). Lithium wires (5.6 g) was added after each portion of ethyl alcohol (totally 16.8 g Lithium was added). After 3 h, the mixture was quenched with ice water (heat evolved). The aqueous layer was extracted with ether (3×150 mL), then dried over anhydrous sodium sulfate. The solvent was removed by rotary evaporation. The residue was distilled and the product (30 g, 53.7%) was collected at 135–140° C.

(1S,2R,4S,5R)-(+)-2,5-Dimethylcyclohexane-1,4-diol

A 500 ml flask fitted with a rubber septum and a magnetic stirring bar was charged with IpcBH$_2$ (assumed 0.6M, 300 ml, 181 mmol, derived from (1R)-(+)-α-pinene, 98%, 92+% ee, Aldrich) in ether and cooled to −25° C. 1,4-Dimethylcyclohexane-1,4-diene (7.5 g, 69.3 mmol) was added via syringe over 4 min. The reactants were stirred for 24 h at −25° C. and for 24 h at 0° C. The mixture was quenched with methanol (12.8 ml, 316 mmol) dropwise at −25° C. (hydrogen evolved). The solution was transferred to a 2 L flask and cooled to 0° C., then oxidized by successive slow addition of sodium hydroxide (4 M, 119 ml, 475 mmol) and hydrogen peroxide (30%, 49 mL, 475 mmol). The mixture was maintained at room temperature overnight. Two layers separated. The aqueous layer was extracted with ether (3×150 mL) The combined organic portion was dried over anhydrous sodium sulfate, and the solvent was removed under vacuum. The oily residue was subjected to flash chromatography (Silica gel, 5:1 methylene chloride/acetone) and give first pinene alcohol, Ci-symmetrical diol and then desired C$_2$-symmetrical diol as a white solid (5.5 g, 55%, 96% ee by GC using a Supleco β-120 column).

(1S,2R,4S,5R)-Dimethylcyclohexane-1,4-dimesylate

To a solution of (1S,2R,4S,5R)-Dimethylcyclohexane-1,4-diol (16 g, 111 mmol) and triethylamine (37.6 mL, 267 mmol) in dry methylene chloride (500 mL) was added dropwise the solution of methanesulfonyl chloride (17.3 mL, 221.3) in methylene chloride (30 mL) at 0° C. The mixture was stirred for 30 min at 0° C. and for 2.5 h at room temperature. The reaction was quenched with saturated ammonium chloride solution (200 mL) at 0° C. The aqueous layer was extracted with methylene chloride (3×150 mL). The combined organic phase was dried over anhydrous sodium sulfate and concentrated under vacuum, gave a light yellow solid. This product was pass through a short column of silica gel eluted with methylene chloride, which gave the desired product as a white solid (33.3 g, 99.9%).

To phenylphosphine (3.0 ml, 27.3 mmol) in THF (200 mL) was added n-BuLi (34.5 mL of a 1.6 M solution in hexane, 55 mmol) via syringe at −78° C. over 20 min. Then the orange solution was warmed up to room temperature and stirred for 1 hr at room temperature. To the resulting orange-yellow suspension was added a solution of (1S,2S,4S,5S)-2,5-dimethyl-cyclohexane-1,4-diol bis(methanesulfonate) (8.25 g, 27.5 mmol) in THF (100 mL) over 15 min. After the mixture was stirred overnight at room temperature, the pale-yellow suspension was hydrolyzed with saturated NH$_4$Cl solution. The mixture was extracted with ether (2×50 mL), and the combined organic solution was dried over anhydrous sodium sulfate. After filtration, the solvents were removed under reduced pressure. The residue was dissolved in methylene chloride (100 mL), treated with BH$_3$·THF (40 mL of a 1.0 M solution in THF, 40 mmol) and the mixture was stirred overnight. It was then poured into saturated NH$_4$Cl solution and extracted with CH$_2$Cl$_2$ (3×50 mL). The combined organic solution was dried over anhydrous Na$_2$SO$_4$ and filtered, the solvent was removed on reduced pressure. The residue was subjected to chromatography on a silica gel column, eluted with hexanes/CH$_2$Cl$_2$ (4:1) affording the product as a white solid. Yield: 1.95 g (31%). [α]$_D^{25}$=+59.50 (c 1.07, CHCl$_3$). $^1$H-NMR (CDCl$_3$) δ 7.60–7.30 (m, 5H, C$_6$H$_5$), 2.60–2.40 (m, 2H, CHP(BH$_3$)Ph), 2.15–2.05 (m, 1H, CH), 2.04–1.80 (m, 4H, CH$_2$), 1.65–1.50 (m, 1H, CH), 1.32 (d, $_3$J(HH)=6.5 Hz, 3H, CH$_3$), 0. 59 (d, $^3$J(HH)=6.7 Hz, 3H, CH$_3$), 1.6–0.2 (br, BH$_3$); $^{13}$C-NMR (CDCl$_3$) δ 131.74 (d, $^2$J(PC)=7.3 Hz, C$_{ortho}$), 130.56 (d, $^1$J(PC)=43.9 Hz, C$_{ipso}$), 129.92 (d, $^4$J(PC)=2.0 Hz, C$_{para}$), 128.44 (d, $^3$J(PC)=8.6 Hz, C$_{meta}$), 43.07 (d, $^1$J(PC)=30.5 Hz, CHP(BH$_3$)Ph), 40.85 (d, $^1$J(PC)=31.6 Hz, CHP(BH$_3$)Ph), 36.27 (CH$_2$), 36.67 (d, $^3$J(PC)=13.5 Hz, CH$_2$), 35.91 (d, $^2$J(PC)=3.5 Hz, CH), 34.65 (d, $^2$J(PC)=9.8 Hz, CH), 20.78 (CH$_3$) 20.53 (CH$_3$); $^{31}$P-NMR (CDCl$_3$) δ 36.3 (d, broad, $^1$J(PB)=58.8 Hz); HRMS Calcd for C$_{14}$H$_{22}$BP: 232.1552 (M$^+$): found 232.1578: C$_{14}$H$_{19}$P: 218.1224 (M$^+$—BH$_3$); found: 218.1233.

Ligand Example 3, (1R,2R,4R,5R)-(+)-2,5-Diisopropyl-7-phenyl-7-phosphabicyclo[2.2.1]heptane Borane The same procedure was used as in Ligand Example 2. Yield: 0.33 g (50%). [α]$_D^{25}$=+25.5° (c 1.02, CHCl$_3$). $^1$H-NMR (CDCl$_3$) δ 7.55–7.30 (m, 5H, C$_6$H$_5$), 2.85–2.70 9 (m, 2H CHP(BH$_3$)Ph), 2.30–2.20 (m, 1H, CH), 2.18–2.00 (m, 1H, CH), 1.95–1.65 (m, 4H, CH$_2$), 1.40–1.20 (m, 2H, CH), 1.03 (d, $^3$J(PH)=6.5 Hz, CH$_3$), 0.87 (d, $^3$J(PH)=6.7 Hz, CH$_3$), 0.85 (d, $^3$J(PH)=7.4 Hz, CH$_3$), 0.53 (s, broad, 3H, CH$_3$), 1.5–0.2 (broad, BH$_3$); $^{13}$C-NMR (CDCl$_3$) δ 131.19 (d, $^2$J(PC)=8.3 Hz, C$_{ortho}$), 130.71 (d, $^1$J(PC)=45.2 Hz, C$_{ipso}$), 129.97 (d, $^4$J(PC)=2.5 Hz, C$_{para}$), 128.45 (d, $^3$J(PC)=9.5 Hz, C$_{meta}$), 50.30 (d, $^2$J(PC)=2.1 Hz, CH), 48.77 (d, $^2$J(PC)=9.7 Hz, CH), 38.27 (d, $^1$J(PC)=30.5 Hz, CHP(BH$_3$)Ph), 36.81 (CH$_2$), 36.71 (d, $^1$J(PC)=31.5 Hz, CHP(BH$_3$)Ph), 34.73 (d, $^3$J(PC)=13.7 Hz, CH$_2$), 31.92 (CHMe$_2$), 31.12 (CHMe$_2$), 22.41 (CH$_3$), 21.55 (CH$_3$), 20.73 (CH$_3$), 20.10 (CH$_3$); $^{31}$P-NMR (CDCl$_3$) δ 36. d (d, broad, $^1$J(PB) 51.4 Hz).

Ligand Example 4, (1R,2S,4R,5S)-(+)-2,5-Dimethyl-7-phenyl-7-phosphabicyclo[2.2.1]heptane To a solution of corresponding borane complex of the phosphine (5, 1.0 g, 4.31 mmol) in CH$_2$Cl$_2$ (22 mL) was added tetrafluoroboric acid-dimethyl ether complex (2,63 mL, 21.6 mmol) dropwise via a syringe at −5° C. After the addition, the reaction mixture was allowed to warm up slowly, and stirred at room temperature. After 20 h, $^{31}$P NMR showed the reaction was over, it was diluted by CH$_2$Cl$_2$, neutralized by saturated NaHCO$_3$ aqueous solution. The aqueous layer was extracted with CH$_2$Cl$_2$. The combined organic solution was washed with brine, followed by water, and then dried over Na$_2$SO$_4$. Evaporation of the solvent gave a pure phosphine product, which was confirmed by NMR. Yield: 0.9 g (96%). [α]$^{25}_D$=+92.5° (c 2.3, toluene); $^1$H NMR (CDCl$_3$, 360 MHz) δ 7.38–7.34 (m, 2H), 7.26–7.21 (m, 2H), 7.19–7.16 (m 1H), 2.60–2.54 (m, 2H), 1.89–1.62 (m, 5H), 1.44–1.42 (m, 1H), 1.16 (d, J=6.12 Hz, 3H), 0.55 (d, J=6.95 Hz, 3H); $^{13}$C NMR (CDCl$_3$) δ 138.68 (d, J=29.3 Hz), 131.42 (d, J=13.0 Hz), 127.88 (d, J 2.35 Hz), 126.57 (s), 47.34 (d, J=13.5 Hz), 45.26 (d, J=10.2 Hz), 39.21 (d, J=6.7 Hz), 39.21 (d, J=5.3 Hz), 38.74 (d, J=6.7 Hz), 34.69 (d, 17.2 Hz), 22.37 (d, J 7.8 Hz), 21.52 (s); $^{31}$P NMR(CDCl$_3$) δ −7.29.

Ligand Example 5, (1R,2R,4R,5R)-(+)-2,5-Diisopropyl-7-phenyl-7-phosphabicyclo[2.2.1]heptane The same procedure was used as in Ligand Example 4. Yield: 1.0 g (95.5%). [α]$_D^{25}$=+43.90 (c 1.2, toluene); $^1$H NMR (CDCl$_3$, 360 MHz) δ 7.35–7.30 (m, 2H), 7.24–7.14 (m, 3H), 2.94–2.85 (m, 2H), 1.76–1.53 (m, 5H), 1.25–1.14 (m, 2H), 1.06 (d, J=7.77 Hz, 3H), 0.95–08.0 (m, 1H), 0.87 (dd, J=3.77 Hz, 7.89 Hz, 6H), 0.49 (d, J=9.30 Hz, 3H); $^{13}$C NMR (CDCl$_3$) δ 138.83 (d, J=30.49 Hz), 130.69 (d, J=12.2 Hz), 127.71 (d, J=2.87 Hz), 126.45 (s), 53.38 (d, J=6.34 Hz), 48.63 (d, J=17.06 Hz), 41.97 (d, J=13.43 Hz), 40.51 (d, J=9.96 Hz), 37.60 (d, J=11.09 Hz), 37.39 (d, J=9.74 Hz), 33.03 (d, 6.11 Hz), 31.86 (s), 21.89 (s), 21.78 (s), 21.23 (s), 20.40 (s); $^{31}$P NMR(CDCl$_3$) δ −7.49.

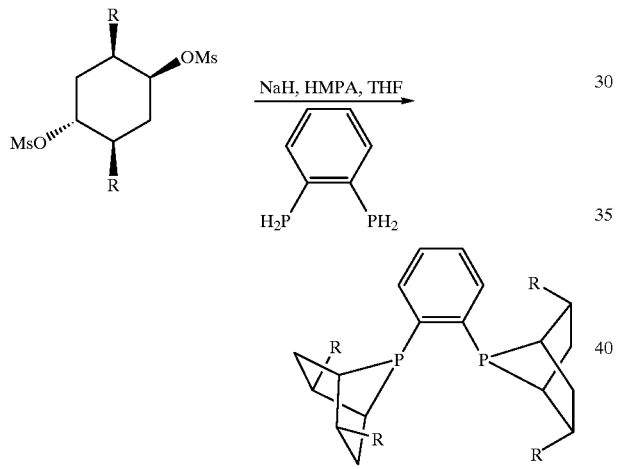

Ligand Example 6, Me-PennPhos: 1,2-Bis{(1R,2S,4R,5S)-2,5-dimethyl-8-phenylphospha-bicyclo[2.2.1]heptyl}benzene To the suspension of NaH (8.0 g, 333 mmol) in THF (200 ml), cooled to 0° C., was added 1,2-diphosphinobenzene (4,0 ml, 30.4 mmol), followed by HMPA (80 ml). The resulting orange suspension was stirred at 0° C. for 1 h. (1S,2S,4S,5S)-2,5-dimethylcyclohexane-1,4-diol dimesolate (18.3 g, 60.9 mmol) in THF (150 ml) was added over 20 min. The resulting orange-red suspension was stirred at room temperature for 3.5 days, hydrolyzed with NaCl-H$_2$O and then extracted with hexane (2×100 ml). The combined organic solution was dried over Na$_2$SO$_4$. After filtration, the solvents were removed under reduced pressure. The residue was subjected to chromatography on silica gel column, eluted with hexane. Yield: 3.0 g (27.5%). $^1$H-NMR (CDCl$_3$): δH=7.25–7.10 (m, 2H, aromatic), 7.08–6.95 (m, 2H, aromatic), 3.21 (d, broad, 2H, 2J(PH)=14.5 Hz, PCH), 2.58 (d, broad, 2H, $^2$J(PH)=13.4 Hz, PCH), 1.90–1.60 (m, 12H), 1.55–1.35 (m, 2H), 1.17 (d, 6H, $^3$J(HH)=6.3 Hz, CH$_3$), 0.60 (d, 6H, $^3$J(HH)=6.3 Hz, CH$_3$). CH. $^{13}$C-NMR (is out of first order, CDCl$_3$): δC=143.94, 143.66, 143.48, 143.20, 131.05, 131.00, 130.93, 126.33, 46,24, 46.20, 46,17, 46.13, 45.92, 45.69, 45.61, 45.38, 40.17, 40.05, 39.89, 39.73, 39.61, 39.52, 39.33, 39.29, 39.26, 34.76, 34.61. 34.51, 34.41, 34.26, 22.69, 22.65, 22.61, 20.82. $^{31}$P-NMR (CDCl$_3$): δP=−7.3 ppm.

Ligand Example 7, i-Pr-PennPhos:1,2-Bis{(1R,2R,4R,5R)-2,5-bis-isopropyl-phenylphospha-bicyclo[2.2.1]heptyl}benzene 1,2-diphosphinobenzene (0.4 ml, 3.04 mmol) and NaH (0.9 g, 37.5 mmol) were mixed in THF (50 ml) and cooled to 0° C. HMPA (8.5 ml, 49 mmol) was added. The resulting orange suspension was stirred at 0° C. for 1 h and then (1S,2S,4S,5S)-2,5-dimethyl-cyclohexane-1,4-diol dimesolate (2.17 g, 6.08 mmol) in THF (40 ml) was added over 10 min. The resulting orange-red suspension was stirred at room temperature for 3 days. After cooled to 0° C., it was hydrolyzed with NaCl-H$_2$O, and extracted with hexane (2×50 ml). The combined organic solution was dried over Na$_2$SO$_4$ and filtered. The solvents were removed under reduced pressure. The residue was subjected to chromatography on silica gel column, eluted with hexane. Yield: 0.6 g (42%). $^1$H-NMR (CDCl$_3$): δH=7.20–7.10 (m, 2H, aromatic), 7.05–6.90 (m, 2H, aromatic), 3.38 (d, broad, 2H, $^2$J(PH)=14.2 Hz, PCH), 2.85 (d, broad, 2H, $^2$J(PH)=13.5 Hz, PCH), 1.85–1.45 (m, 12H), 1.30–1.08 (m, 4H), 1.03 (d, 6H, $^3$J(HH)=6.4 Hz, CH$_3$), 0.96 (d, 6H, $^3$J(HH)=5.6 Hz, CH$_3$), 0.86 (d, 6H, $^3$J(HH)=6.5 Hz, CH$_3$), 0.47 (s, 6H, CH$_3$). $^{13}$C-NMR (is out of first order, CDCl$_3$). δC=143.97, 143.62, 143.56, 143.50, 143.45, 143.09, 130.96, 130.90, 130.86, 126.11, 54.10, 54.06, 54.03, 48.65, 48.56, 48.46, 42.02, 41.96, 41.24, 41.20, 41.18, 41.14, 37.94, 37.77, 37.60, 37.46, 33.29, 33.27, 33.24, 31.69, 23,45, 23.40, 23.35, 22.22, 20.97, 20.54. $^3$P-NMR (CDCl$_3$): δP=−8.7 ppm.

HYDROGENATION OF ENAMIDES

The utility of the invention is broad. The current art can be extended to the synthesis of e.g., many chiral amines, amino alcohols and amino acids. For the hydrogenation of enamides, the examples of the invention greatly extend the scope of the substrates. The following discussion contains information on the synthesis of substrates. From these, many compounds can be made for the first time using transition metal-BICP. PennPhos and DuPhos catalysts.

For the synthesis of enamides, several other methods are known:

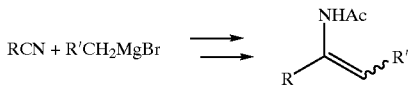

Kagan, H. B. et al. J. Organometal. Chem. 1975, 90, 353.

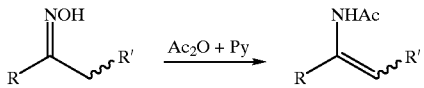

Barton, D. H. R. et al. J. Chem. Soc. Perk I, 1975, 1237.

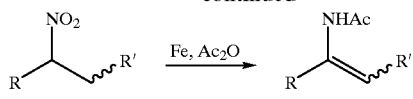

Zard, S. Z. et al. Tetrahedron Lett.
1996, 37, 1605.

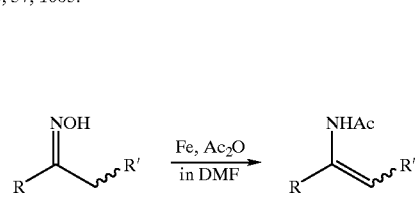

Casalnuovo, A. L. DuPont Agriculture
Products Burk, M. J. Chirotech
Technology Ltd. (Fe, AC$_2$O)

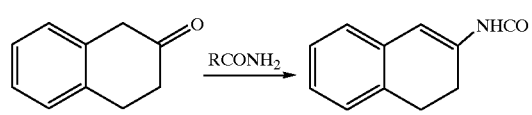

Tschen, D. M. el at. J. Org. Chem.
1995, 50, 4321.

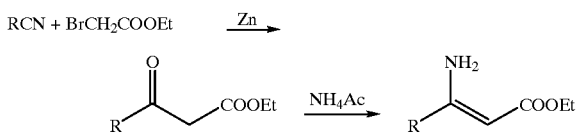

Lee, S. -YA. Et al. Tetrahedron Lett.
1997, 38, 443.

Asymmetric Hydrogenation of Enamides

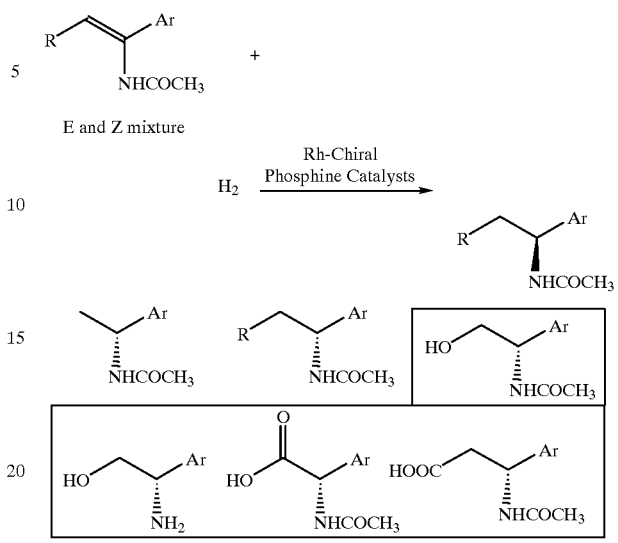

Key Step: Easy Synthesis of Enamides

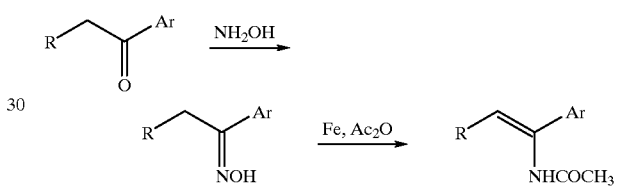

The application for the synthesis of chiral drugs can be outlined by new drug candidates.

Excellent enantioselectivities have been obtained using Rh-PennPhos and Rh-BICP catalysts. This is especially true for cyclic enamides. For example, chiral 1-aminoindane and 1-amino-1,2,3,4-tetrahydronaphthalene can be obtained with 98% ee.

Asymmetric Hydrogenation of Enamides

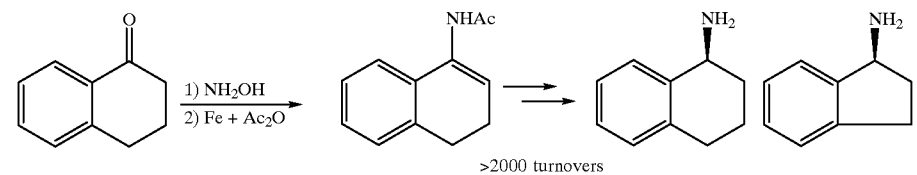

| | Enamide | | | |
|---|---|---|---|---|
| Ligand | Ph-C(=CH$_2$)-NHCOCH$_3$ | Ph-C(=CHR)(H$_3$C)-NHCOCH$_3$ | dihydronaphthalene-NHAc | indene-NHAc |
| BICP | 86% ee | 95% ee | 65% ee | 60% ee |
| Me-PennPhos | 88% ee | 90% ee | 98% ee | 98% ee |

Practical Synthesis of Chiral 1-Aminotetralines and 1-Aminoindans

Potential Applications of Chiral Amines

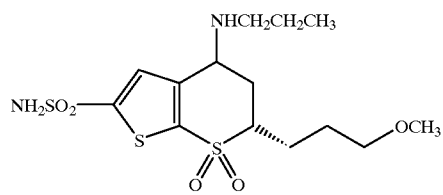

Merck (MDL-693612)
Antiglaucoma (Phase I)

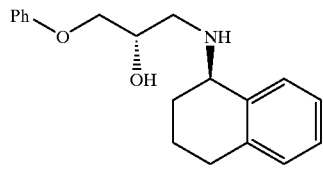

Sanofi (SR-59230A)
Irritable Bowel Syndrome
(Preclinical)

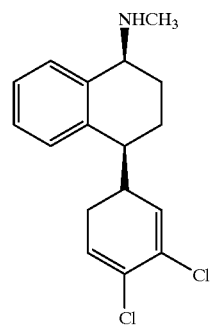

Zoloft-Sertraline
(Pfizer)

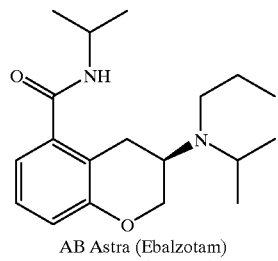

AB Astra (Ebalzotam)
Migraine (Phase II)

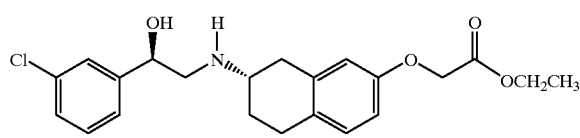

Sanofi (SR-58611A)
Antiobesity (Phase II)

For the related problems, the synthesis can lead to efficient ways of many other compounds such as cis-aminoalcohols, epoxides.

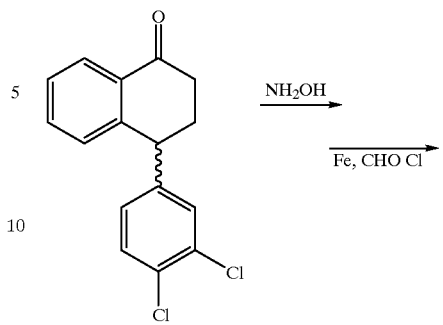

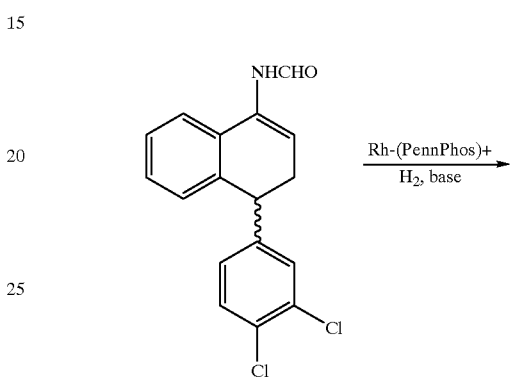

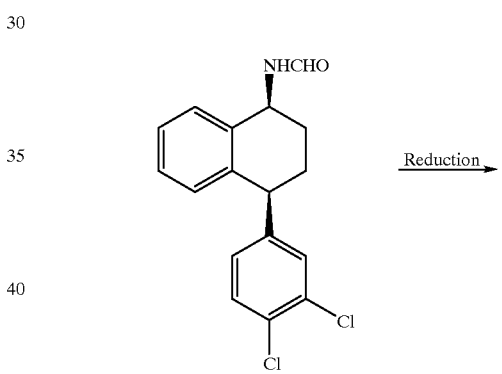

Zoloft-Sertraline (Pfizer)

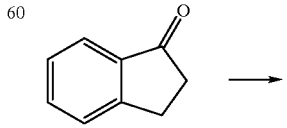

29

-continued

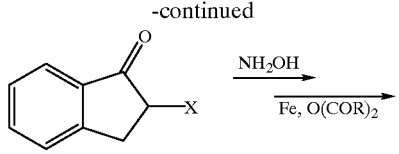

PG = MOM, COR, SiR₃

Example 1, Hydrogenation of Enamides

The active catalyst was generated in situ from a cationic Rh-complex, [Rh(COD)₂]BF₄ or [Rh(COD)₂]OTf, and bisphosphine BICP (1:1.2). Enamide 31a was chosen as a model substrate to screen various reaction conditions. As shown in Table 1, the solvent had little effect on the enantioselectivities for this reaction. Under 40 psi H₂ at room temperature, reaction in non-polar solvents such as benzene (85.2% ee, entry 1) and toluene (86.3% ee, entry 2) gave better enantioselectivities than in polar solvents (entry 4, MeOH, 80.8% ee; entry 5, acetone, 77.3% ee, entry 6, DMF, 77.4% ee, entry 7, THF, 80.6% ee). A small hydrogen pressure effect was found for this asymmetric catalytic system. Higher pressure gave slightly better enantioselectivities and reactivities, e.g., 86.3% ee under 40 psi of hydrogen (entry 8) vs. 80.2% ee under 14.7 psi (entry 9). However, increasing hydrogen pressure further did not provide any improvement in the enantioselectivity. A neutral rhodium catalyst formed in situ from BICP and [Rh(COD)Cl]₂ was much less effective than the cationic Rh species (entry 11, 11.4% ee vs. entry 8, 86.3% ee). Under similar conditions, hydrogenation of enamide 31a proceeded with low conversion giving only 11.4% enantiomeric excess

30

(entry 11). Overall, the optimized conditions use the catalyst generated in situ from [Rh(COD)₂]BF₄ or [Rh(COO)₂]OTf (1.0 mol %) and BICP (1.2 mol %) and the reaction is carried out at room temperature in toluene under 40 psi H₂.

TABLE 1

Rhodium Catalyzed Asymmetric Hydrogenation of Enamide 31a[a]

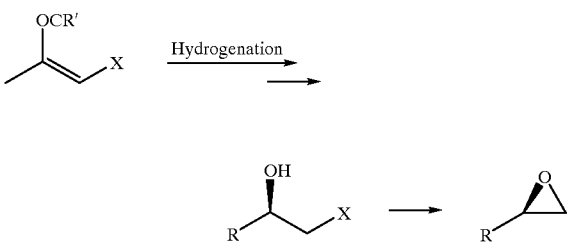

| Entry | Solvent | Pressure (psi) | Ee (%)[c] |
|---|---|---|---|
| 1 | Benzene | 40 | 85.2 |
| 2 | Toluene | 40 | 86.3 |
| 3 | CH₂Cl₂ | 40 | 75.7 |
| 4 | MeOH | 40 | 80.8 |
| 5 | Acetone | 40 | 77.3 |
| 6 | DMF | 40 | 77.4 |
| 7 | THF | 40 | 80.6 |
| 8[d] | Toluene | 40 | 86.3 |
| 9 | Toluene | 14.7 | 80.2 |
| 10 | Benzene | 147 | 84.9 |
| 11[e] | Toluene | 40 | 11.4 |

[a]The reaction was carried out at room temperature under an initial hydrogen pressure of 1 to 10 atm for 24 h. The catalyst was made in situ by stirring a solution of [Rh(COD)₂]BF₄ and the ligand in toluene {[substrate (0.5 mmol, 0.125 M)]/[Rh]/(R,R)-BICP = 1:0.01:0.011]}. The reaction went in quantitative yield.
[b]R-configuration was assigned by comparison of optical rotation with reported data.
[c]Enantiomeric excesses were determined by chiral GC using a Supelco Chiral Select 1000 column at 130° C.
[d][Rh(COD)₂]Otf was used as catalyst precursor.
[e][Rh(COD)₂] was used as catalyst precursor.

The scope of the asymmetric hydrogenation reaction with different substrates is shown in Table 2. A series of α-arylenamides were reduced to give the enantiomerically enriched α-arylethyl amine derivatives with good enantioselectivities using the optimal reaction conditions. Only a small electronic effect of the aryl ring was observed on the enantioselectivity. For example, 4'-methylphenyl substituted and 4'-trifluoromethylphenyl substituted enamides 31b (entry 2) and 31d (entry 4) gave similar results with enamide 31a (entry 1), while 4'-methoxyphenyl substituted enamide 31f gave better enantioselectivity (entry 6). Increasing the steric bulk of the group on the 4'-position on the phenyl ring of the enamide gave slightly better enantioselectivities. For example, 4'-phenylphenyl substituted enamide 31e (entry 5) was hydrogenated in high yield with 93.0% ee compared to phenyl enamide 1a (86.3% ee, entry 1).

TABLE 2

Asymmetric Hydrogenation of Enamides by a Cationic Rhodium-(R,R)-BICP Complex[a]

![reaction scheme: (Z)-31 and (E)-31 enamides Ar-C(=CHR)-NHAc hydrogenated with [Rh(COD)₂]OTf (1 mol%) + (R,R)-BICP (1.1 mol%), H₂ (40 psi), Toluene, 24 hr, rt, to give (R)-32a[b]]

| Entry | 31[c] | Ar | R | ee (%)[d] |
|---|---|---|---|---|
| 1 | 31a | $C_6H_5$ | H | 86.3 |
| 2 | 31b | 4-Me—$C_6H_4$ | H | 86.1 |
| 3 | 31c | 3-Me—$C_6H_4$ | H | 85.7 |
| 4 | 31d | 4-$CF_3$—$C_6H_4$ | H | 86.4 |
| 5 | 31e | 4-Ph—$C_6H_4$ | H | 93.0 |
| 6 | 31f | 4-MeO—$C_6H_4$ | H | 91.6 |
| 7 | 31g | 2-Naphthyl | H | 85.2 |
| 8 | 31h | $C_6H_5$ | $CH_3$ | 95.0 |
| 9 | 31i | $C_6H_5$ | $CH(CH_3)_2$ | 93.5 |
| 10 | 31j | $C_6H_5$ | $CH_2Ph$ | 90.5 |
| 11 | 31k | 4-MeO—$C_6H_4$ | $CH_3$ | 95.2 |
| 12 | 31l | 4-$CF_3$—$C_6H_4$ | $CH_3$ | 95.1 |
| 13 | 31m | 2-Naphthyl | $CH_3$ | 93.6 |

[a]The reaction was carried out at room temperature under an initial hydrogen pressure of 40 psi for 24–36 h. The catalyst was made in situ by stirring a solution of [Rh(COD)₂]Otf and (R,R)-BICP in toluene {[substrate (0.5 mmol, 0.125 M)]/[Rh]/(R,R)-BICP = 1:0.01:0.011]}. The reaction went in quantitative yield.
[b]R-configuration was assigned by comparison of optical rotation with reported data.
[c]Enamides 31 were prepared according to literature methods or by reduction of corresponding oximes by iron powder in the presence of acetic anhydride in DMF.
[d]Enantiomeric excesses were determined by chiral GC using a Supelco Chiral Select 1000 column or by Chiral HPLC with a Regis (R,R)-Whelk-O1 column.

An important feature of the Rh-BICP catalyst was found when we extended this hydrogenation reaction to an α-arylenamide with a β-methyl group, 31h. The catalyst system can hydrogenate this β-substituted enamide effectively and gave higher enantioselectivity than the corresponding terminal amide substrate 31a. The hydrogenation reaction was not sensitive to the geometry of the substrates, as an isomeric mixture of (Z)- and (E)-enamides with a ratio of 1:2 was reduced smoothly in 95% ee under the standard reaction conditions. The ability to reduce such β-substituted enamides greatly expands the utility of this hydrogenation methodology for the synthesis of various chiral amine derivatives. These amine derivatives are useful building blocks for biologically active compounds. Because it is currently difficult to synthesize isomerically pure enamides using existing methods (T. Morimoto, et al., Chem. Pharm. Bull. 1992, 40, 2894; H. B. Kagan, et al., J. Organomet. Chem. 1975, 90, 353; D. Sinou, et al., J. Organomet. Chem. 1976, 114, 325; G. R. Lenz, Synthesis, 1978, 489; D. M. Tschen, et al., J. Org. Chem. 1995, 50, 4321), this insensitivity to the isomeric composition of enamides should be critical for the practical synthesis of chiral amines.

A series of different β-substituted isomeric enamide mixtures (31h–31j) and β-methyl substituted enamides with various substituents on the 1-aryl group (31k–31l) can be reduced in high yield with high enantioselectivities. The reaction is not sensitive to electronic effects of a substituent on the 1-aryl group. For example, the 4-methoxyphenyl-substituted species 31k and the 4-trifluoromethylphenyl analog 31l showed almost the same reactivities and enantioselectivities under identical hydrogenation conditions (entries 11 and 12). The enantioselectivities achieved in the Rh-BICP system are comparable to the results obtained with Burk's Rh-DuPhos catalysts, the only previously reported system that can tolerate (Z)- and (E)-mixtures of simple enamides.

Cyclic Enamides

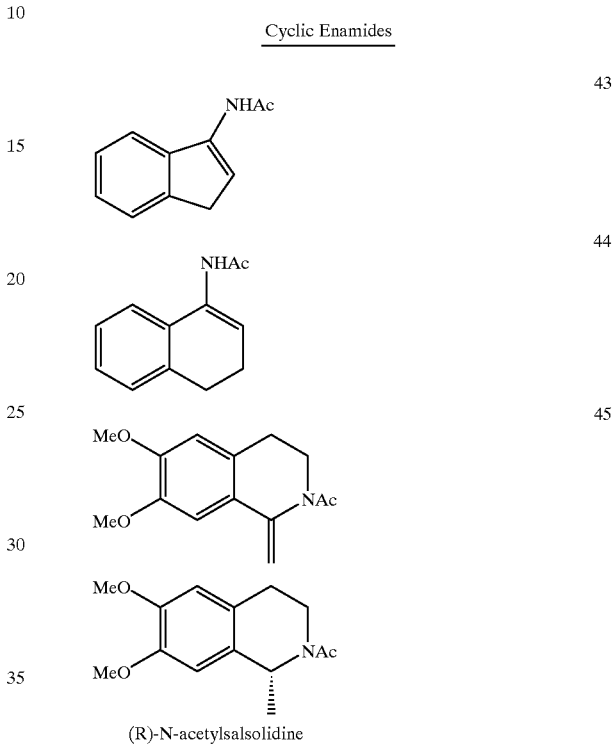

(R)-N-acetylsalsolidine

To further expand the utility of this asymmetric enamide hydrogenation, we have examined our catalytic system with some cyclic enamides. The successful reduction of these cyclic enamide substrates can lead to important chiral amines (Y. Kohmura, et al., Synlett 1997, 1456) e.g., tetrahydroisoquinolines (R. Noyori, etal., J. Am. Chem. Soc. 1986,108, 7117; M. Kitamura, et al., Bull.Chem. Soc. Jpn. 1996, 69, 1695; M. Kitamura, et al., J. Org. Chem. 1994, 59, 297). Under the standard reaction conditions used for acyclic enamide substrates, hydrogenation of cyclic enamides 43 and 44 showed high reactivity, giving the corresponding N-acetyl-amine with moderate enantioselectivity (60.3% ee for 43 and 64.5% ee for 44). Asymmetric hydrogenation of N-acetyl-1-methylene-1,2,3,4-tetrahydroisoquinoline 45 proceeded smoothly affording (R)-(–)-N-acetyl-salsolidine (T. Morimoto, et al., Tetrahedron: Asymmetry 1995, 6, 75; b) Z. Czarnocki, et al., Heterocycles 1992, 34, 943; M. J. Munchhof, et al., J. Org. Chem. 1995, 60, 7086) in quantitative yield in 77.8% ee.

In summary, the BICP ligand is one of the best chiral diphenylphosphino ligands for the rhodium-catalyzed asymmetric hydrogenation of electron-rich olefin substrates. This method provides an efficient approach to a wide range of enantiomerically enriched arylalkyl amines. An advantage of this catalytic system is that the enantioselectivity of the hydrogenation reaction is not sensitive to the geometry of the starting enamides. Thus a series of (Z)- and (E)-β-substituted amide isomers can be reduced in high yield and with high enantioselectivity.

General Procedures

All reactions and manipulations were performed in a nitrogen-filled glove box or using standard Schlenk techniques. Toluene, benzene and tetrahydrofuran (THF) were distilled from sodium benzophenone ketyl under nitrogen. Methylene chloride and 1,2-dichloroethane were distilled from $CaH_2$. Methanol, ethanol, and 2-propanol were distilled from Mg under nitrogen. The chiral (R,R)-BICP ligand was prepared as described above. (R)-BINAP, (+)-DIOP were purchased from Aldrich. (R,R)-Me-DuPhos and (R,R)-Et-DuPhos were purchased from Strem. All enamide substrates were prepared following the reported procedure or by reduction of corresponding oxime by iron in the presence of acetic anhydride in DMF. Column chromatography was performed using EM Silica gel 60 (230–400 mesh). $^1H$, $^{13}C$ and $^{31}P$ NMR were recorded on Bruker WP-200, AM-300, WM-360 and AMX-360 spectrometers. Chemical shifts are reported in ppm downfield from tetramethylsilane with the solvent resonance as the internal standard. Optical rotation was obtained on a Perkin-Elmer 241 polarimeter. MS spectra were recorded on a KRATOS mass spectrometer MS 9/50 for LR-El and HR-El. GC analysis was carried out on Hewlett-Packard 5890 and 6890 gas chromatograph using chiral capillary column: Chiral Select 1000 column {Dimensions: 15 m×0.25 mm (i.d.). Carrier gas: He (1 mL/min)}. HPLC analysis was carried out on a Waters™ 600 chromatograph with an (R,R)-Poly Whelk-01 column from Regis Technologies, Inc. {Particle size: 5.0 um. Column dimensions: 25 cm (length)×0.46 cm (i.d.), Column temperature: 25° C}.

Asymmetric Hydrogenation

In a glove box, to a solution of $[Rh(COD)_2]BF_4$ (5.0 mg, 0.012 mmol) in toluene (10 mL) was added (R,R)-BICP (0.15 mL of 0.1 M solution in toluene, 0.015 mmol). After stirring the mixture for 30 min, substrate enamide (1.2 mmol) was added. The hydrogenation was performed at room temperature under 40 psi of hydrogen for 24 h. After the hydrogen was released, the reaction mixture was passed through a short silica gel column to remove the catalyst. The enantiomeric excess was measured by capillary GC or HPLC directly without any further purification. The absolute configuration of product was determined by comparing the observed rotation with the reported value.

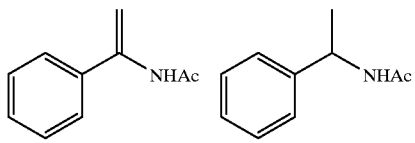

N-Acetyl-1-phenylethenamine. $^1H$ NMR (360 MHz, $CDCl_3$) δ 2.13 (br, 3H), 5.09 (s, 1H), 5.88 (s, 1H), 6.85 (br, 1H), 7.43~7.21 (m, 5H).

N-Acetyl-1-phenylethylamine. $^1H$ NMR (360 MHz, $CDCl_3$) δ 1.47 (d, J=6.93 Hz, 3H), 1.95 (s, 3H), 5.08 (m, 1H), 6.05 (br, 1H), 7.21~7.33 (m, 5H).

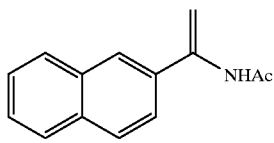

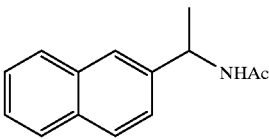

N-Acetyl-1-(2-naphthyl)-ethenamine. $^1H$ NMR (360 MHz, $CDCl_3$) δ 2.15 (s, 3H), 5.24 (s, 1H), 5.94 (s, 1H), 7.03 (br, 1H), 7.49~7.55 (m, 3H), 7.80~7.87 (m, 4H).

N-Acetyl-1-(2-naphthyl)ethylamine. $^1H$ NMR (200 MHz, $CDCl_3$) δ 1.57 (d, J=6.90 Hz, 3H), 2.00 (s, 3H), 5.26~5.33 (m, 1H), 6.00 (br, 1H), 7.40~7.51 (m, 3H), 7.75~7.83 (m, 4H).

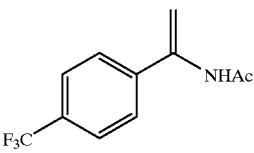

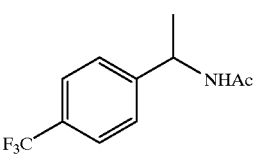

N-Acetyl-1-(4-trifluoromethylphenyl)-ethenamine. $^1H$ NMR (200 MHz, $CDCl_3$) δ 2.11 (s, 3H), 5.16 (s, 1H), 5.82 (s,1H), 6.98 (br, 1H), 7.50–7.64 (m, 4H).

N-Acetyl-1-(4-trifluoromethylphenyl)ethylamine. $^1H$ NMR (200 MHz, $CDCl_3$) δ 1.49 (d, J=6.98 Hz, 3H), 2.00. (s, 3H), 5.16 (m, 1H), 5.76 (br, 1H), 7.42 (d, J=8.16 Hz, 2H), 7.59 (d, J=8.4 Hz, 2H).

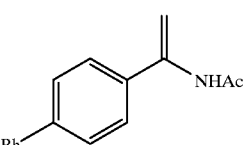

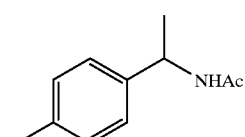

N-Acetyl-1-(4-phenylphenyl)-ethenamine. $^1H$ NMR (360 MHz, acetone-d6) δ 2.35 (s, 3H), 5.27 (s, 1H), 6.09 (s, 1H), 7.60~7.91 (m, 9H), 8.80 (br, 1H); $^{13}C$ NMR (acetone-d6): δ 24.6, 101.9, 128.05, 128.1, 128.8, 130.2, 139.0, 141.6, 142.2, 142.9, 170.1; MS m/z: 237, 221, 180, 152, 78, 63, 43; HRMS calcd for $C_{16}H_{15}NO$ (M+): 237.1154; found: 237.1143.

N-Acetyl-1-(4-phenylphenyl)ethylamine. $^1H$ NMR (360 MHz, $CDCl_3$) δ 1.53 (d, J=6.90 Hz, 3H), 2.01 (s, 3H), 5.18 (m, 1H), 5.67 (br, 1H), 7.32~7.46 (m, 5H), 7.55~7.58 (m, 4H); $^{13}C$ NMR δ 21.7, 23.5, 48.5, 126.6, 127.1, 127.3, 127.4, 128.8, 140.4, 140.7, 142.1, 169.1; MS m/z: 239, 224, 196, 182, 165, 155, 120, 77, 43; HRMS calcd for $C_{16}H_{17}NO$ ($M^+$): 239.1310; found: 239.1303

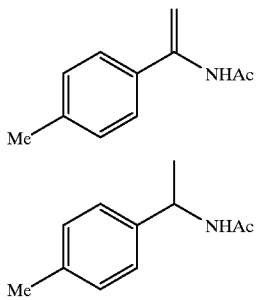

N-Acetyl-1-(4-methylphenyl)-ethenamine. $^1$H NMR (360 MHz, CDCl$_3$) δ 2.13 (s, 3H), 2.36 (s, 3H), 5.05 (s, 1H), 5.83 (s, 1H), 6.80 (br, 1H), 7.17 (d, J=8.1 Hz, 2H), 7.31 (d, J=7.53 Hz, 2H).

N-Acetyl-1-tolylethylamine. $^1$H NMR (360 MHz, CDCl$_3$) δ 1.45 (d, J=6.94 Hz, 3H), 1.94 (s, 3H), 2.34 (s, 3H), 5.04 (m, 1H), 6.06 (br, 1H), 7.12 (d, J=8.08 Hz, 2H), 7.23 (d, J=8.10 Hz, 2H).

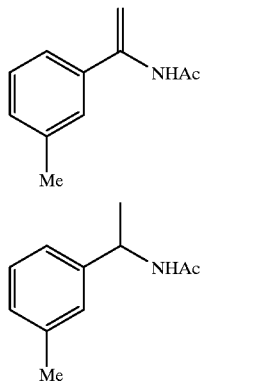

N-Acetyl-1-(3-methylphenyl)-ethenamine. $^1$H NMR (360 MHz, CDCl$_3$) δ 2.12 (s, 3H0, 2.37 (s, 3H), 5.06 (s, 1H), 5.85 (s, 1H), 6.89 (br, 1H), 7.27~7.15 (m, 4H).

N-Acetyl-1-(3-methylphenyl)ethylamine. $^1$H NMR (360 MHz, CDCl$_3$) δ 1.47 (d, J=6.88 Hz, 3H), 1.97 (s, 3H), 2.35 (s, 3H), 5.08 (m, 1H), 5.77 (br, 1H), 7.07~7.11 (m, 3H), 7.23~7.26 (m, 1H).

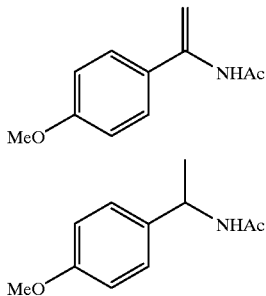

N-Acetyl-1-(4-methoxyphenyl)-ethenamine. $^1$H NMR (360 MHz, CDCl$_3$) δ 2.13 (s, 3H), 3.82 (s, 3H), 5.01 (s, 1H), 5.77 (s, 1H), 6.75 (br, 1H), 6.89 (d, J=8.80 Hz, 2H), 7.35 (d, J=8.50 Hz, 2H).

N-Acetyl-1-(4-methoxyphenyl)ethylamine. $^1$H NMR (360 MHz, CDCl$_3$) δ 1.47 (m, 3H), 1.96 (s, 3H), 2.03 (s, 3H), 5.08 (m, 1H), 5.07 (br, 1H), 6.84~6.88 (m, 2H)7.22~7.26 (m, 2H). ,

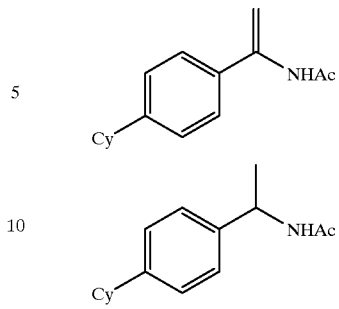

N-Acetyl-1-(4-cyclohexylphenyl)-ethenamine. $^1$H NMR (360 MHz, CDCl$_3$) δ 1.54~2.05 (m, 13H), 2.66 (m, 1H), 5.17 (s, 1H), 5.80 (s, 1H), 7.32 (d, J=7.70 Hz, 2H), 7.47 (d, J=7.80 Hz, 2H), 8.11 (br,1H). $^{13}$C NMR (CDCl$_3$) δ 24.3, 26.5, 27.3, 34.8, 44.7, 102.6, 126.6, 127.3, 136.2, 141.4, 148.8, 170.3. MS m/z: 243, 228, 201, 186, 160, 145, 130, 117, 104, 91, 77, 55, 43; HRMS calcd for C$_{16}$H$_{21}$NO (M+): 243.1623; found: 243.1616.

N-Acetyl-1-(4cyclohexylphenyl)-ethylamine. $^1$H NMR (300 MHz, CDCl$_3$) δ 1.25~1.46 (m, 5H), 1.45 (d, J=6.84 Hz, 3H), 1.72~1.92 (m, 5H), 1.92 (s, 3H), 2.47 (m, 1H), 5.07 (m, 1H), 6.20 (m, 1H), 7.14~7.24 (m, 4H); $^{13}$C NMR δ 21.9, 23.8, 26.5, 27.3, 34.8, 44.6, 49.0, 126.6, 127.5, 140.8, 147.7, 269.5; MS m/z: 245, 230, 202, 188, 162, 143, 130, 106, 43; HRMS calcd for C$_{16}$H$_{23}$NO (M$^+$): 245.1780; found: 245.1779.

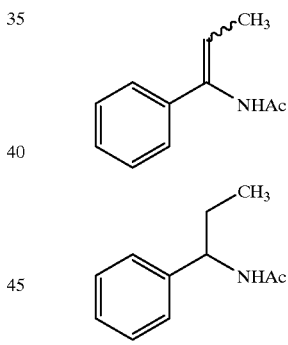

N-Acetyl-1-phenylpropenamine. Z-E isomers (1:2.05) $^1$H NMR (360 MHz, CDCl$_3$) δ (major isomer) 1.70 (d, J=7.34 Hz, 3H), 2.18 (s, 3H), 5.95 (q, J=6.94 Hz, 1H), 6.59 (br, 1H), 7.25~7.45 (m, 5H); δ (minor isomer) 1.86 (d, J=7.02 Hz, 3H), 2.05 (s, 3H), 6.05 (q, J=7.00 Hz, 1H), 6.65 (br, 1H).

N-Acetyl-1-phenylpropylamine. $^1$H NMR (360 MHz, CDCl$_3$) δ 0.88 (t, J=7.41 Hz, 3H), 1.84 (m, 2H), 1.98 (s, 3H), 4.88 (m, 1H), 5.68 (br, 1H), 7.23~7.36 (m, 5H).

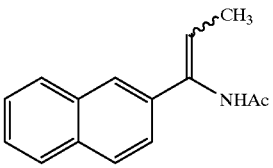

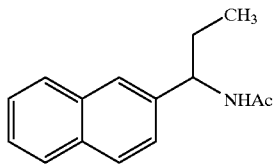

N-Acetyl-1-(2-Naphthyl)-propenamine. Z-E isomers $^1$H NMR (360 MHz, CDCl$_3$) δ (major isomer) 1.82 (d, J=6.97 Hz, 3H), 2.23 (s, 3H), 6.11 (q, J=6.95 Hz, 1H), 6.92 (br, 1H), 7.46~7.86 (m, 7H); δ (minor isomer) 1.92 (d, J=6.96 Hz, 3H), 1.86 (s, 3H), 6.23 (q, J=6.99 Hz, 1H), 6.80 (br, 1H).

N-Acetyl-1-(2-Naphthylpropylamine. $^1$H NMR (300 MHz, CDCl$_3$) δ 0.92 (t, J=7.41 hz, 3H), 1.87~1.97 (m, 2H), 2.00 (s, 3H), 5.04 (m, 1H), 5.84 (br, 1H), 7.26~7.47 (, 3H), 7.73 (s, 1H), 7.80~7.83 (m, 3H).

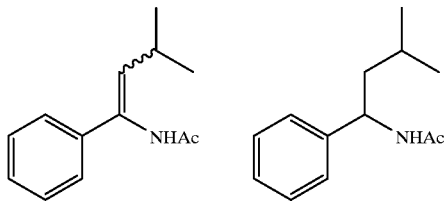

N-Acetyl-1-phenyl-3-methylbutenamine. Z-E isomers (1.53:1) $^1$H NMR (360 MHz, CDCl$_3$) δ (major isomer): 1.08 (d, J=6.63 Hz, 6H), 2.17 (s, 3H), 2.53~2.65 (m, 1H), 5.71 (d, J=9.64 Hz, 1H), 6.58 (br, 1H), 7.25~7.45 (m, 5H); δ (minor isomer) 1.70 (s, 3H), 2.80 (m, 1H), 5.77 (d, J=9.70 Hz, 1H), 5.65 (br, 1H).

N-Acetyl-1-phenyl-3-methylbutylamine. $^1$H NMR (360 MHz, CDCl$_3$) δ 0.91~0.95 (m, 6H), 1.50~1.71 (m, 3H), 2.04 (s, 3H), 5.04 (m, 1H), 5.63 (br, 1H), 7.23~7.35 (m, 5H).

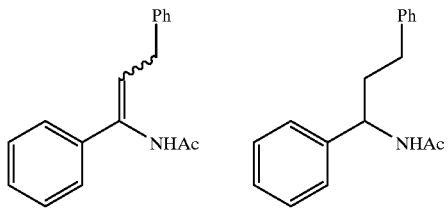

N-Acetyl-1,3-diphenylpropenamine. Z-E isomer (2.61:1) $^1$H NMR (360 MHz, CDCl$_3$) δ (major isomer): 1.81 (s, 6H), 3.52 (d, J=7.06 Hz, 2H), 6.00 (t, J=7.07 Hz, 1H), 6.69 (br, 1H), 7.21~7.48 (m, 10H); δ (minor isomer) 1.81 (s, 3H), 3.60 (d, J=7.33 Hz, 2H), 6.16 (m, 1H).

N-Acetyl-1,3-diphenylpropylamine. $^1$H NMR (360 MHz, CDCl$_3$) δ 1.95 (s, 3H), 2.13~2.19 (m, 2H), 2.57~2.60 (m, 2H), 5.03 (m, 1H), 5.80 (br, 1H), 7.14~7.35 (m, 10H).

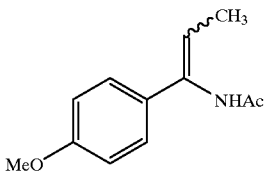

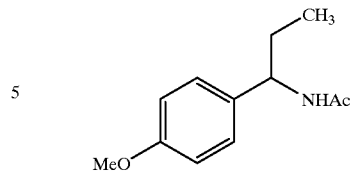

N-Acetyl-1-(3-methoxyphenyl)-propenamine Z-E isomer. (1.8:1) $^1$H NMR (360 MHz, CDCl$_3$) δ (major isomer): 1.69 (d, J=7.43 Hz, 3H), 2.18 (s, 3H), 3.80 (s, 1H), 5.84 (q, J=7.00 Hz, 1H), 6.56 (br, 1H), 6.83~6.94 (m, 2H), 7.26~7.37 (m, 2H); δ (minor isomer) 1.75 (d, 3H), 1.74 (s, 3H), 3.82 (s, 3H), 5.91 (q, 1H), 6.60 (br, 1H). $^{13}$C NMR (major isomer): 14.0, 23.1, 55.3, 1113.7, 119.1, 126.6, 130.1, 130.9, 133.9, 159.2, 169.1; minor isomer, 13.6, 20.5, 55.4, 114.2, 120.3, 126.7, 130.3, 130.8, 135.3, 159.7, 173.8; MS m/z: 205, 190, 162, 134, 119, 91, 77, 43; HRMS calcd for C$_{12}$H$_{15}$NO$_2$ (M+): 205.1103; found: 205.1095.

N-Acetyl-1-(4-methoxyphenyl)-propylamine. $^1$H NMR (360 MHz, CDCl$_3$) δ 0.85 (t, J=7.40 Hz, 3H), 1.73~1.88 (m, 2H), 2.04 (s, 3H), 3.78 (s, 3H), 4.82 (m, 1H), 5.95 (d, J=8.08 Hz, 1H), 6.83~6.87 (m, 2H), 7.17~7.26 (m, 2H); $^{13}$C NMR δ 10.7, 23.4, 28.9, 54.4, 55.2, 114.0, 127.8, 134.2, 158.7, 169.1; MS m/z: 207, 178, 164, 148, 136, 121, 109, 91, 77, 65, 56, 43; HRMS calcd for C$_{12}$H$_{17}$NO$_2$ (M$^+$): 207.1259; found: 207.1249

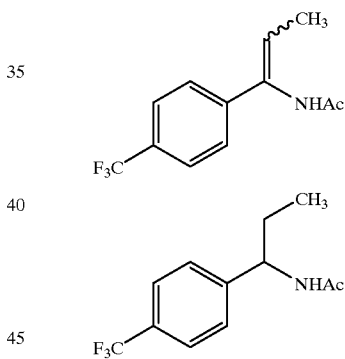

N-Acetyl-1-(4-trifluoromethylphenyl)-propenamine Z-E isomer. (3.28:1) $^1$H NMR (360 Hz, CDCl$_3$) δ (major isomer): 1.80 (d, J=6.92 Hz, 3H), 2.18 (s, 3H), 6.00 (q, J=7.00 Hz, 1H), 6.70 (br, 1H), 7.45~7.60 (m, 4H); δ (minor isomer) 1.89 (d, J=6.79 Hz, 3H), 1.80 (s, 3H), 6.18 (m, 1H), 6.70 (br, 1H). $^{13}$C NMR (major isomer): δ 14.0, 23.1, 55.3, 113.7, 119.1, 126.6, 130.1, 130.9, 133.9, 159.2, 169.1; minor isomer, 13.6, 20.5, 55.4, 114.2, 120.3, 126.7, 130.3, 130.8, 135.3, 159.7, 173.8; MS m/z: 243, 200, 172, 132, 56,43; HRMS calcd for C$_{12}$H$_{12}$F$_3$NO (M+): 243.0871; found: 243.0864.

N-Acetyl-1-(4-trifluoromethylphenyl)-propylamine. $^1$H NMR (360 MHz, CDCl$_3$) δ 0.86 (t, J=7.43 Hz, 3H), 1.73 (m, 2H), 1.93 (s, 3H), 4.83 (m, 1H), 6.75 (d, J=7.92 Hz, 1H), 7.34 (d, J=8.26 Hz, 2H), 7.52 (d, J=8.11 Hz, 2H); $^{13}$C NMR δ 10.6, 23.0, 29.0, 54.8, 119.6~129.8 (m), 146.7, 169.8; MS m/z: 245, 216, 202, 188, 174, 159, 127, 117, 58, 43; HRMS calcd for C$_{12}$H$_{14}$F$_3$NO (M+): 245.1027; found: 245.1025.

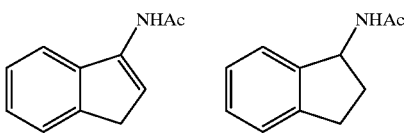

1-(N-Acetylamido)-indene. (3) Under stirring, to a solution of oxime of 1-Indanone (2.64 g 20 mmol) and acetic anhydride (15 mL) in DMF (50 mL) was added iron powder (10.0 g), then the reaction was initiated by adding few drops of chlorotrimethylsilane under nitrogen. After the reaction mixture was stirred at room temperature for 4 hrs, TLC showed that the reaction was complete. The reaction mixture was diluted with ether, and solid was filtered off through a short column of celite. The filtrate was concentrated and the residue was purified by flash chromatography on silica gel. Further recrystallization from $CH_2Cl_2$-Hexanes afforded pure enamide 3: 2.5 g, 72.2% yield. $^1$H NMR (360 MHz, $CD_3COCD_3$) δ 2.13 (s, 3H), 3.37 (m, 2H), 6.85 (m, 1H), 7.21~7.27 (m, 2H), 7.45~7.47 (m, 1H), 7.60 (d, J=7.36 Hz, 1H), 9.10 (br, 1H); $^{13}$C NMR ($CD_3COCD_3$) δ 23.7, 36.8, 114.5, 118.1, 124.7, 125.9, 126.7, 137.6, 14.1.1, 143.6, 169.2. MS m/z: 173, 132, 103, 77, 43; HRMS calcd for $C_{11}H_{11}NO$ ($M^+$): 173.0841; found: 173.0832.

1-(N-Acetylamido)-Indane. $^1$H NMR (300 MHz, $CDCl_3$) δ 1.62 (m, 1H), 2.03 (s, 3H); 2.59 (m, 1H), 2.86~2.98 (m, 2H), 5.47 (m, 1H), 5.70 (br, 1H), 7.22~7.30 (m, 4H).

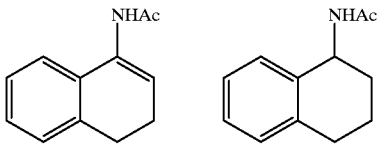

N-(3,4-Dihydro-1-Naphthyl)-Acetamide. $^1$H NMR (360 MHz, $CD_3COCD_3$) δ 1.98 (s, 3H), 2.20 (m, 2H), 2.64 (m, 2H), 6.32 (m, 1H), 7.07 (m, 3H), 7.22 (m, 1H), 8.53 (br, 1H); $^{13}$C NMR ($CD_3COCD_3$) δ 22.9, 23.8, 28.4, 118.7, 122.6, 127.1, 128.1, 128.4, 133.6, 137.6, 169.6. MS m/z: 187, 173, 144, 130, 115, 103, 91, 77, 65, 54, 43: HRMS calcd for $C_{12}H_{13}NO$ ($M^+$): 187.0997; found: 187.0993.

N-(1,2,3,4-Tetrahydro-1-Naphthyl)-Acetamide. $^1$H NMR (330 MHz, $CDCl_3$) δ 1.81 (s, 3H), 1.90 (~2.05 (m, 4H), 2.75~2.79 (m, 2H), 5.17 (m, 1H), 5.71 (br, 1H), 7.08~7.29 (m, 4H).

Determination of Enantiomeric Excess
1. Chiral Capillary GC

Column: b-DEX-390 column. Dimensions: 15 m×0.25 mm (i.d.). Carrier gas: He (1 mL/min). The racemic products were obtained by hydrogenation of substrates with an achiral catalyst. The following is the retention time for the racemic products.

N-Acetyl-1-phenylethylamine: (capillary GC, 130° C., isothermal) (S) $t_1$=27.6 min, (R) $t_2$=29.3 min.

N-Acetyl-1-(4-trifluoromethylphenyl)-ethylamine: (capillary GC, 150° C., isothermal) (S) $t_1$=14.0 min, (R) $t_2$=14.8 min.

N-Acetyl-1-(4-cyclohexylphenyl)-ethylamine: (capillary GC, 180° C., isothermal) (S) $t_1$=60.6 min, (R) $t_2$=61.8 min.

N-Acetyl-1-tolylethylamine: (capillary GC, 140° C., isothermal) (S) $t_1$=27.8 min, (R) $t_2$=28.9 min.

N-Acetyl-1-(3-methylphenyl)-ethylamine: (capillary GC, 140° C., isothermal) (S) $t_1$=23.4 min, (R) $t_2$=24.6 min.

N-Acetyl-1-(4-methoxyphenyl)ethylamine: (capillary GC, 140° C. for 60 min then 20° C./min to 180° C., gradient) (S) $t_1$=62.8 min, (R) $t_2$=63.2 min.

N-Acetyl-1-phenylpropylamine: (capillary GC, 135° C., isothermal) S) $t_1$=26.0 min, (R) $t_2$=27.1 min.

N-Acetyl-1-phenyl-3-methylbutylamine: (capillary GC, 145° C., isothermal) (S) $t_1$=26.2 min, (R) $t_2$=27.1 min.

N-Acetyl-1-(4-trifluoromethylphenyl)-propylamine: (capillary GC, 150° C., isothermal) (S) $t_1$=17.7 min, (R) $t_2$=18.5 min.

1-(N-Acetylamido)-indane (capillary GC, 160° C., isothermal) (S) $t_1$=17.9 min, (R) $t_2$=18.7 min.

N-(1,2,3,4-Tetrahydro-1-naphthyl)-acetamide (capillary GC, 180° C., isothermal) (S) $t_1$=10.1 min, (R) $t_2$=11.4 min.

N-Acetyl-1-phenylbutylamine: (capillary GC, 150° C. isothermal) (S) $t_1$=14.8 min, (R) $t_2$=15.4 min.

N-Acetyl-1-(2-furyl)ethylamine: (capillary GC, 140° C., isothermal) (S) $t_1$=5.7 min, (R) $t_2$=5.9 min.

N-Acetyl-1-(2-thienyl)ethylamine: (capillary GC, 140° C., isothermal) (S) $t_1$=16.0 min, (R) $t_2$=16.7 min.

2. Chiral HPLC

Column: (R,R)-Poly Whelk-O from Regis Technologies, Inc. Particle size: 5.0 um. Column dimensions: 25 cm (length)×0.46 cm (i.d.). Column temperature: 25° C.

N-Acetyl-1-(2-naphthyl)ethylamine: (HPLC, 1.0 mL/min, 2-PrOH/hexane=1), (S) $t_1$=10.2 min, (R) $t_2$=60.7 min.

N-Acetyl-1-(1-naphthyl)ethylamine: (HPLC, 1.0 mL/min, 2-PrOH/hexane=1), (S) $t_1$=9.4 min, (R) $t_2$=29.9 min.

N-Acetyl-1-(4-phenylphenyl)ethylamine: (HPLC, 1.0 mL/min, 2-PrOH/hexane=1), (S) $t_1$=8.6 min, (R) $t_2$=18.5 min.

N-Acetyl-1-(2-naphthylypropylamine: (HPLC, 1.0 mL/min, 2-PrOH/hexane=1), (S) $t_1$=9.6 min, (R) $t_2$=39.8 min.

N-Acetyl-1,3-diphenylpropylamine: (HPLC, 1.0 mL/min, 2-PrOH/hexane=7:3), (S) $t_1$=9.2 min, (R) $t_2$=13.5 min.

N-Acetyl-1-(4-methoxyphenyl)-propylamine: (HPLC, 1.0 mL/min, 2-PrOH/hexane=7:3), (S) $t_1$=10.7 min, (R) $t_2$=22.8 min.

Example 2. Hydrogenation of Enamides to β-Amino Acids
A. Synthesis of Substrates:

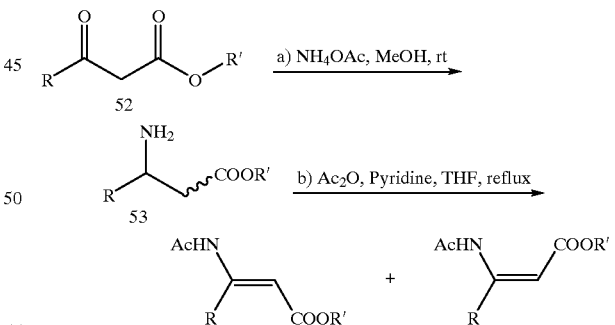

Step a: A solution of β-keto ester 52 (12 mmol) and $NH_4OAc$ (4.6 g, 60 mmol) in MeOH (15 mL) was stirred at room temperature for 3 days. After the solvent was evaporated under reduced pressure, the was treated by chloroform (30 mL). The resulting solid was filtered off and, washed with chloroform (2×30 mL). The combined filtrate was washed with water and brine. After dried over sodium sulfate, evaporation of the solvent gave 3-amino-2-alkenoate 53, which was used for the next step.

Step b: To a solution of 3-amino-2-alkenoate 53 in THF (12 mL) was added pyridine (2 mL) and acetic anhydride (6 mL). The reaction mixture was then heated under reflux for 24 h. After cooled to room temperature, the volatiles were evaporated. The residue was dissolved in EtOAc (20 mL), and the solution was washed with water (10 mL), 1N HCl (10 mL), 1M $KH_2PO_4$ (10 mL), $NaHCO_3$ (sat. 10 mL), and brine (15 mL). After drying over sodium sulfate, the solvent was evaporated under reduced pressure. Chromatography of the residue on silica gel with a gradient solvent of EtOAc in Hexanes (15% to 70%) as eluent. Z-isomer was eluted first, followed by a by-product. Then E-isomer was eluted last.

B. General Procedure for Asymmetric Hydrogenation.

To a solution of $[Rh(COD)_2]OTf$ (2.0 mg, 4.27×10-3 mmol) in toluene (3.4 mL) in a glovebox was added a chiral ligand (0.047 mL of 0.1 M solution in toluene, 4.7×10-3 mmol). After the mixture was stirred for 30 min, substrate 1 (0.427 mmol) was added. The hydrogenation was performed at room temperature under 10 atm of hydrogen for 24 hrs. The hydrogen pressure was released carefully and the reaction mixture was passed through a short silica gel column to remove the catalyst. The enantiomeric excesses were measured by GC without further purification.

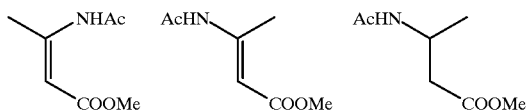

(Z)-Methyl 3-Acetamido-2-butenoate. $^1$H NMR (360 MHz, $CDCl_3$) δ 1.89 (s, 3H), 2.24 (s, 3H), 3.57 (s, 3H), 4.76 (s, 1H), 10.9 (br, 1H).

(E)-Methyl 3-Acetamido-2-butenoate. $^1$H NMR (360 MHz, Acetoned6) δ 2.02 (s, 3H), 2.29 (s, 3H), 3.58 (s, 3H), 6.85 (s, 1H), 8.72 (br, $_1$H).

(R)-Methyl 3-Acetamidobutanoate. $[α]_D^{25}$=+21.4 (c 1.4, MeOH); $^1$H NMR (360 MHz, $CDCl_3$) δ 1.16 (d, J=6.81 Hz, 3H), 1.90 (s, 3H), 2.47 (m, 3H), 3.63 (s, 3H), 4.28 (m, 1H), 6.14 (br, 1H).

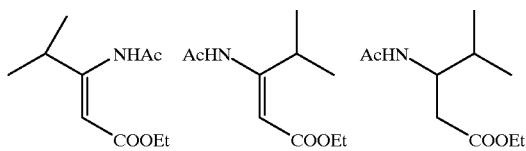

(Z)-Ethyl 4-Methyl-3-Acetamido-2-pentenoate. $^1$H NMR (360 MHz, $CDCl_3$) δ 1.10~1.24 (m, 6H), 1.25~1.30 (m, 3H), 2.13 (s, 3H), 3.87 (m, 1H), 4.13~4.19 (m, 2H), 5.04 (s, 1H), 11.10 (br, 1H). $^{13}$C NMR (90.5 MHz, $CDCl_3$) δ 13.9, 14.0, 21.0, 25.2, 29.0, 59.6, 92.4, 165.2, 168.0, 169.4. MS m/z: 199, 184, 156, 111, 96, 70, 43.

(E)-Ethyl 4-Methyl-3-Acetamido-2-pentenoate. $^1$H NMR (200 MHz, Acetone-d6) δ 1.12 (d, J=7.08 Hz, 6H), 1.20 (t, J=7.08 Hz, 3H), 2.08 (s, 3H), 4.05 (q, J=7.09 Hz, 2H), 4.30 (m, 1H), 6.97 (s, 1H), 8.14 (br, 1H). $^{13}$C NMR (50.3 MHz, Acetoned6) δ 14.5, 19.6, 24.6, 27.7, 59.4, 100.8, 158.7, 168.3, 170.6, MS m/z: 199, 184, 156, 113, 111, 96, 70, 43.

(S)-Ethyl 4-Methyl-3-Acetamidopentanoate. $[α]_D^{25}$+52.8 (c 1.2, $CHCl_3$); $^1$H NMR (360 MHz, $CDCl_3$) δ 0.83~0.86 (m, 6H), 1.15~1.20 (m, 3H), 1.75 (m, 1H), 1.90 (s, 3H), 2.40~2.43 (m, 2H), 4.00~4.08 (m, 3H), 639 (br, 1H). $^{13}$C NMR (90.5 MHz, $CDCl_3$) δ 13.9, 18.5, 19.0, 23.0, 31.3, 36.5, 51.3, 60.3, 169.4, 171.8, MS m/z: 202, 186, 158, 142, 116, 97, 70, 43.

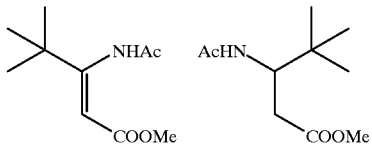

(Z)-Methyl 4,4-Dimethyl-3-Acetamido-2-pentenoate. $^1$H NMR (360 MHz, Acetone-d6) δ 1.18 (s, 9H), 2.01 (s, 3H), 3.60 (s, 3H), 5.52 (s, 1H), 8.80 (br, 1H). $^{13}$C NMR (90.5 MHz, Acetone-d6) δ 23.9, 28.3, 37.3, 50.9, 106.1, 158.5, 167.4, 168.3. MS m/z : 199, 184, 168, 153, 142, 126, 110, 68, 43.

Methyl 4,4-Dimethyl-3-Acetamidopentanoate. $^1$H NMR (200 MHz, $CDCl_3$) δ 0.78 (s, 9H), 1.79 (s, 3H), 2.06~2.18 (m, 1H), 2.36~2.45 (m, 1H), 3.46 (s, 3H), 4.05 (m, 1H), 6.60 (br, 1H). $^{13}$C NMR (50.3 MHz, $CDCl_3$) δ 22.6, 25.9, 34.3, 35.3, 51.3, 54.0, 169.7, 172.3 MS m/z: 201, 170, 144, 116, 102, 84, 70, 43.

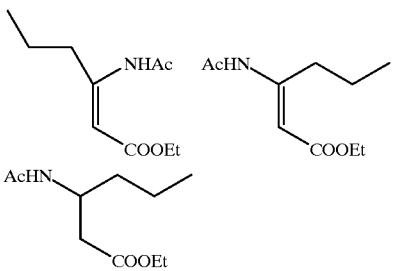

(Z)-Ethyl 3-Acetamido-2-hexenoate. $^1$H NMR (360 MHz, $CDCl_3$) δ 0.94 (t, J=7.39 Hz, 3H), 1.27 (t, J=7.11 Hz, 3H), 1.60 (m, 2H), 2.12 (s, 3H), 2.72 (t, J=? 2H), 4.13 (t, J=7.12 Hz, 2H), 4.92 (s, 1H), 11.10 (br, 1H). $^{13}$C NMR (90.5 MHz, $CDCl_3$) δ 13.4, 14.0, 21.3, 25.1, 35.8, 59.6, 95.7, 158.7, 168.1, 169.1, MS m/z: 199, 184, 170, 156, 129, 113, 96, 83, 43.

(Z)-Ethyl 3-Acetamido-2-hexenoate. $^1$H NMR (360 MHz, Acetone-d6) δ 1.15 (t, J=7.39 Hz, 3H), 1.44 (t, J=7.13 Hz, 3H), 1.53 (m, 2H), 2.28 (s, 3H), 2.95 (m, 2H), 4.30 (q, J=7.14 Hz, 2H), 7.14 (s, 1H), 8.91 (br, 1H). $^{13}$C NMR (90.6 MHz, Acetone-d6) δ 14.4, 15.1, 23.2, 25.1, 34.1, 59.9, 101.8, 155.4, 168.9, 170.8. MS m/z: 199, 184, 170, 156, 156, 129, 112, 96, 83, 43.

(R)-Ethyl 3-Acetamidohexanoate. $D^{25}$ =+42.8 (c1.86, $CHCl_3$); $^1$H NMR (200 MHz, $CDCl_3$) δ0.85 (t, J=6.92 Hz, 3H), 1.16~1.45 (m, 7H), 1.91 (s, 3H), 2.43~2.46 (m, 2H), 4.06 (q, J=7.14 Hz, 2H), 4.14~4.28 (m, 1H), 6.25 (br, 1H). $^{13}$C NMR (50.3 MHz, $CDCl_3$) δ13.7, 14.0, 19.3, 23.2, 36.1, 38.5, 45.7, 60.4, 169.5, 171.8. MS m/z: 201, 186, 172, 158, 142, 116, 97, 72, 43.

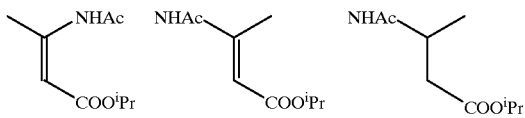

(Z)-Isopropypl 3-Acetamide-2butenoate. $^1$HNMR (360 MHz, $CDCl_3$) δ 1.42~1.45 (m, 6H), 2.32 (s, 3H), 2.55 (m, 3H), 5.05 (s, 1H), 5.20 (m, 1H), 11.3 (br, 1H); OR (360 MHz, Acetone-d6), δ 1.04 (m, 6H), 1.90 (s, 3H), 2.13 (s, 3H), 4.68 (s,1H), 4.70 (m, 1H), 10.9 (br, 1H). $^{13}$C NMR (90.6 MHz, $CDCl_3$) δ 21.7, 21.8, 25.1, 67.0, 96.8, 154.5, 168.5, 168.7 MS m/z 185, 142, 126, 101, 83, 57, 43.

(E)-Isopropyl 3-Acetamido-2-butenoate. $^1$H NMR (360 MHz, Acetone-d6) δ 1.10 (d, J=6.33 Hz, 6H), 1.94 (s, 3H), 2.20 (s, 3H), 4.85 (m, 1H), 6.74 (s, 1H), 8.55 (br, 1H). $^{13}$C NMR (90.6 MHz, Acetoned-6) δ 18.5, 22.6, 25.1, 66.9, 102.5, 151.1, 168.7, 170.5. MS m/z: 185, 142, 126, 110, 83, 57, 43.

(R)-Isopropyl 3-Acetamidobutanoate. $[α]_D^{25}$=+35.5 (c 1.91, CHCl$_3$); $^1$H NMR (360 MHz, CDCl$_3$) δ 1.13~1.18 (m, 6H), 1.88 (s, 3H), 2.37~2.47 (m, 2H), 4.24~4.28 (m, 1H), 4.92~4.96 (m, 1H), 6.59 (br, 1H). $^{13}$C NMR (90.6 MHz, CDCl$_3$) δ 19.8, 21.47, 21.53, 23.0, 40.4, 42.0, 67.7, 169.2, 170.9. MS m/z: 187, 144, 128, 102, 86, 69, 43.

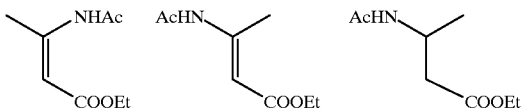

(Z)-Ethyl 3-Acetamido-2-butenoate. $^1$H NMR (360 MHz, CDCl$_3$) δ 1.05~1.09 (m, 3H), 1.93 (s, 3H), 2.17 (s, 3H), 3.93~3.95 (m, 2H), 4.68 (s, 1H), 10.9 (br, 1H). $^{13}$C NMR (90.6 MHz, CDCl$_3$) δ 14.1, 21.7, 25.1, 59.7, 96.3, 154.9, 168.8, 169.0. MS m/z: 171, 129, 98, 84, 69, 57, 43.

(E)-Ethyl 3-Acetamido-2-butenoate. $^1$H NMR (360 MHz, Acetone-d6) δ 1.39 (t, J=7.04 Hz, 3H), 2.23 (s, 3H), 2.49 (s, 3H), 4.25 (q, J=7.27 Hz, 2H), 7.04 (s, 1H), 8.91 (br, 1H). $^{13}$C NMR (90.6 MHz, Acetone-d6) δ 15.1, 18.5, 25.1, 59.9, 102.0, 151.4, 169.1, 170.6. MS m/z: 171, 156, 129, 98, 84, 57, 43.

(R)-Ethyl 3-Acetamidobutanoate. $[α]_D^{25}$=+41.9 (c 1.69, CHCl$_3$); $^1$H NMR (200 MHz, CDC$_{13}$) δ 1.15 (t, J=6.78 Hz, 3H), 1.18 (t, J=7.08 Hz, 3H), 1.88 (s, 3H), 2.41~2.44 (m, 2H), 4.06 (q, J=7.15 Hz, 2H), 4.22~4.30 (m, 1H), 6.42 (br, 1H). $^{13}$C NMR (50.3 MHz, CDCl$_3$) δ 14.0, 19.8, 23.2, 40.0, 41.9, 60.4, 169.3, 171.5. MS m/z: 173, 158, 130, 116, 86, 70, 43.

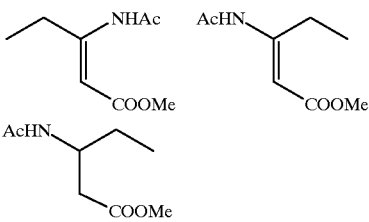

(Z)-Methyl 3-Acetamido-2-pentenoate. $^1$H NMR (360 MHz, CDCl$_3$) δ 1.03 (t, J=7.35 Hz, 3H), 2.07 (s, 3H), 2.72 (m, 2H), 3.62 (s, 2H), 4.89 (s, 1H), 11.0 (br, 1H). $^{13}$C NMR (90.6 MHz, CDCl$_3$) δ 12.1, 24.8, 26.9, 50.5, 93.9, 160.3, 167.9, 169.4. MS m/z: 171, 140, 129, 98, 84, 69, 43.

(E)-Methyl 3-Acetamido-2-pentenoate. $^1$H NMR (360 MHz, Acetone-d6) δ 1.21 (t, J=7.52 Hz, 3H), 2.15 (s, 3H), 2.84 (q, J=7.47 Hz, 2H), 3.69 (s, 2H), 6.96 (s, 1H), 8.80 (br, 1H). $^{13}$C NMR (90.6 MHz, Acetoned-6) δ 13.2, 24.4, 25.0, 50.4, 99.9, 156.6, 168.5, 170.3. MS m/z: 171, 140, 129, 112, 98, 84, 69, 43.

(R)-Methyl 3-Acetamidopentanoate. $[α]_D^{25}$=+52.0 (c 1.26, CHCl$_3$); $^1$H NMR (360 MHz, CDCl$_3$) δ 0.85 (t, J=7.49 Hz, 3H), 1.45~1.54 (m, 2H), 1.91 (s, 3H), 2.46~2.50 (m, 2H), 3.61 (s, 3H), 4.06~4.12 (m, 1H), 6.20 (br, 1H). $^{13}$C NMR (90.6 MHz, CDCl$_3$) δ 10.5, 23.2, 27.0, 37.9, 47.4, 51.5, 169.6, 172.1.

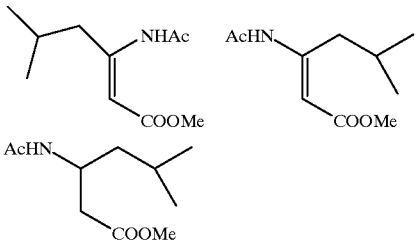

(Z)-Methyl 5-Methyl-3-Acetamido-2-hexenoate. $^1$H NMR (360 MHz, CDCl$_3$) δ 0.85

(E)-Methyl 5-Methyl-3-Acetamido-2-hexenoate. $^1$H NMR (360 MHz, Acetone-d6) δ 1.01 (d, J=6.72 Hz, 6H), 2.13~2.15 (m, 3H), 2.79 (d, J=7.44 Hz, 2H), 3.68 (s, 3H), 7.07 (s, 1H), 8.75 (br, 1H).

(R)-Methyl 5-Methyl-3-Acetamidohexanoate. $[α]_D^{25}$+ 44.6 (c 1.56, CHCl$_3$); $^1$H NMR (360 MHz, CDCl$_3$) δ 0.89~0.91 (m, 6H), 1.20~1.35 (m, 1H), 1.45~1.70 (m, 2H), 1.96 (s, 3H), 2.44~2.60 (m, 2H), 3.68 (s, 3H), 4.28~4.35 (m, 1H), 5.98 (br, 1H).

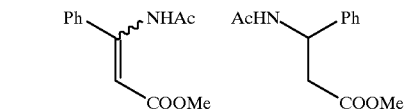

Methyl 3-Acetamido-3-phenyl-2-propenoate. $^1$H NMR (200 MHz, CDCl$_3$) δ Z-isomer: 2.17 (s, 3H), 3.77 (s, 3H), 5.29 (s, 1H), 7.37~7.45 (m, 5H); E-isomer: 2.38 (s, 3H), 3.77 (s, 3H), 6.65 (s, 1H), 7.37~7.45 (m, 5H).

(S)-Methyl 3-Acetamido-3-phenylpropanoate. $[α]_D^{25}$=−40.5 (c 2.15, MeOH); $^1$H NMR (360 MHz, CDCl$_3$) δ 1.92 (s, 3H), 2.76~2.83 (M, 2H), 3.53 (S, 3H), 5.34 (M, 1H), 6.65 (BR, 1H), 7.18~7.27 (M, 5H).

Determination of Enantiomeric Excesses

Chiral Capillary GC. Column: Chiral Select-1000 column. Dimensions: 15 m×0.25 mm (i.d.) or γ-DEX 225 column. Dimensions: 30 m×0.25 mm (i.d.). Carrier gas: He (1 mL/min). The racemic products were obtained by hydrogenation of substrates with an achiral catalyst. The following is the retention time for the racemic products.

Methyl 3-Acetamidobutanoate (capillary GC, Chiral Select-1000 column, 130° C., isothermal) (S) $t_1$=6.94 min, (R) $t_2$=8.29 min.

Ethyl 4-Methyl-3-Acetamidopentanoate (capillary GC, γ-DEX 225 column, 145° C., isothermal) (S $t_1$=18.81 min, (R) $t_2$=19.38 min.

Methyl 4,4-Dimethyl-3-Acetamidopentanoate (capillary GC, γ-DEX 225 column, 150° C., isothermal) (S) $t_1$=14.13 min, (R) $t_2$=14.78 min.

Ethyl 3-Acetamidohexanoate (capillary GC, γ-DEX 225 column, 140° C., isothermal) (S) $t_1$=25.72 min, (R) $t_2$=26.24 min.

Isopropyl 3-Acetamidobutanoate (capillary GC, Chiral Select-1000 column, 140° C., isothermal) (S) $t_1$=6.63 min, (R) $t_2$=7.33 min.

Ethyl 3-Acetamidobutanoate (capillary GC, Chiral Select-1000 column, 140° C., isothermal) (S) $t_1$=6.05 min, (R) $t_2$=6.67 min.

Methyl 3-Acetamidopentanoate (capillary GC, γ-DEX 225 column, 145° C., isothermal) (R) $t_1$=12.28 min, (S) $t_2$=12.63 min.

Methyl 5-Methyl-3-Acetamidohexanoate (capillary GC, γ-DEX 225 column, 145° C., isothermal) (S) $t_1$=17.20 min, (R) $t_2$=17.70 min.

Methyl 3-Acetamido-3-phenylpropanoate (capillary GC, Chiral Select-1000 column, 180° C., isothermal) (S) $t_1$=8.88 min, (R) $t_2$=9.32 min.

For the results of asymmetric hydrogenation catalyzed by Rh-complexes with different ligands, Table 3 lists the results for the E-isomer of enamides.

TABLE 3

Ligand Effect on Rh-Catalyzed Asymmetric Hydrogenation of an Enamide[a]

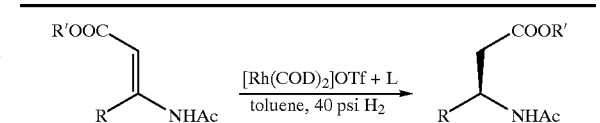

| Entry | Ligand | % ee[b] |
|---|---|---|
| 1 | (+)-DIOP | 79 |
| 2 | (R)-BINAP | 69 |
| 3 | (R,R)-BICP | 96.1 |
| 4 | (R,R)-Me-DuPhos | 99.3 |

[a]The reaction was completed at room temperature under an initial hydrogen pressure of 40 psi for 24 h using toluene as the solvent. The catalyst was made in situ by stirring a solution of [Rh(COD)₂]OTf and ligand in toluene for 30 min {[substrate (0.5 mmol, 0.125 M)/[Rh(COD)₂]OTf/Ligand = 1:0.01:0.011]}.
[b]Enantiomeric excesses were determined by chiral GC using a Chiral Select 1000 column. R-configuration was assigned by the hydrolysis product - phenylglycinol, through comparison of optical rotation.

For the synthesis of starting materials, following scheme outlines an effective procedure.

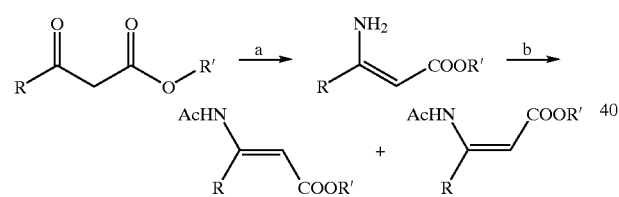

Reaction conditions and reagents:

a) $NH_4OAc$, MeOH, room temperature; b) $Ac_2O$, Pyridine, THF, reflux

Several experiments have been carried out using Rh-BICP or Rh—Me-DuPhos as catalysts. The Table below lists the experimental results.

| Entry[a] | R | R' | C=C | $H_2$ | Ligand | Conv. (%) | % ee[b] | Con-fig. |
|---|---|---|---|---|---|---|---|---|
| 1 | i-Pr | Et | Z | 294 | BICP | 100 | 91.0 | S |
| 2 | i-Pr | Et | Z | 294 | Me-DuPhos | 100 | 42.1 | S |
| 3 | i-Pr | Et | E | 40 | BICP | 100 | 97.0 | S |
| 4 | i-Pr | Et | E | 40 | Me-DuPhos | 100 | 97.6 | S |
| 5 | t-Bu | Me | Z | 294 | BICP | 71.4 | 52.7 | S |
| 6 | i-Pr | Et | Z | 294 | Me-DuPhos | 100 | 21.7 | S |
| 7 | Pr | Et | Z | 294 | BICP | 100 | 90.7 | R |
| 8 | Pr | Et | Z | 294 | Me-DuPhos | 100 | 34.4 | R |
| 9 | Pr | Et | E | 40 | BICP | 100 | 96.6 | R |
| 10 | Pr | Et | E | 40 | Me-DuPhos | 100 | 99.6 | R |
| 11 | Me | i-Pr | Z | 294 | BICP | 100 | 86.4 | R |
| 12 | Me | i-Pr | Z | 294 | Me-DuPhos | 95.2 | 61.9 | R |
| 13 | Me | i-Pr | E | 40 | BICP | 100 | 95.6 | R |
| 14 | Me | i-Pr | E | 40 | Me-DuPhos | 100 | 98.1 | R |
| 15 | Me | Et | Z | 294 | BICP | 100 | 88.0 | R |
| 16 | Me | Et | Z | 294 | Me-DuPhos | 100 | 62.3 | R |
| 17 | Me | Et | E | 40 | BICP | 100 | 96.0 | R |
| 18 | Me | Et | E | 40 | Me-DuPhos | 100 | 98.7 | R |
| 19 | Et | Me | Z | 294 | BICP | 100 | 86.9 | R |
| 20 | Et | Me | Z | 294 | Me-DuPhos | 100 | 21.2 | R |
| 21 | Et | Me | E | 40 | BICP | 100 | 96.8 | R |
| 22 | Et | Me | E | 40 | Me-DuPhos | 100 | 99.6 | R |
| 23 | i-Bu | Me | Z | 294 | BICP | 93.1 | 92.9 | R |
| 24 | i-Bu | Me | Z | 294 | Me-DuPhos | 96.0 | 62.4 | R |
| 25 | i-Bu | Me | E | 40 | BICP | 100 | 90.9 | R |
| 26 | i-Bu | Me | E | 40 | Me-DuPhos | 100 | 98.5 | R |
| 27 | Ph | Me | mixture | 294 | BICP | 100 | 66.0 | S |
| 28 | Ph | Me | mixture | 294 | Me-DuPhos | 100 | 65.1 | S |
| 29 | Me | Me | Z | 294 | BICP | 100 | 88.6 | R |
| 30 | Me | Me | Z | 294 | Me-DuPhos | 100 | 63.7 | R |
| 31 | Me | Me | E | 40 | BICP | 100 | 96.1 | R |
| 32 | Me | Me | E | 40 | Me-DuPhos | 100 | 99.3 | R |

[a]The reaction was completed at room temperature under an initial hydrogen pressure of 40 psi (or 20 atm) for 24 h using toluene as the solvent. The catalyst was made in situ by stirring a solution of [Rh(COD)₂]OTf and ligand in toluene for 30 min {[substrate (0.5 mmol, 0.125 M)/[Rh(COD)₂]OTf/Ligand = 1:0.01:0.011]}.
[b]Enantiomeric excesses were determined by chiral GC using a Chiral Select 1000 column or gamma-DEX-225.

Example 3. Hydrogenation of Cyclic Enamides

Chiral amines are critical building blocks in many pharmaceuticals, which exist in about 15 to 25% of the developmental single-enantiomer products. Traditional resolution methods and enzymatic transaminase technology are frequent choices for the synthesis of chiral amines in industry. However, attention has recently shifted to asymmetric hydrogenation of imines and enamides because it represents one of the most efficient production methods. A variety of chiral Rh, Ir, Ru, and Ti complexes have been explored as catalysts for asymmetric hydrogenation of imines, despite of some impressive achievements, efficient practical methods for the enantioselective reduction of imines is still limited.

Recently, Burk and coworkers have reported that Rh-complexes bearing an electron-rich bisphosphine (Duphos or BPE) ligand were efficient catalysts for the asymmetric hydrogenation of acyclic enamides (J. Am. Chem. Soc. 1996 118 5142; J. Am. Chem. Soc. 1998 120 657), but asymmetric hydrogenation of cyclic enamides still is an unsolved problem. One example has been reported on asymmetric hydrogenation of N-(6-bromo-1,2,3,4-tetrahydronaphthalene)yl benzamide using Ru-BINAP complex as catalyst: Tschaen, D. M. et al., J. Org. Chem. 1995 60 4324.

In our continuing efforts on catalytic asymmetric hydrogenation, we have been interested in elucidating the steric and electronic effects of the chiral ligands on the enantioselectivities and catalytic activities by rationally designing new electron-rich and conformationally rigid chiral bisphosphine and monophosphine ligands. (See Zhu, G. et al., J. Am. Chem. Soc. 1997 119 1799; Zhu, G. et al., J. Am. Chem. Soc. 1997 119 3836; Chen, Z et al., J. Org. Chem. 1997 62 4521.) We recently synthesized a new bisphosphine ligand, PennPhos(P,P'-1,2-phenylenebis(endo-2,5-dialkyl-7-phosphabicyclo[2.2.1]heptane), which is both electron-rich and, conformationally rigid, and have obtained excellent results in. Rh-PennPhos complex catalyzed asymmetric hydrogenation of simple ketones (Jiang, Q. et al., Angew. Chem. Int. Ed. Engl. 1998, 37, 1100). Herein we report the highly enantioselective Rh-PennPhos catalyzed hydrogenation of cyclic enamides.

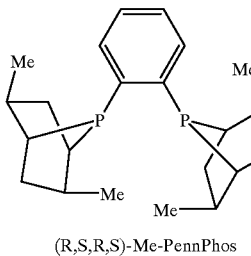

(R,S,R,S)-Me-PennPhos

We initially selected N-(3,4-dihydroxynaphthalene-1-yl) acetamide as the substrate. The enamides could be easily prepared by reduction of correspond oxime with iron powder in the presence of acetic anhydride in DMF The hydrogenation proceeded smoothly in the presence of commercially available [Rh(COD)Cl]$_2$ and Me-PennPhos in methylene chloride at room temperature with a ratio of substrate: Rh:Me-PennPhos=100:1:1.1 and hydrogen pressure of 40 psi, (eq. 1) complete conversion and the R-enantiomer with 92% ee was obtained. The absolute configuration was determined by comparing the GC trace of the acetamide derived from R-1-aminoindan and R-1-aminotetralin (Lancaster samples). When we used Rh(COD)$_2$BF$_4$ and Rh(COD)$_2$PF$_6$ instead of [Rh(COD)Cl]$_2$, 97% and 98% ee were obtained, respectively, with 100% conversion (Table 4).

TABLE 4

Rh-Catalyzed Asymmetric Hydrogenation of an Enamide[a]

| Entry | Rh(1)Species | Ligand | % ee[b] |
|---|---|---|---|
| 1 | [Rh(COD)Cl]$_2$ | (R,S,R,S)-Me-PennPhos | 92 (R) |
| 2 | Rh(COD)$_2$BF$_4$ | (R,S,R,S)-Me-PennPhos | 97 (R) |
| 3 | Rh(COD)$_2$PF$_6$ | (R,S,R,S)-Me-PennPhos | 98 (R) |
| 4 | Rh(COD)$_2$PF$_6$ | (+)-DIOP | 10 (S) |
| 5 | Rh(COD)$_2$PF$_6$ | (R)-BINAP | 24 (R) |
| 6 | Rh(COD)$_2$PF$_6$ | (R,R)-Me-DuPhos | 1[c] (R) |

[a]The reaction was completed in quantitative yield at room temperature under an initial hydrogen pressure of 40 psi for 20 h using MeOH as the solvent. The catalyst was made in situ by stirring a solution of Rh catalyst and a phosphine ligand in MeOH for 30 min {[substrate (0.5 mmol, 0.17 M)/Rh cat./ligand B 1:0.01:0.011]}.

TABLE 4-continued

Rh-Catalyzed Asymmetric Hydrogenation of an Enamide[a]

| Entry | Rh(1)Species | Ligand | % ee[b] |
|---|---|---|---|

[b]Enantiomeric excesses were determined by chiral GC using a Supelco Chiral Select 1000 (0.25 mm × 15 m) column.
[c]57% conversion.

Using Ph(COD)$_2$PF$_6$ as catalyst precursor, different solvents were tested. The hydrogenation finished with high % ee in methanol (98% ee) and isopropanol (97% ee), but in toluene, due to the poor solubility of the enamide in it, the conversion was low (27%) with little % ee change (96%). Since methanol is cheap and environmentally friendly, we chose it as solvent.

The hydrogen pressure at a certain range (balloon pressure to 500 psi) did not have an obvious effect on the enantiomeric excess. When the reaction was run at 500 psi, the % ee remained the same (98% ee), while when using balloon as hydrogen source, slightly higher % ee (>99% ee) was recorded at the cost of much lower conversion (6%).

Other well-known bisphosphine ligands were examined in same conditions. When DIOP and BINAP were used, the conversions were 100%, but the ee were –10% and 24%, respectively. Strangely, Me-DuPhos showed less reactivity (57% conversion) and poor asymmetric induction (1% ee) though it shares some features with Me-Pennphos regardless of its less bulkiness and rigidity (Table 4).

The catalytic system was not only suitable for a 6-member ring cyclic enamide, but also effective for a 5-member ring one. When enamide derived from 1-indanone was used, high % ee and complete conversion were obtained (Entry 1, Table 5). What is more, the reaction was not sensitive to the substituents on the aromatic ring: with an electron-withdrawing group on the ring, the % ee became slightly higher (Entry 4, Table 5), in case of an electron-donating group, the % ee was slightly lower (Entry 5, Table 5). But when the enamide derived from 2-tetralone was used, only moderate % ee was observed.

Because of the high reactivity of the Rh-PennPhos catalyst, this new complex makes a sharp contrast to the Rh-BINAP complex in asymmetric hydrogenation of unsaturated amide substrates; even tetra-substituted enamides could be reduced easily (Entry 8,9, Table 5). The introduced substituent on the 2-carbon of a 5-member ring enamide seemed to have no influence on the reduction, but with a 6-member ring enamide, the % ee dramatically decreased.

When these conditions were applied to acyclic enamides, moderate to high ee were observed (entries 10–12, Table 5). Tri-substituted enamides gave better results than the terminal enamide (compare entries 10 and 12, Table 5). This was also observed when using the Rh-BICP system.

Another merit of the Rh-PennPhos catalytic system is its high efficiency. When N-(3,4-dihydronaphthalen-1-yl) acetamide was used as the substrate, with a ratio of substrate: Rh:Me-PennPhos of 2000:1:1.1, and the other conditions were kept the same, the same result (100% conversion, 98% ee) was achieved.

In summary, we have developed an efficient Rh-Pennphos catalytic system for asymmetric hydrogenation of enamides.

It is especially useful for chiral cyclic amine preparation. Its high efficiency, wide substrate choice and little pressure sensitivity made it a possible entry to large quantity chiral amine production.

TABLE 5

Asymmetric Hydrogenation of Enamides Catalyzed by a Me-PennPhos-Rh Complex[a]

| Entry | Substrate | % ee[b] |
|---|---|---|
| 1 | (indene-NHAc) | 98 |
| 2 | (dihydronaphthalene-NHAc) | 98 |
| 3 | (dimethyl dihydronaphthalene-NHAc) | >99 |
| 4 | (dimethyl dihydronaphthalene-NHAc) | >99 |
| 5 | (MeO-dihydronaphthalene-NHAc) | 97 |
| 6 | (chromene-NHAc) | 90 |
| 7 | (dihydronaphthalene-NHAc) | 71 |
| 8 | (methyl indene-NHAc) | 98 |
| 9 | (methyl dihydronaphthalene-NHAc) | 73 |
| 10 | (styryl-NHAc) | 75 |
| 11 | (F$_3$C-styryl-NHAc) | 88 |
| 12 | (styryl-NHAc) | 90 |

[a]The reaction was completed in quantitative yield at room temperature under an initial hydrogen pressure of 40 psi for 20 h using MeOH as the solvent. The catalyst was made in situ by stirring a solution of [Rh(COD)$_2$]PF$_6$ and Me-PennPhos in MeOH for 30 min {[substrate (0.5 mmol, 0.17 M)/Rh(COD)$_2$]PF$_6$ and Ligand = 1:0.01:0.011]}.
[b]Enantiomeric excesses were determined by chiral GC using a Supelco Chiral Select 1000 (0.25 mm × 15 m) column.

Example 4. Hydrogenation of β-Hydroxy Enamides to β-Amino Alcohols

Enantiomerically pure β-amino alcohols have been extensively used as building blocks for the syntheses of pharmaceuticals and insecticidal agents, as chiral ligands in asymmetric catalysis, or as auxiliaries and resolving agents in asymmetric synthesis. Furthermore, they can be converted to chiral oxazoline ligands, which show tremendous utilities in various asymmetric catalytic processes. The broad applications of amino alcohol derivatives have generated considerable interests in searching efficient synthetic routes to these compounds (Ager, D. J. et al., Chem. Rev., 1996, 96, 835 and references cited therein.). Such amino alcohols generally are obtained by reduction of the corresponding β-amino acids or esters. However, not all of corresponding α-amino acids or esters are available and sometimes low yields are observed in this reduction. To address this challenging, several asymmetric synthetic methods have been developed (Ager, D. J. et al., Tetrahedron 1993, 49, 5683; Reddy, K. L. et al., J. Am. Chem. Soc. 1998 120 1207, and references cited therein). In principle, asymmetric catalytic hydrogenation of β-hydroxyl enamides is a potentially practical way to generate such amino alcohols. Although high enantioselectivities and reactivities have been reported for the asymmetric hydrogenation of dehydroamino acids, there has been no report for the synthesis of β-amino alcohols via asymmetric catalytic hydrogenation of enamides as illustrated in Scheme 1. Herein, we describe the first highly enantioselective, practical synthesis of β-amino alcohols using BICP-Rh and Me-DuPhos complexes as the catalysts.

Scheme 1

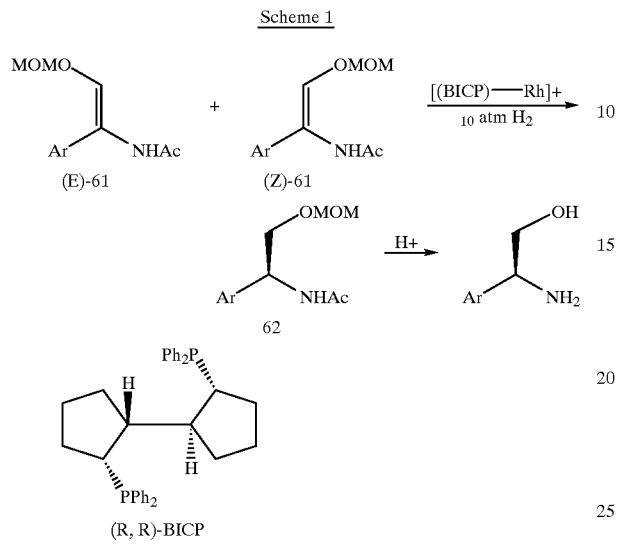

The basic strategy for the synthesis of chiral β-amino alcohols involves asymmetric hydrogenation of α-arylenamides with a MOM-protected β-hydroxyl group. Rh-catalyzed asymmetric hydrogenation must tolerate the E and Z isomer of these enamides since preparation and isolation of the isomerically pure (E) and (Z) isomers are difficult. Another practical issue in the synthesis is the formation of β-hydroxyl substituted enamides. We have carried out several reactions to make these MOM-protected β-hydroxy substituted enamides in gram quantities from readily available 2-haloacetophenone derivatives 63 as outlined in the reaction shown below. The first step involves synthesis of 2-hydroxyacetophenone derivatives 64 through nucleophilic attack of corresponding 2-haloacetophenone by sodium formate and followed by a hydrolysis reaction. Protection of hydroxyl group by methoxymethyl group (MOM) went smoothly giving MOM protected ketoalcohol 65 in good yield. The key step for the synthesis of enamide 61 is the reduction of the corresponding oxime 66 of the MOM protected ketoalcohol by iron powder in DMF. The reduction reaction of oxime 66 proceeded smoothly in the presence of acetic anhydride at room temperature affording the MOM-protected β-hydroxy substituted enamides 61 in good yield. After completion of the asymmetric hydrogenation, the protecting groups (N-acetyl and MOM) in the reduction products can be easily removed under acidic conditions to afford the enantiomerically-enriched β-amino alcohols.

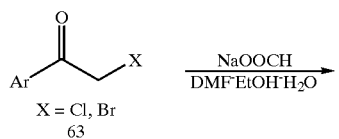

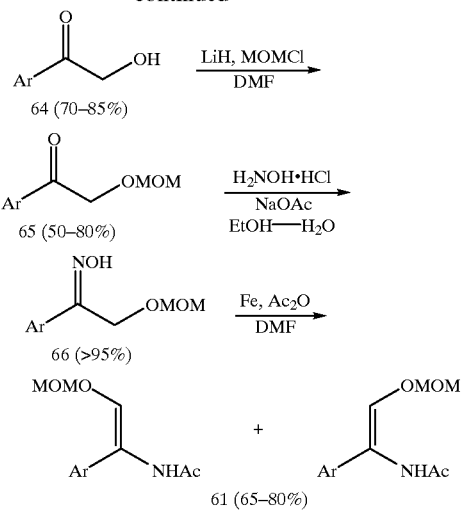

MOM = CH$_2$OCH$_3$

To achieve our synthetic goal, we have screened the asymmetric hydrogenation conditions using Rh-catalysts with different chiral bisphosphines Results are shown in the Table below.

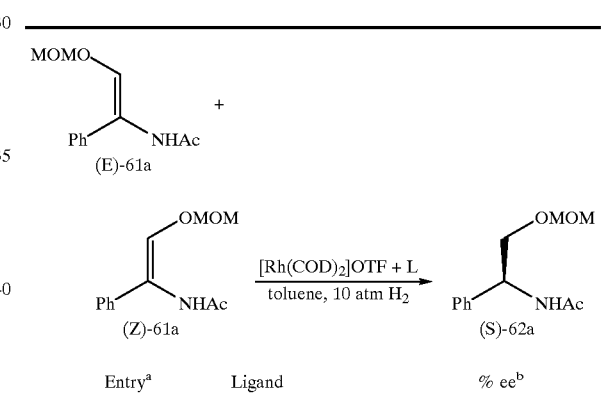

| Entry[a] | Ligand | % ee[b] |
|---|---|---|
| 1 | (+)-DIOP | 88 |
| 2 | (R)-BINAP | 15 |
| 3 | (R,R)-BICP | 94 |
| 4 | (R,R)-Me-DuPhos | 97 |

[a]The reaction was completed at room temperature under an initial hydrogen pressure of 10 atm for 24–36 hr using toluene as the solvent. The catalyst was made in situ by stirring a solution of [Rh(COD)$_2$]OTf and ligand in toluene for 30 min {[substrate (0.5 mmol, 0.125 M)/[Rh(COD)$_2$OTf/Ligand = 1:0.01:0.011]}.
[b]Enantiomeric excesses were determined by chiral HPLC using a Regis (R,R)-Whelk-O1 column. S-configuration was assigned by the hydrolysis product - phenylglycinol, through comparison of optical rotation.

The typical reaction was carried out at room temperature in toluene under an initial H$_2$ pressure of 10 atmosphere for 24 to 36 h. Our experimental results show that cationic Rh complexes bearing a variety of chiral bisphosphines are active catalyst for this transformation, but the enantioselectivities are ligand dependent. For examples, using α-phenylenamide 61a (Ar=C$_6$H$_5$) as a model substrate, the hydrogenation catalyzed by rhodium complexes with three different chiral bisphosphines bearing diphenylphosphino groups went all in quantitative yield but with quite different enantioselectivities: 88% ee with DIOP (entry 1, Table), 15% ee with BINAP (entry 2, Table) and 94% ee with BICP (entry 3, Table). The (R,R)-BICP ligand, (2R,2'R)-bis(diphenylphosphino)-(1R,1'R)dicyclopentane ((R,R)-BICP) is a conformationally rigid chiral 1,4-bisphosphine, which was recently reported by our group as an efficient phosphine ligand for the rhodium catalyzed asymmetric hydrogenation of dehydroamino acids (Zhu, G. et al., J. Am. Chem. Soc. 1997 119 1799). The high enantioselectivity for the asymmetric hydrogenation of these isomeric Z- and E-mixtures of the MOM-protected β-hydroxy substituted enamides 61 as shown in Scheme 1 demonstrates broader utilities of our new ligand system compared with other chiral bisphosphines bearing diphenylphosphino groups. Prior to our study, the only asymmetric catalysts can efficiently hydrogenate mixtures of (E) and (Z)-α-arylenamides are Me-DuPhos-Rh and Me-BPE-Rh catalysts developed by Burk et al. (Burk, M. J. et al., J. Am. Chem. Soc. 1996 118 5142). Indeed, high enantioselectivity (97% ee, entry 4) has been obtained in the hydrogenation of α-arylenamide 61a using a Me-DuPhos-Rh complex as a catalyst.

Under the standard set of conditions (10 atm initial pressure of hydrogen in toluene at room temperature), we have performed asymmetric hydrogenation of various α-arylenamides 61 with a MOM protected β-hydroxyl group (Table 6) catalyzed by Rh-BICP and Rh-Me-DuPhos complexes. A variety of N-acetyl and O-MOM protected arylglycinols were obtained in quantitative yield with high enantiomeric excesses (Table 6). Overall, the BICP-Rh catalyst gives comparable results with the Me-DuPhos-Rh catalyst. However, Me-DuPhos-Rh catalyst displays slightly broader substrate generality than the BICP-Rh-catalyst, For example, while 90% ee was obtained with the BICP-Rh catalyst for the p-methoxylphenyl enamide 61c (entry 3), 95% ee was obtained in the Me-DuPhos-Rh system under the identical condition (entry 11). Enamides with electron-withdrawing groups on the aryl or sterically demanding groups enhance the enantioselectivity with the BICP-Rh catalytic system (entries 4–7 vs. entries 1–3). The trend is less compelling with the Me-DuPhos-Rh catalyst. To test if the MOM group is necessary for high enantioselectivity in this reaction, we replaced the MOM protective group of the hydroxyl group in enamide 61a with a methyl group (71i). Under the same reaction conditions, the enamide with a β-methoxy group 61i was hydrogenated in high yield with 98% ee using the BICP-Rh catalyst. This result indicates that a variety of substrates with substituents on the β-position may be hydrogenated with high enantioselectivities using the BICP-Rh catalyst. The hydrogenation products 62 can be easily converted to α-arylglycinols by deprotection of O-MOM and N-acetyl groups in acidic conditions. For example, the hydrogenation product of 61a was hydrolyzed to (S)-phenylglycinol in 81% yield in an acidic MeOH solution, Thus, the absolute configuration of the hydrogenation product of 61a was also assigned as S-form. The N-protected α-arylglycinols can be oxidized to obtain useful α-arylglycines.

TABLE 6

Asymmetric Catalytic Synthesis of β-Aminoalcohol Derivatives via Rh-Catalyzed Hydrogenation.[a]

| Entry | Ar (61) | Ligand | % ee |
|---|---|---|---|
| 1 | $C_6H_5$ (61a) | (R,R)-BICP | 94 |
| 2 | p-$CH_3$-$C_6H_4$ (61b) | (R,R)-BICP | 94 |
| 3 | p-MeO-$C_6H_4$ (61c) | (R,R)-BICP | 90 |
| 4 | p-$C_6H_5$-$C_6H_4$ (61d) | (R,R)-BICP | 99 |
| 5 | p-Cl-$C_6H_4$ (61e) | (R,R)-BICP | 97 |

TABLE 6-continued

Asymmetric Catalytic Synthesis of β-Aminoalcohol Derivatives via Rh-Catalyzed Hydrogenation.[a]

| Entry | Ar (61) | Ligand | % ee |
|---|---|---|---|
| 6 | p-F-$C_6H_4$ (61f) | (R,R)-BICP | 97 |
| 7 | 2,4-$F_2C_6H_3$ (61g) | (R,R)-BICP | 98 |
| 8 | 2-Naphthyl (61h) | (R,R)-BICP | 95 |
| 9 | $C_6H_5$ (61a) | (R,R)-Me-DuPhos | 97 |
| 10 | p-$CH_3$-$C_6H_4$ (61b) | (R,R)-Me-DuPhos | 96 |
| 11 | p-MeO-$C_6H_4$ (61c) | (R,R)-Me-DuPhos | 95 |
| 12 | p-$C_6H_5$-$C_6H_4$ (61d) | (R,R)-Me-DuPhos | 97 |
| 13 | p-Cl-$C_6H_4$ (61e) | (R,R)-Me-DuPhos | 98 |
| 14 | p-F-$C_6H_4$ (61f) | (R,R)-Me-DuPhos | 98 |
| 15 | 2,4-$F_2C_6H_3$ (61g) | (R,R)-Me-DuPhos | 95 |
| 16 | 2-Naphthyl (61h) | (R,R)-Me-DuPhos | 98 |

[a]The reaction was completed in quantitative yield at room temperature under an initial hydrogen pressure of 10 atm for 24–36 h using toluene as the solvent. The catalyst was made in situ by stirring a solution of [Rh(COD)2]OTf and ligand in toluene for 30 min.

In conclusion, we have reported efficient syntheses of enantiomerically-enriched β-amino alcohols using a practical asymmetric hydrogenation method. Cationic BICP-Rh and Me-DuPhos-Rh complexes are excellent catalysts for this transformation. An interesting character of these catalytic systems is that hydrogenation of the mixture of (E) and (Z)-enamides can occur with high enantioselectivities. The finding is of great significant in asymmetric synthesis as it provides convenient access to an important class of chiral compounds.

General Procedures

Enamide synthesis is shown in the following Scheme:

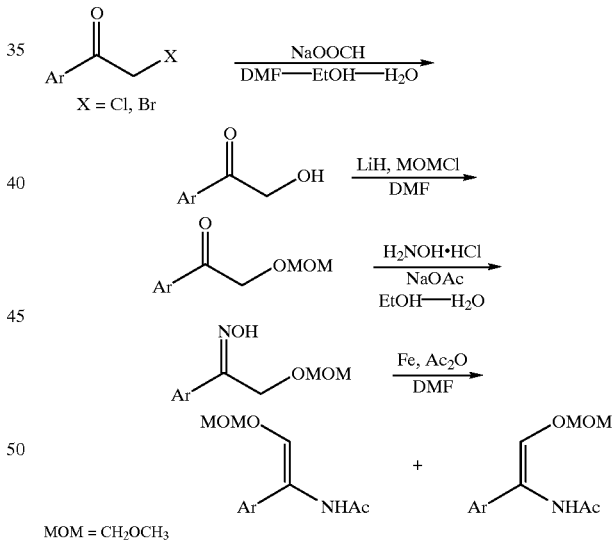

MOM = CH2OCH3

Synthesis of 2-Hydroxyacetophenone Derivatives, General Procedure.

A mixture of 2-chloroacetophenone derivatives (or 2-bromoacetophenone derivatives, 0.19 mol), NaOOCH (0.59 mol) in DMF (140 mL), $H_2O$ (100 mL) and EtOH (400 mL) was heated under refluxing. After 5–8 hrs, the reaction mixture was cooled to room temperature, then about half of the solvent was removed under vacuum. The residue was diluted with water, and extracted with $CH_2Cl_2$. The combined organic layer was washed by $H_2O$, followed by brine;. After drying over $Na_2SO_4$, solvents were evaporated under vacuum. The crude product was washed with hexanes, filtration gave the desired 2-hydroxyacetophenone derivatives as a solid in 70~85% yield, which were used directly for the next step.

Synthesis of O-Methoxymethyl-2-hydroxyacetophenone Derivatives, General Procedure.

Under nitrogen, to a solution of 2-hydroxyacetophenone derivatives (2) (65 mmol) and chloromethoxymethylether (MOMCl, 130 mmol) in dry DMF (80 mL) was added solid LiH (65 mmol) in portions at −5° C. to 0° C. After addition of LiH, another portion of MOMCl (130 mmol) was added. The mixture was stirred at −5° C. to 0° C. for 10 min, then solid LiH (65 mmol) was added in portions again. After the addition of LiH, the reaction mixture was allowed to warm up to room temperature. After stirred at room temperature for ca. 4 hrs, the reaction was quenched by adding an aqueous bicarbonate. The mixture was extracted with EtOAc and then the combined organic layer was washed with water and brine. After dried over $Na_2SO_4$, the solvent was removed under reduced pressure. The crude product was purified by flash chromatography on silica gel to give the desired product at about 50–80% yield.

Synthesis of O-Methoxymethyl-2-hydroxyacetophenone Oxime Derivatives, General Procedure.

The MOM protected ketoalcohol (51 mmol) was refluxed with $NH_2OH.HCl$ (102 mmol) and NaOAc (102 mmol) in a mixture solvent of EtOH (97 mL) and water (43 mL). After heated about 2–6 hrs at reflux, the reaction mixture was cooled to room temperature. The reaction mixture was diluted with water, then extracted with EtOAc. The combined organic layer was washed with water and brine. After dried over $Na_2SO_4$, evaporation of the solvent gave the crude oxime product with high yield, which was used directly for the next step.

Synthesis of 2-(N-Acetylamido)-2-arylvinyl Methoxymethylether, General Procedure.

To a stirred solution of oxime (21.5 mmol) and acetic anhydride (16.2 mL) in DMF (53 mL) was added iron powder (10.8 g), then the reaction was initiated by adding few drops of chlorotrimethylsilane under nitrogen. After the reaction mixture was stirred at room temperature for 4–8 hrs, TLC showed that the reaction was complete. The reaction mixture was diluted with ether, and solid was filtered off through a short column of celite. The filtrate was concentrated and the residue was purified by flash chromatography on silica gel. The product was further purified by recrystallization. The yield was about 65–80%.

2-(N-Acetylamido)2-phenylvinyl Methoxymethylether. $^1$H NMR (360 MHz, $CDCl_3$) δ mixture of Z & E isomers (ratio: 69:31). Major isomer: 2.02 (s, 3H), 3.37 (s, 3H), 4.83 (s, 2H), 6.54 (s, 1H), 7.14~7.29 (m, 6H). Minor isomer 1.80 (s, 3H), 3.37 (s, 3H), 4.88 (s, 2H), 6.68 (s, 1H), 6.80 (br, 1H), 7.14~7.29 (m, 5H). $^{13}$C NMR ($CDCl_3$) mixture of isomers: δ 23.6 (21.0), 56.6 (56.7), 97.1 (97.4), 118.7 (119.0), 125.1 (124.9), 128.0 (127.4), 128.7 (129.2), 135.7 (136.1), 137.7 (139.5), 169.1 (174.2). MS m/z: 221, 190, 176, 161, 134, 104, 77, 45, 43; HRMS calcd for $C_{12}H_{15}NO_3$ (M+): 221.1052; found: 221.1052.

2-(N-Acetylamido)-2-(4-phenylphenyl)vinyl Methoxymethylether. $^1$H NMR (300 MHz, $CDCl_3$) δ mixture of Z & E isomers (ratio: 68:32). Major isomer: 2.17 (s, 3H), 3.46 (s, 3H), 4.95 (s, 2H), 6.66 (s, 1H), 6.86 (br, 1H), 7.33~7.59 (m, 9H). Minor isomer: 1.91 (s, 3H), 3.46 (s, 3H), 4.97 (s, 2H), 6.60 (s, 1H), 6.80 (br, 1H), 7.33~7.59 (m, 9H). $^{13}$C NMR ($CDCl_3$) mixture of isomers: δ 23.5 (20.7), 56.3, 96.8, 118.2, 124.8~140.7 (m), 168.4 (173.6). MS m/z: 297, 268, 235, 223, 210, 180, 165, 152, 124, 43; HRMS calcd for $C_{18}H_{19}NO_3$ (M+): 297.1365; found: 297.1364.

2-(N-Acetylamido)-2-(4-methoxyphenyl)vinyl Methoxymethylether. $^1$H NMR (360 MHz, $CD_3COCD_3$) δ mixture of Z & E isomers. Major isomer: 2.16 (s, 3H), 3.52 (s, 3H), 3.90 (s, 3H), 5.05 (s, 2H), 6.74 (s, 1H), 6.95~7.04 (m, 4H), 8.28 (br, 1H). Minor isomer: 1.90 (s, 3H), 3.50 (s, 3H), 3.91 (s, 3H), 5.15 (s, 2H), 6.95~7.40 (m, 6H). $^{13}$C NMR ($CD_3COCD_3$) mixture of isomers: δ 23.6 (21.1), 56.0 (55.9), 56.5, 97.9 (98.5), 114.8 (114.4), 119.4 (118.0), 127.0, 130.3 (129.7), 138.2 (140.3), 160.0 (159.8), 168.9 (170.4). MS m/z: 251, 222, 206, 191, 164, 134, 109, 91, 77, 45, 43; HRMS calcd for $C_{13}H_{17}NO_4$ (M+): 251.1158; found: 251.1162.

2-(N-Acetylamido)-2-(2-naphthyl)vinyl Methoxymethylether. $^1$H NMR (300 MHz, $CDCl_3$) δ mixture of Z & E isomers (ratio: 62:38). Major isomer: 2.21 (s, 3H), 3.49 (s, 3H), 4.98 (s, 2H), 6.74 (s, 1H), 6.80 (br, 1H), 7.43~7.51 (m, 3H), 7.73~7.79 (m, 4H). Minor isomer: 1.90 (s, 3H), 3.46 (s, 3H), 5.00 (s, 2H), 6.62 (br, 1H), 6.89 (br, 1H), 7.43~7.51 (m, 3H), 7.73~7.79 (m, 4H). $^{13}$C NMR ($CDCl_3$) mixture of isomers: δ 24.0 (21.1), 56.7, 97.3, 118.9~139.9 (m), 169.9 (174.2). MS m/z: 271, 239, 211, 184, 154, 129, 86, 45; HRMS calcd for $C_{16}H_{17}NO_3$ (M+): 271.1208; found: 271.1210.

2-(N-Acetylamido)-2-(4-chlorophenyl)vinyl Methoxymethylether. $^1$H NMR (360 MHz, $CDCl_3$) δ mixture of Z & E isomers (ratio: 75:25). Major isomer: 2.19 (s, 3H), 3.53 (s, 3H), 5.00 (s, 2H), 6.65 (s, 1H), 6.89 (br, 1H), 7.24~7.39 (m, 4H). Minor isomer 1.94 (s, 3H), 3.53 (s, 3H), 5.04 (s, 2H), 6.84 (br, 1H), 7.24~7.39 (m, 4H). $^{13}$C NMR ($CDCl_3$) mixture of isomers: δ 23.7 (21.0), 56.7, 97.3 (97.5), 118.0, 126.3 (126.1), 128.8 (129.4), 132.9 (133.6), 134.2 (14.7), 137.6 (139.9), 169.1 (174.1). MS m/z: 257 (37Cl), 235 (35Cl), 226 (37Cl), 224 (39Cl), 212 (17Cl), 210 1 196 (7Cl), 194 (35Cl), 170 (37Cl), 168 (37Cl), 140 (37Cl), 138 (35Cl), 110, 102, 75, 45, 43; HRMS calcd for $C_{12}H_{14}ClNO_3$ (M+): 257.0633 (37Cl), 255.0662 (35Cl); found: 257.0635 (37Cl), 255.0659 (35Cl).

2-(N-Acetylamido)-2-(4-methylphenyl)vinyl Methoxymethylether. $^1$H NMR (360 MHz, $CDCl_3$) δ mixture of Z & E isomers (ratio: 62:38). Major isomer: 2.16 (s, 3H), 2.33 (s, 3H), 3.46 (s, 3H), 4.93 (s, 2H), 6.55 (s, 1H), 6.80 (br, 1H), 7.12~7.27 (m, 4H). Minor isomer: 1.87 (s, 3H), 2.35 (s, 3H), 3.45 (s, 3H), 4.95 (s, 2H), 6.68 (s, 1H), 7.12~7.27 (m, 4H). $^{13}$C NMR ($CDCl_3$) mixture of isomers: δ 21.5 (21.0), 23.6, 56.5 (56.7), 97.1 (97.3), 118.7 (119.0), 125.1 (124.9), 129.4 (129.9), 132.8 (133.2), 137.0 (137.8), 138.7, 169.0 (174.2). MS m/z: 235, 206, 190, 175, 161, 148, 118, 91, 77, 45, 43; HRMS calcd for $C_{13}H_{17}NO_3$ (M+): 235.1208; found: 235.1217.

2-(N-Acetylamido)-2-(4-fluorophenyl)vinyl Methoxymethylether. $^1$H NMR (300 MHz, $CDCl_3$) δ mixture of Z & E isomers (ratio: 75:25). Major isomer: 2.02 (s, 3H), 3.38 (s, 3H), 4.84 (s, 2H), 6.44 (s, 1H), 6.87~6.97 (m, 2H), 7.16~7.27 (m, 3H). Minor isomer: 1.80 (s, 3H), 3.38 (s, 3H), 4.88 (s, 2H), 6.62 (s, 1H), 6.87~6.97 (m, 3H), 7.16~7.27 (m, 2H). $^{13}$C NMR ($CDCl_3$) mixture of isomers: δ 23.0 (20.4), 56.0 (55.9), 96.6 (96.8), 114.8~138.6 (m), 161.7 (d, J=245.7 Hz), 168.6 (173.6). MS m/z: 239, 165, 152, 122, 95, 45, 43; HRMS calcd for $C_{12}H_{14}FNO_3$ (M+): 239.0958; found: 239.0962.

2-(N-Acetylamido)-2-(2,4-difluorophenyl)vinyl Methoxymethylether. $^1$H NMR (360 MHz, $CDCl_3$) δ mixture of Z & E isomers (ratio: 81:19). Major isomer: 1.87 (s, 3H), 3.25 (s, 3H), 4.72 (s, 2H), 6.28 (s, 1H), 6.50~7.20 (m, 4H). Minor isomer 1.70 (s, 3H), 3.25 (s, 3H), 4.80 (s, 2H), 6.50~7.20 (m, 5H). $^{13}$C NMR ($CDCl_3$) mixture of isomers: δ 23.6 (20.6), 56.8 (56.6), 97.3 (97.6), 104.0~143.7 (m), 160.1 (dd, J1=250.5 Hz, J2=12.0 Hz), 162.2 (dd, J1=248.3, J2=12.0 Hz), 168.8 (173.9). MS m/z: 257, 183, 170, 140, 120, 115, 63, 45, 43. HRMS calcd for $C_{12}H_{13}F_2NO_3$ (M+): 257.0863; found: 257.0868.

C. General Procedure for Asymmetric Hydrogenation.

To a solution of $[Rh(COD)_2]OTf$ (2.0 mg, $4.27\times10^{-3}$ mmol) in toluene (3.4 mL) in a glove box was added a chiral ligand (0.047 mL of 0.1 M solution in toluene, $4.7\times10^{-3}$ mmol). After the mixture was stirred for 30 min, substrate 1 (0.427 mmol) was added. The hydrogenation was performed at room temperature under 10 atm of hydrogen for 24~36 hrs. The hydrogen pressure was released carefully and the reaction mixture was passed through a short silica gel column to remove the catalyst. The enantiomeric excesses were measured by HPLC without further purification;

(S)-N-Acetyl-O-Methoxymethyl-2-Phenylglycinol. $[\alpha]_D^{25}$=+64.6 (c 1.2, $CHCl_3$); $^1$H NMR (200 MHz, $CDCl_3$) δ 2.00 (s, 3H), 3.23 (s, 3H), 3.79 (d, J=4.97 Hz, 2H), 4.57 (m, 2H), 5.18 (m, 1H), 6.54 (br-d, J=7.58 Hz, 1H), 7.23~7.32 (m, 5H). $^{13}$C NMR ($CDCl_3$) δ 23.7, 53.2, 55.8, 70.8, 97.0, 127.2, 127.9, 128.9, 140.1, 170.0. MS m/z: 223, 193, 161, 148, 120, 106, 77, 45; HRMS calcd for $C_{12}H_{17}NO_3$ (M+): 223.1208; found: 223.1209.

(S)-N-Acetyl-O-Methyl-2-Phenylglycinol. $[\alpha]_D^{25}$=+73.3 (c 0.95, $CHCl_3$); $^1$H NMR (300 MHz, $CDCl_3$) δ 2.03 (s, 3H), 3.35 (s, 3H), 3.65 (d, J=4.73 Hz, 2H), 5.16 (m, 1H), 6.22 (br, 1H), 7.26~7.36 (m, 5H). $^{13}$C NMR ($CDCl_3$) δ 23.3, 52.5, 59.0, 74.9, 126.7, 127.4, 128.5, 139.8, 169.6. MS m/z: 193, 162, 148, 134, 106, 91, 77, 43; HRMS calcd for $C_{11}H_{15}NO_2$ (M+): 193.1103; found: 193.1099.

(S)-N-Acetyl-O-Methoxymethyl-2-(4-Phenylphenyl) glycinol. $[\alpha]_D^{25}$=+101.6 (c 1.0, $CHCl_3$); $^1$H NMR (360 MHz, $CDCl_3$) δ 1.97 (s, 3H), 3.20 (s, 3H), 3.73 (m, 5H), 4.51~4.56 (m, 2H), 5.05~5.10 (m, 1H), 6.14 (brd, J=7.45 Hz, 1H), 6.79~6.81 (m, 2H), 7.17~7.21 (m, 2H). $^{13}$C NMR ($CDCl_3$) δ 22.2, 51.3, 54.2, 54.3, 69.4, 95.5, 112.8, 127.0, 130.9, 157.8, 168.7. MS m/z: 243, 228, 198, 184, 142, 127, 69, 45; HRMS calcd for $C_{18}H_{21}NO_3$ (M+):299.1521; found: 299.1513.

(S)-N-Acetyl-O-Methoxymethyl-2-(4-Methoxyphenyl) glycinol. $[\alpha]_D^{25}$=+84.1 (c 1.0, $CHCl_3$); $^1$H NMR (300 MHz, $CDCl_3$) δ 2.02 (s, 3H), 3.28 (s, 3H), 3.84~3.87 (m, 2H), 4.59~4.65 (m, 2H), 5.24 (m, 1H), 6.56 (br-d, J=7.76 Hz, 1H), 7.26~7.58 (m, 9H). $^{13}$C NMR ($CDCl_3$) δ 23.3, 52.5, 55.4, 70.4, 96.7, 127.0, 127.2, 127.3, 128.7, 138.7, 140.4, 140.7, 142.0, 169.7. MS m/z: 222, 191, 178, 162, 150, 136, 121, 109, 91, 77, 65, 43; HRMS calcd for $C_{13}H_{19}NO_4$ (M+): 253.1314; found: 253.1309.

(S)-N-Acetyl-O-Methoxymethyl-2-(2-Naphthyl)glycinol. $[\alpha]_D^{25}$=+105.2 (c 1.1, $CHCl_3$); $^1$H NMR (300 MHz, $CDCl_3$) δ 2.05 (s, 3H), 3.24 (s, 3H), 3.84~3.93 (m, 2H), 4.59 (q, J=6.62 Hz, 2H), 5.35 (m, 1H), 6.61 (br-d, J=7.89 Hz, 1H), 7.43~7.47 (m, 3H), 7.78~7.81 (m, 4H). $^{13}$C NMR ($CDCl_3$) δ 22.3, 51.8, 54.4, 69.3, 95.7, 123.9, 124.5, 124.9, 125.1, 126.6, 126.9, 127.3, 131.8, 132.2, 118.1, 168.7. MS m/z: 273, 242, 213, 198, 156, 129, 102, 77, 43; HRMS calcd for $C_{16}H_{19}NO_3$ (M+): 273.1365; found: 273.1366.

(S)-N-Acetyl-O-Methoxymethyl-2-(4-Chlorophenyl) glycinol. $[\alpha]_D^{25}$=+81.2 (c 1.0, $CHCl_3$); $^1$H NMR (300 MHz, $CDCl_3$) δ 2.00 (s, 3H), 3.23 (s, 3H), 3.75~3.78 (m, 2H), 4.57 (d, J=6.51 Hz, 2H), 5.11~5.13 (m, 1H), 6.52 (br-d, J=7.28 Hz, 1H), 7.23~7.29 (m, 4H). $^{13}$C NMR ($COCl_3$) δ 23.7, 52.7, 55.9, 70.7, 97.1, 127.0, 128.6, 129.0, 133.6, 138.8, 170.1. MS m/z: 258 (260), 227 (229), 182 (184), 140 (142), 102, 77, 45; HRMS calcd for $C_{12}H_{16}ClNO_3$ (M+): 259.0789 (37Cl), 257.0819 (35Cl); found: 259.0820, 257.0823.

(S)-N-Acetyl-O-Methoxymethyl-2-(4-Methylphenyl) glycinol. $[\alpha]_D^{25}$=+78.6 (c 1.0, $CHCl_3$); $^1$H NMR (300 MHz, $CDCl_3$) δ 2.00 (s, 3H), 3.26 (s, 3H), 3.78 (d, J=5.02 Hz, 2H), 4.58 (q, J=6.50 Hz, 2H), 5.11~5.17 (m, 1H), 6.47 (br, 1H), 7.10~7.26 (m, 4H). $^{13}$C NMR ($CDCl_3$) δ 21.0, 23.2, 52.4, 55.3, 70.3, 96.6, 126.6, 129.1, 136.6, 137.0, 169.5. MS m/z: 238, 206, 175, 162, 133, 120, 91, 77, 45; HRMS calcd for $C_{13}H_{19}NO_3$ (M+): 237.1365; found: 237.1362.

(S)-N-Acetyl-O-Methoxymethyl-2-(4-Fluorophenyl) glycinol. $[\alpha]_D^{25}$=+63.8 (c 1.1, $CHCl_3$); $^1$H NMR (300 MHz, $CDCl_3$) δ 1.95 (s, 3H), 3.20 (s, 3H), 3.70~3.72 (m, 2H), 4.54 (q, J=6.58 Hz, 2H), 5.11 (m, 1H), 6.84 (br, 1H), 6.92~6.98 (m, 2H), 7.23~7.28 (m, 2H). $^{13}$C NMR ($CDCl_3$) δ 23.1, 52.2, 55.3, 70.3, 96.5, 115.2 (d, J=21.2 Hz), 128.4 (d, J=7.85 Hz), 135.6, 162.0 (d, J=245.3 Hz), 169.7. MS m/z: 210, 179, 166, 138, 124, 109, 75, 45, 43; HRMS calcd for $C_{12}H_{16}FNO_3$ (M+): 241.1114; found: 241.1113.

(S)-N-Acetyl-O-Methoxymethyl-2-(2,4-Difluorophenyl) glycinol. $[\alpha]_D^{25}$=+50.1 (c 1.05, $CHCl_3$); $^1$H NMR (360 MHz, $CDCl_3$) δ 1.94 (s, 3H), 3.16 (s, 3H), 3.69 (m, 2H), 4.49 (q, J=6.52 Hz, 2H), 5.31 (m, 1H), 6.62 (br, 1H), 6.68~6.7 (m, 2H), 7.19~7.23 (m, 1H). $^{13}$C NMR ($CDCl_3$) δ 22.1, 47.0, 54.3, 48.4, 95.6, 103.0 (t, J=25.1 Hz), 110.1 (dd, J1=3.08 Hz, J2=20.9 Hz), 121.8 (m), 128.6 (m), 161.3 (dd, J1=12.4 Hz, J2=248.6 Hz), 159.5 (dd, J1=12.0 Hz, J2=248.6 Hz), 168.6. MS m/z: 241, 238, 224, 182, 152, 115, 43; HRMS calcd for $C_{12}H_{15}F_2NO_3$ (M+): 259.1020; found: 259.1024.

Determination of Enantiomeric Excesses by Chiral HPLC.

Column: (R,R)-Poly Whelk-01 from Regis Technologies, Inc. Particle size: 5.0 um. Column dimensions: 25 cm (length)×0.46 cm (i.d.). Column temperature: 25° C. Racemic samples were obtained by hydrogenation using Pd on Carbon or $Rh(PPh_3)_3Cl$ as catalyst.

N-Acetyl-O-Methoxymethyl-2-Phenylglycinol (HPLC, 1.0 mL/min, 2-PrOH/hexane=3:7), (R) $t_1$=11.1 min, (3) $t_2$=17.8 min.

N-Acetyl-O-Methyl-2-Phenylglycinol (HPLC, 1.0 mL/min, 2-PrOH/hexane=5:95), (R) $t_1$=53.6 min, (S) $t_2$=129.2 min.

N-Acetyl-O-Methoxymethyl-2-(2-Naphthyl)glycinol (HPLC, 1.0 mL/min, 2-PrOH/hexane=4:6 for 20 min, then 3:7), (R) $t_1$=13.7 min, (S) $t_2$=47.5 min.

N-Acetyl-O-Methoxymethyl-2-(4-Chlorophenyl)glycinol (HPLC, 1.0 mL/min, 2-PrOH/hexane=2:8), (R) $t_1$=15.2 min, (S) $t_2$=38.3 min.

N-Acetyl-O-Methoxymethyl-2-(4-Methoxyphenyl) glycinol (HPLC, 1.0, mL/min, 2-PrOH/hexane=2:8 for 30 min, then 1:1), (R) $t_1$=21.7 min, (S) $t_2$=48.8 min.

N-Acetyl-O-Methoxymethyl-2-(4-Methylphenyl) glycinol (HPLC, 1.0 mL/min, 2-PrOH/hexane=3:7), (R) $t_1$=11.2 min, (S) $t_2$=20.6 min.

N-Acetyl-O-Methoxymethyl-2-(4-Phenylphenyl)glycinol (HPLC, 1.0 mL/min, 2-PrOH, (R) $t_1$=16.8 min, (S) $t_2$=27.0 min.

N-Acetyl-O-Methoxymethyl-2-(4-Fluorophenyl)glycinol (HPLC, 1.0 mL/min, 2-PrOH/hexane=5:95), (R) $t_1$=59.9 min, (S) $t_2$=147.0 min.

N-Acetyl-O-Methoxymethyl-2-(2,4-Difluorophenyl) glycinol (HPLC, 1.0 mL/min, 2-PrOH/hexane=5:95), (R) $t_1$=53.5 min, (S) $t_2$=72.5 min.

Determination of Absolute Configuration

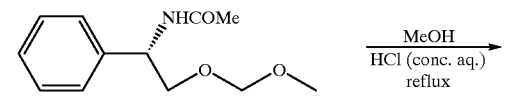

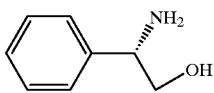

To a solution of a reduction product, N-acetyl-O-methoxymethyl-2-phenylglycinol (40 mg, 0.18 mmol) in methanol (2 mL) was added 4 drops of conc. hydrochloric acid at room temperature. The reaction mixture was heated under refluxing for 6 h. The reaction mixture was then cooled to room temperature, and solvent was evaporated under vacuum. The residue was treated with 0.5 N NaOH at 0° C., and extracted with $CH_2Cl_2$. Combined organic layer was dried over $Na_2SO_4$. Evaporation of the solvent gave phenylglycinol as a white solid: 20 mg, 81.4% yield. $^1$H NMR (360 MHz, $CDCl_3$) δ 2.33 (br, 3H), 3.46~3.51 (m, 1H), 3.65~3.68 (m, 1H), 3.96~3.99 (m, 1H), 7.19~7.30 (m, 5). $[\alpha]_D^{25}$=+47.5 (c 0.6, $CHCl_3$). Standard sample from Aldrich, (R)-phenylglycinol: $[\alpha]_D^{25}$=−51.7 (c 0.75, $CHCl_3$).

The absolute configurations of other hydrogenation products were assigned as (S)-isomer based on the HPLC analysis and optical rotation.

ADDITIONAL EXAMPLES

Other chiral ligands and asymmetric reactions have been explored. These include asymmetric hydrogenation of enol esters, ethers and amides by Rh-PennPhos catalysts, hydrogenation of acrylic acids, Ni-cataiyzed asymmetric hydrovinylation with new monophosphines, Rh-catalyzed asymmetric hydroformylation with new phosphine ligands and some asymmetric carbon—carbon forming reactions such as allylic alkylation, Diels-Alder, Heck and Aldol reactions. In the asymmetric hydrogenation area, other substrates can lead to β-amino acids and chiral glycines are possible.

Example 5. Hydrogenation of β-Keto Esters

We have been interested in the design and syntheses of efficient chiral bisphosphine ligands for catalytic asymmetric reactions. One approach for our ligand design is to restrict the conformational flexibility by introducing a rigid ring structure in the backbone of our bisphosphine ligands (Zhu, G. et al., J. Am. Chem. Soc. 1997 119 1799; Zhu, G. et al., J. Am. Chem. Soc. 1997 119 3836; Chen, Z. et al., J. Org. Chem. 1997 62 4521; Zhu, G. et al., Org. Chem. 1998 120 3133), For example, the chiral 1, 4bisphosphine, (2R, 2'R)-bis(diphenylphosphino)-(R,1'R)-dicyclopentane (1, (R,R)-BICP). In this BICP ligand system, four stereogenic centers in a bicyclopentyl backbone efficiently restrict the conformational flexibility. Our preliminary studies revealed that the rhodium complexes of the BICP ligand are efficient catalyst for the asymmetric hydrogenation of α-acylaminoacrylic acids and enamides. However, early attempts to develop efficient catalyst systems derived from BICP ligand for the asymmetric hydrogenation of ketone and imine substrates have been unsuccessful. It is well accepted that both steric and electronic properties of chiral ligands have profound effects on the enantioselectivity and reactivity for asymmetric reactions. We prepared a modified BICP ligand 2 with 3,5-dimethyl substituents on the diphenylphosphino groups and observe different meta effects in asymmetric ruthenium catalyzed hydrogenation, Pd-catalyzed allylic alkylation and Heck reactions.

The modified BICP ligand 72 was synthesized using a similar route reported for the (R,R)-BICP ligand (see Scheme 2). Chiral diol 74 was made by asymmetric hydroboration of diene 73. The modified chiral hydroboration reagent (IpcB(Cl)H) by H. C Brown's group gave better yield than the previous reagent ($IpcBH_2$). Bismesylate 75 was obtained in high yield, which was reacted directly with lithium diphenylphosphide affording the desired bisphosphine 2 in good yield. Selected data for the bisphosphine 2: $^1$H NMR ($CDCl_3$, 300 MHz) δ 7.25~7.21 (m, 4H), 7.07 (s, 2H), 7.00~6.98 (m, 4H), 6.94 (s, 2H), 2.40 (s, 12H), 2.34 (s, 12H), 2.33~2.19 (m, 2H), 1.83~1.29 (m, 14H), $^{13}$C NMR ($CDCl_3$) δ 139.9~125.2 (Ph), 47.6~47.1 (m), 39.1 (d, 14.0 Hz), 30.9 (m), 22.4 (m), 21.4, 21.3; $^{31}$P NMR($CDCl_3$) δ −16.9.

Ruthenium catalyzed hydrogenation of β-keto esters was chosen to test the efficiency of this modified BICP ligand 2. The asymmetric hydrogenation of β-keto esters provides an efficient method for synthesizing optically active β-hydroxy carboxylic esters which are an extremely important compounds for natural product syntheses. Catalyst precursor $[(Mod-BICP)RuBr_2]_2$ was prepared by reacting the modified BICP ligand 2 with $[(COD)Ru(2-methylallyl)_2]$ followed by treatment of methanoic HBr in acetone according to Genet's method (Genet, J. P. et al., Tetrahedron: Asymmetry 1994, 5, 665). Methyl acetoacetate was used as the model substrate for the screening of the reaction conditions. When the hydrogenation of methyl acetoacetate was carried out in methanol under 1 atmosphere of hydrogen using the Ru-catalyst described above, 93.9% enantiomeric excess was achieved at 65° C. for the hydrogenation product with dimethyl ketal of methyl acetoacetate as the by-product (entry 1, Table 7). The formation of the byproduct, β-dimethyl ketal of methyl acetoacetate, can be suppressed by using water as the co-solvent (Burk, M. J. et al., J. Am. Chem. Soc. 1995 117 4423), however at the expense of reactivity and enantioselectivity. Our studies showed that using 10% water in methanol (v/v) as the reaction solvent gave the best result at room temperature under 60 psi of hydrogen in terms of both reactivity and selectivity for the hydrogenation of methyl acetoacetate (entry 3). For comparison, the analogous Ru-(R,R)-BICP complex was prepared in the same way, and the hydrogenation of methyl acetoacetate proceeded in 77.6% ee under the same conditions (water/methanol=1:9, 60 psi of hydrogen, 0.2 mol % catalyst, room temperature). This result indicates that the modified BICP ligand (2) with 3,5-dimethyl substituents on the diphenylphosphino groups have positive meta effects on the ruthenium catalyzed asymmetric hydrogenation of β-keto esters.

Under our standard conditions as described above (water/methanol=1:9, 60 psi of hydrogen, 0.2 mol % catalyst, room temperature), a variety of β-keto esters can be hydrogenated smoothly affording the corresponding β-hydroxy esters with high enantioselectivities using a $RuBr_2$ complex bearing the modified BICP ligand 2. 62 -Keto esters with bulkier ester group (R') gave slightly lower enantioselectivities (entries 6, 7). To examine which tautomer of β-keto esters (keto or enol tautomer) was involved in the Ru-catalyzed hydrogenation, methyl 2,2-dimethylacetoacetate was selected as a substrate for the hydrogenation. Under the standard reaction conditions, the hydrogenation of methyl 2,2-dimethylacetoacetate went smoothly with 92.9% enantiomeric excess in slightly lower reactivity than other substrates without 2-substituents (entry 11). Because this β-keto ester does not have the enol tautomer, this result indicates that the hydrogenation is direct reduction of the C—O double bond rather than reduction of the C—C double bond of the enol tautomer. This observation is similar to some other ruthenium catalyst systems (Noyori, R. et al., J. Am. Chem. Soc. 1989 111 9134).

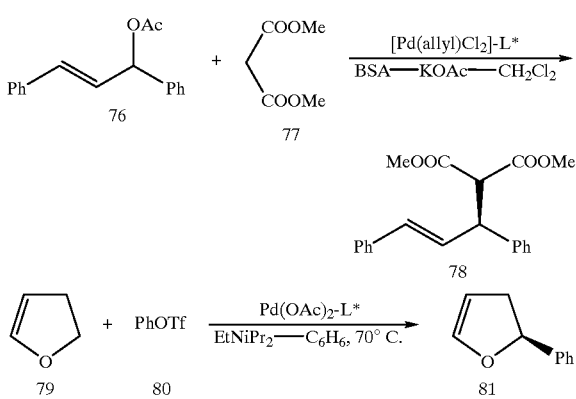

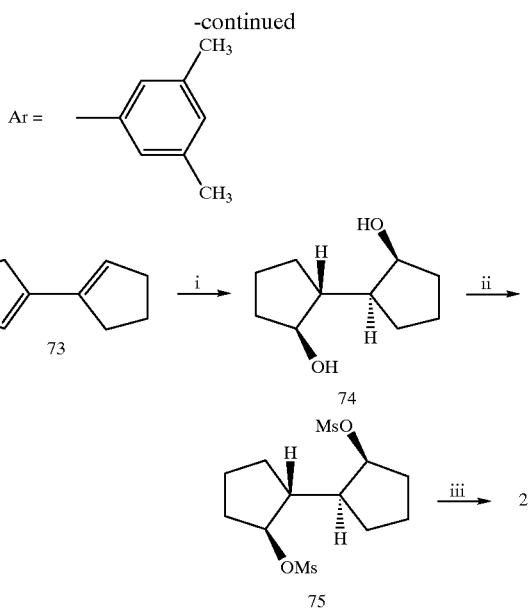

a) IpcB(Cl)H, Et$_2$O, b) H$_2$O$_2$, NaOH (4 M aq.)
b) MsCl, Et$_3$N, CH$_2$Cl$_2$
LiPAr$_2$, THF

The extent of the 3,5-dimethyl meta effects on the enantioselectivities is dependent on the type of reaction. For example, higher enantiomeric excess was observed for the Pd-catalyzed allylic alkylation of the classic 1,3-diphenylallyl acetate 76 using modified BICP 2 compared to using BICP 1 (74.1% ee with 95% yield for ligand 2 vs. 47.0% ee with 95% yield for ligand 1). However, the modified BICP ligand 2 showed a negative meta effect in the Heck reaction between dihydrofuran 79 and phenyl triflate 80. Lower ee was obtained with the modified ligand 2 than with BICP (1) (52.4% ee with 82.1% yield for ligand 2 vs. 66.2% ee with 77.5% yield for ligand 1) affording compound 81 as the only product.

General Procedure for Asymmetric Hydrogenation of β-Keto esters.

BICP (0.01 mol) and Ru(COD)(2-methylallyl)$_2$ (0.01 mol) were placed in a 10 ml Schlenk tube and the vessel was purged With argon. 2 mL of anhydrous acetone were added. To this suspension was added methanolic HBr (0.11 ml of a 0.29 M solution) and the suspension was stirred 30 min at room temperature. The solvent was thoroughly evaporated under vacuum and the Ru(BICP)Br$_2$ obtained was used immediately. The solution of appropriate substrate (1 mmol) in degassed solvent (2 ml) was placed in a 10 ml Schlenck tube and degassed by 3 cycles of vacuum/argon. This mixture was added to the catalyst (1%) in a glass vessel and placed under argon in 300 ml stainless steel autoclave. The Argon atmosphere was replaced with hydrogen. The hydrogenations were run under the reaction conditions given. The solvent was removed under pressure. Conversion and ee are determined by chiral GC column β-DEX 120 and γ-DEX 225.

Scheme 2

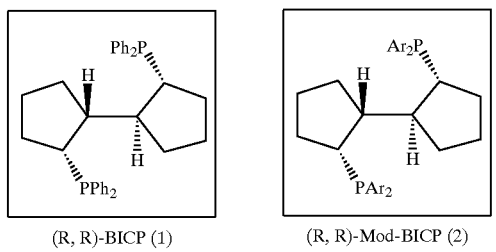

(R, R)-BICP (1)        (R, R)-Mod-BICP (2)

TABLE 7

Ruthenium Catalyzed Asymmetric hydrogenation of β-Keto Esters[a]

| Entry | R | R' | Pressure (psi) | Temp (° C.) | Conversion (%)[b] | ee (%)[b,c] |
|---|---|---|---|---|---|---|
| 1[d] | Me | Me | 14.7 | 65 | 100 | 93.9 (R) |
| 2 | Me | Me | 60 | 35 | 100 | 91.0 (R) |
| 3 | Me | Me | 60 | 25 | 100 | 90.8 (R) |
| 4[e] | Me | Me | 60 | 25 | 100 | 77.6 (R) |
| 5 | Me | Et | 60 | 25 | 100 | 90.7 (R) |
| 6 | Me | i-Pr | 60 | 25 | 100 | 77.9 (R) |
| 7 | Me | t-Bu | 60 | 25 | 100 | 81.3 (R) |
| 8 | Et | Me | 60 | 25 | 100 | 90.0 (R) |
| 9 | Pr | Et | 60 | 25 | 100 | 91.2 (R) |
| 10 | i-Pr | Et | 60 | 25 | 100 | 90.1 (R) |
| 11 | | | 60 | 25 | 92.7 | 92.7 (R) |

[a]The reaction was carried out in 10% water in methanol (v/v) in the presence of 0.2 mol % of [Ru(MOD-BICP(2))Br$_2$]$_2$ made by reacting the modified BICP ligand 2 with [(COD)Ru(2-methylallyl)$_2$] followed by treatment of methanoic HBr in acetone. Long reaction time (2–3 days) was used to ensure the completion of the reaction and the reactions with some substrates may be completed in shorter time.
[b]Determined by GC using β-DEX-225 or β-DEX-225 columns.
[c]Absolute configuration was determined by comparing the optical rotation with the reported value.
[d]Methanol was used as pure solvent in this reaction.
[e](R,R)-BICP 1 was used as ligand to replace the modified BICP ligand 2.

Example 6. Hydrogenation of Imines

Asymmetric hydrogenation of C=N bonds is an attractive method for synthesis of chiral amines. In contrast to numerous highly enantioselective catalytic systems for hydrogenation of C=C bonds, hydrogenations of prochiral imines only give modest enantiomeric excesses with most catalyst systems. A highly enantioselective hydrogenation catalyst was reported by Buchwald's group using a chiral titanocene system, albeit with low turnovers. High enantioselectivity was achieved by Rh-catalyzed hydrogenation of functionalized imines by a DuPont research group. A more recent approach by Noyori et al uses Ru-chiral diamine complexes as effective catalysts for the enantioselective transfer hydrogenation of imines with triethylammonium formate. Extremely high activity has been observed for the asymmetric reduction of imines using a chiral ferrocenyldiphosphine-iridium catalyst. However, achieving high activity and enantioselectivity as well as broad substrate scope still represent a challenge in this important research area. Furthermore, the effect of various additives in this type of reactions is not well understood. Herein, we report our studies on the additive effects (Table 8) of an iridium-catalyzed asymmetric hydrogenation of imines using BICP (1) as the chiral ligand (Zhu, G. et al., J. Am. Chem. Soc. 1997 119 1799).

2,3,3-Trimethylindolenine was chosen as a model substrate. It is generally accepted that neutral metal (Rh(I) or Ir(I)) complexes usually show higher enantioselectivity than the corresponding cationic species, and that iodide ion can prevent the deactivation of the iridium catalyst. In our initial study, the asymmetric hydrogenation of imine 82 was carried out under 1000 psi $H_2$ with an Ir (I) complex catalyst prepared in situ from $[Ir(COD)Cl]_2$ and (R,R)-BICP (molar ratio: imine/Ir/BICP=100/1/1.2). Interestingly, we have found that using iodide as an additive in a mixture of MeOH and benzene (1:1) gave both low conversion and enantioselectivity (entries 1, 2). Protic amine, documented as an effective promoter in an Ir-BINAP catalytic system, also did not work well in our system (entries 3, 4). We therefore focused our attention on other additives for the hydrogenation reaction.

Inspired by Achiwa's work (Morimoto, T. et al., Tetrahedron: Asymmetry 1995 6 2661) showing that imides can improve both the catalytic activity and enantioselectivity of bisphosphine-iridium (I) catalyzed hydrogenation of certain imines, we found that phthalimide has a dramatic effect on the enantioselectivity of our Ir-BICP catalytic system for the hydrogenation of trimethylindolenine. In the presence of phthalimide (4 mol %), imine 82 was hydrogenated smoothly with 92.2% ee in toluene using an iridium catalyst generated in situ from $[Ir(COD)Cl]_2$ and (R,R)-BICP 1 (entry 6). A control experiment showed that phthalimide is an important additive (entry 10). Systematic studies show that the presence of 4 mol % of phthalimide gave the optimal results (entries 5–10). A strong solvent effect was observed in this catalytic system. While polar solvents such as alcohol or DMF gave poor results (entries 11, 12), toluene and $CH_2Cl_2$ were found to be preferred solvents for this catalytic system (entries 6, 13).

TABLE 8

Asymmetric hydrogenation of 2,3,3-trimethylindolenine catalyzed by an Ir(I)-BICP complex[a]

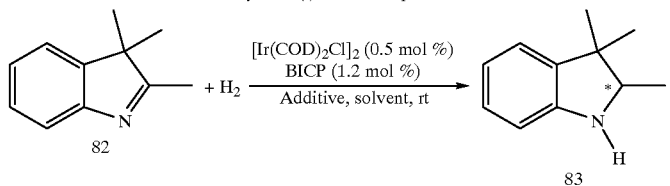

| Entry | Solvent | Additive (% mol) | Press. (psi) | Time (h) | Conv. (%)[b] | ee (%)[b] |
|---|---|---|---|---|---|---|
| 1 | $C_6H_6$—MeOH | n-$Bu_4$NI (2) | 1050 | 72 | 2.1 | 34.5 (−)[c] |
| 2 | $C_6H_6$—MeOH | $BiI_3$ (0.65) | 1050 | 72 | 55.0 | 27.0 (−) |
| 3 | MeOH | (R)-α-methylbenzylamine (5) | 1050 | 72 | 3.3 | 8.5 (−) |
| 4 | MeOH | (S)-α-methylbenzylamine (5) | 1050 | 72 | 1.4 | 11.4 (−) |
| 5 | Toluene | Phthalimide (2) | 1000 | 72 | 92.0 | 75.1 (−) |
| 6 | Toluene | Phthalimide (4) | 1000 | 65 | 97.8 | 92.2 (−) |
| 7 | Toluene | Phthalimide (6) | 1000 | 65 | 100 | 92.2 (−) |
| 8 | Toluene | Phthalimide (8) | 1000 | 65 | 100 | 91.4 (−) |
| 9 | Toluene | Phthalimide (16) | 1000 | 65 | 98.7 | 88.1 (−) |
| 10 | Toluene | None | 1000 | 96 | 100 | 78.1 (−) |
| 11 | DMF | Phthalimide (4) | 1000 | 65 | 98.1 | 18.7 (−) |
| 12 | $C_6H_6$—MeOH | Phthalimide (4) | 1000 | 100 | 26.1 | 14.4 (+) |
| 13 | $CH_2Cl_2$ | Phthalimide (4) | 1000 | 100 | 100 | 93.9 (−) |
| 14[d] | $CH_2Cl_2$ | Phthalimide (4) | 1000 | 100 | 100 | 95.1 (−) |
| 15 | Toluene | Succinimide (4) | 1000 | 65 | 99.2 | 88.3 (−) |
| 16 | Toluene | Hydanton (4) | 1000 | 65 | 100 | 90.1 (−) |
| 17 | Toluene | 2,3-Naphthalene-dicarboximide (4) | 1000 | 70 | 100 | 91.7 (−) |
| 18 | Toluene | 4,5-dichlorophthalimide (4) | 1000 | 70 | 100 | 91.8 (−) |
| 19 | Toluene | N-Me-phthalimide (4) | 1000 | 65 | 100 | 90.0 (−) |
| 20 | Toluene | N-K-phthalimide (4) | 1000 | 68 | 71.8 | 37.0 (−) |
| 21 | Toluene | N-Br-phthalimide (4) | 1000 | 70 | 100 | 31.8 (−) |
| 22 | Toluene | Phthalic anhydride (4) | 1000 | 68 | 100 | 83.4 (−) |
| 23 | Toluene | 1,3-indandione (4) | 1000 | 96 | 100 | 90.2 (−) |

[a]Reaction conditions: $[Ir(COD)Cl]_2$: (R,R)-BICP:imine = 1:2.4:200, [imine] = 0.15 M.
[b]Determined by GC using a Supelco β-DEX-225 column.

TABLE 8-continued

Asymmetric hydrogenation of 2,3,3-trimethylindolenine catalyzed by an Ir(I)-BICP complex[a]

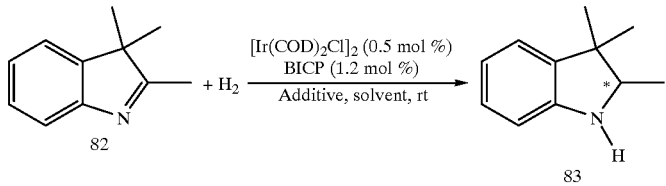

| Entry | Solvent | Additive (% mol) | Press. (psi) | Time (h) | Conv. (%)[b] | ee (%)[b] |
|---|---|---|---|---|---|---|

[c]Optical rotation was taken in ether.
[d]This reaction was carried out at 0° C.

The best enantioselectivity (95.1% ee) with complete conversion for the hydrogenation of imine 82 was found when the reaction was carried out at 0° C. in $CH_2Cl_2$ (entry 14). Various imides such as succinimide, hydantoin, 2,3-naphthalenedicarboximide and 4,5-dichlorophthalimide can be used as an additive (4 mol %) to improve the enantioselectivity of Ir-BICP catalyzed hydrogenation of 2,3,3-trimethylindolenine 82 (entries 15–18).

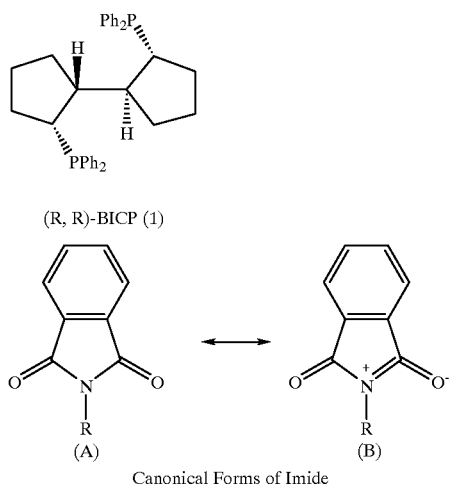

(R, R)-BICP (1)

Canonical Forms of Imide

Colquhoun and co-workers have reported that imidato ligands, derived from imides [$(RCO)_2N^-$], behave as a pseudo-halogen in terms of their σ-acceptor and π-donor properties (Adams, H. et al., J. Chem. Soc., Dalton Trans. 1986, 813). To investigate whether an ionic Ir—N bond accounts for the additive effect of phthalimide, we replaced phthalimide with N-methyl phthalimide. Surprisingly, the hydrogenation still went smoothly and gave similar enantioselectivity as found with phthalimide (entry 19). However, using potassium phthalimide as the additive, the reaction not only gave low enantioselectivity but also low conversion (entry 20). These results indicate that the additive effect of phthalimide does not stem from an Ir—N bonded complex. One possible explanation for the observed results is that the canonical form of phthalimide involving a C—O single bond may coordinate to the Ir complex. Introduction of electron withdrawing groups adjacent to the N atom will disfavor the canonical form (B). Indeed, when N-bromophthalimide was used as an additive, much lower enantioselectivity was observed (entry 21). Furthermore, phthalic anhydride, which forms the canonical form (B) with difficulty, had almost no effect on the enantioselectivity for this reaction (entry 22). On the other hand, 1,3-indandione can form a more stable enol form through keto-enol tautomerism. The presence of this additive increased the enantioselectivity of hydrogenation of imine 82 (entry 23). Based on these results, we speculate that those canonical forms in imides and 1,3-indandione have significant contributions to the dramatic additive effect in the Ir-catalyzed hydrogenation of imines.

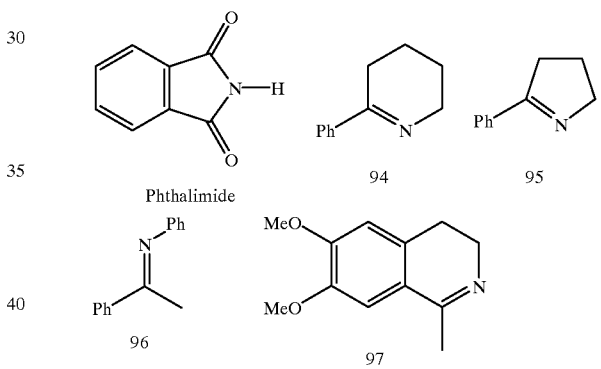

Phthalimide

The additive effect of imides found in this study and the enantioselectivity are very sensitive to the substrate structure. When other cyclic and non-cyclic imines were used as substrates, the Ir-BICP catalyst did not give the same high enantioselectivity as found for 2,3,3-trimethylindolenine. In the presence of phthalimide (4 mol %), the following enantiomeric excesses were obtained for different substrates. 94 (64.7% ee, 100% conversion); 95 (56.3% ee, 12.8% conversion); 96 (13.7% ee, 68.2% conversion); 97 (4.0% ee, 94.6% conversion). Further study showed that different imines needed other additives to achieve optimal results. For example, imine 97 can be hydrogenated in 41.3% ee with high conversion in methanol using benzylamine (5 mol %) as the additive. In certain cases, addition of acids such as HOAc, or $H_2SO_4$ can improve the reactivity of the hydrogenation, but the enantioselectivity did not change significantly. It is clear that Ir-catalyzed hydrogenation of imines is a complicated catalytic system and good understanding of this process is presently not available.

In conclusion, remarkable additive effects of imides and 1,3-indandione were found in iridium-BICP complex catalyzed asymmetric hydrogenation of imines.

Example 7. Hydrogenation Of Enol Esters

Excellent enantioselectivities have been obtained using Rh-PennPhos catalysts. This is especially true for cyclic enol esters. At the same condition, BINAP and DuPhos ligands are not efficient and effective.

Asymmetric Hydrogenation Of Cyclic Enol Esters
Catalyst=[Rh(COD)]$_2$[BF$_4$] (0.5 mol %)+Chiral Bisphosphine, 25 psi H$_2$, in THF

| Substrate | Ligand | % ee | Substrate | Ligand | % ee |
|---|---|---|---|---|---|
| (OAc-tetrahydronaphthalene) | BINAP<br>Me-DuPhos<br>Me-PennPhos | 18<br>12<br>99 | (OAc-indene) | BINAP<br>Me-DuPhos<br>Me-PennPhos | 64<br>84<br>97 |
| (dimethyl-OAc-tetrahydronaphthalene) | BINAP<br>Me-DuPhos<br>Me-PennPhos | 25<br>30<br>99 | (methyl-OAc-indene) | Me-PennPhos | 96 |

Example 8. Hydrogenation Of Enol Ethers

Excellent enantioselectivities have been obtained using Rh-PennPhos catalysts. At the same condition, BINAP and DuPhos ligands are not efficient and effective.

Asymmetric Hydrogenation Of Enol Ethers
Catalyst=[Rh(COD)]$_2$[BF$_4$] (0.5 mol %)+Chiral Phosphine, 25 psi H$_2$, in CH$_2$Cl$_2$

| Substrate | Ligand | % ee | Substrate | Ligand | % ee |
|---|---|---|---|---|---|
| (OMe-phenyl) | iPr-PennPhos<br>Et-PennPhos<br>Me-PennPhos<br>BINAP<br>Me-DuPhos | 94<br>89<br>86<br>46<br>57 | (OMe-tolyl) | iPr-PennPhos<br>Et-PennPhos<br>Me-PennPhos<br>BINAP<br>Me-DuPhos | 89<br>87<br>82<br>48<br>30 |
| (OMe-naphthyl) | iPr-PennPhos<br>Et-PennPhos<br>Me-PennPhos | 68<br>83<br>73 | (OMe-4-F-phenyl) | iPr-PennPhos | 90 |

Example 9. Hydrogenation Of Functionalized Alkenes

An important chiral drug, Naproxen, can be made in 89% ee using a Rh-MOD-BICP catalyst. Other alkenes can also be reduced using asymmetric hydrogenation methods.

Synthesis Of Naproxen

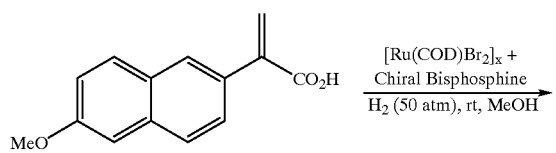

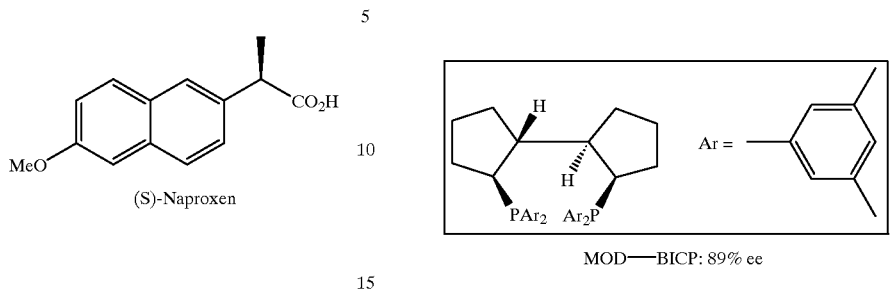

MOD—BICP: 89% ee

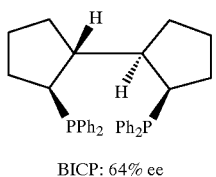

BICP: 64% ee

Example 10. Hydroformylation

Two benchmark ligands (BINAPHOS and UC-P2) have been reported in the literature and patent. A family of new chiral bisphosphites with rigid chiral diols are made. Unoptimized results of Rh-catalyzed asymmetric hydroformylation show good enantioselectivity and excellent regioselectivity.

Asymmetric Hydroformylation

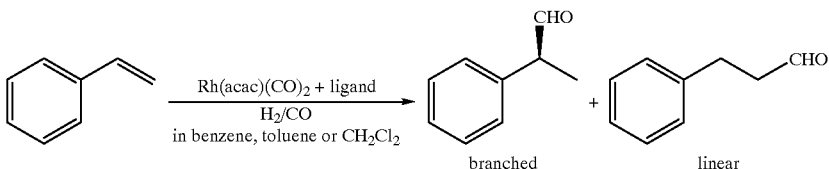

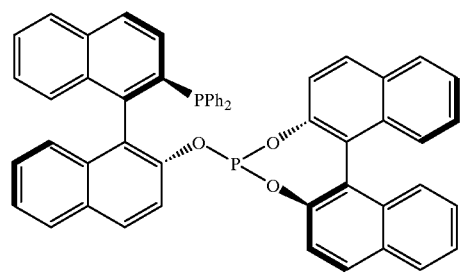

94% ee, b/l = 88/12
$CO/H_2$ pressure = 50 atm/50 atm, 60° C.
Nozaki et al., J. Am. Chem. Soc. (1997) 119 4413

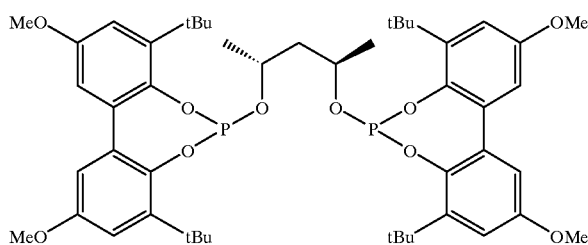

71% ee, b/l = 27/1
$CO/H_2$ pressure = 5 atm/5 atm, 50° C.
Up to 90% ee at optimized conditions
U.S. Pat. No. 5,491,266

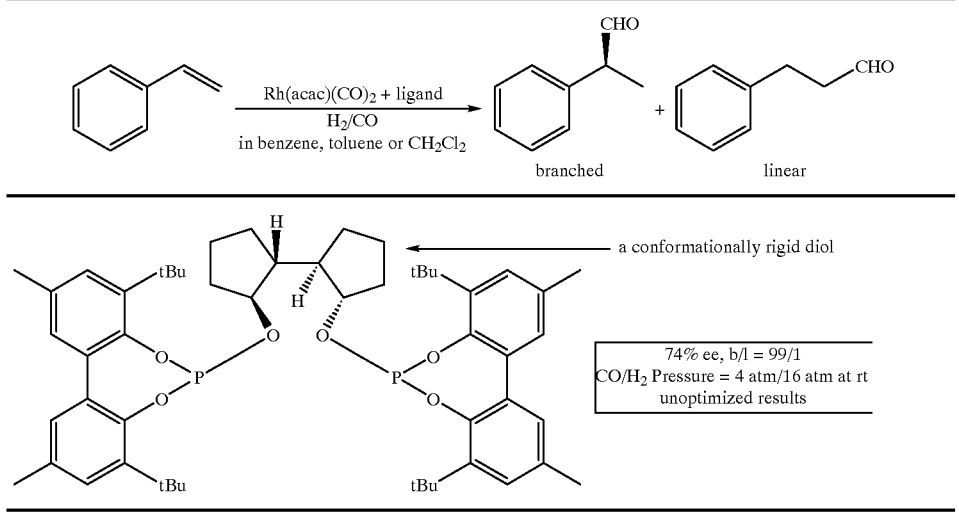

Example 11. Hydrovinylation

The conversion is generally good. Enantioselectivities can be measured by chiral GC. Substrates other than styrene also give good enantioselectivity. Hemilabile monophosphines with o-methoxy groups are made and they are more effective in this reaction.

Ni-Catalyzed Asymmetric Hydrovinylation

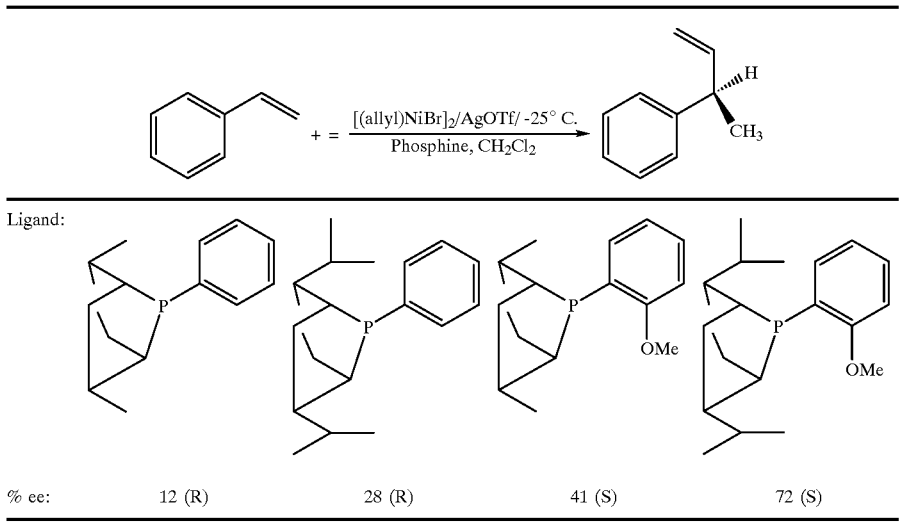

The foregoing written description relates to various embodiments of the present invention. Numerous changes and modifications may be made therein without departing from the spirit and scope of the invention as defined in the following claims.

What is claimed is:

1. A process comprising subjecting a substrate, which undergoes an asymmetric reaction in the presence of a catalyst to form a product, to said asymmetric reaction, wherein said asymmetric reaction is chosen from hydrogenation, hydride transfer, hydrosilylation, hydroboration, hydrovinylation, olefin metathesis, hydroformylation, hydrocarboxylation, allylic alkylation, cyclopropanation, Diels-Alder, Aldol, Heck, cycloaddition, and Michael addition reactions, wherein said catalyst, having an optical purity of at least 85% ee, comprises a transition metal and a chiral compound, and said chiral compound is chosen from L1, L2, L3, and L4 and corresponding enantiomers:

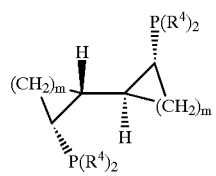

(L1)

-continued

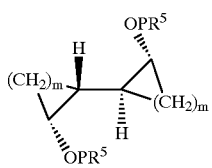
(L2)

wherein:

m ranges from 1 to 8 to form a ring, wherein the ring may be unsubstituted or substituted and may be part of a fused ring;

$R^4$ is unsubstituted or substituted aryl or alkyl;

$R^5$ is

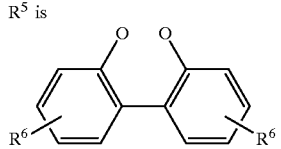

wherein each $R^6$ independently represents two substituents which are independently C1–C5 alkyl or alkoxy groups, each meta to the bond joining the phenyl rings;

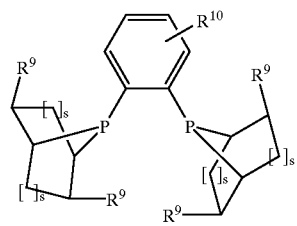
(L3)

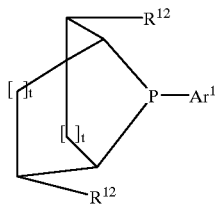
(L4)

wherein s ranges from 1 to 4;

t ranges from 1 to 4;

$R^9$ is unsubstituted or substituted aryl or alkyl;

$R^{10}$ is hydrogen, or one or more unsubstituted or substituted aryl or alkyl groups;

$R^{12}$ is one or more unsubstituted or substituted aryl or alkyl groups; and, $Ar^1$ is unsubstituted or substituted aryl.

2. A process according to claim 1, wherein said asymmetric reaction is chosen from hydrogenation reactions of a ketone, an imine, or an olefin.

3. A process according to claim 1, wherein said asymmetric reaction is chosen from hydrogenation reactions of an enamide, a β-keto ester, an enol acetate, or an enol ether.

4. A process according to claim 1, wherein the catalyst comprises one of following compounds 1–14:

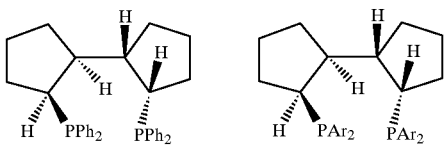

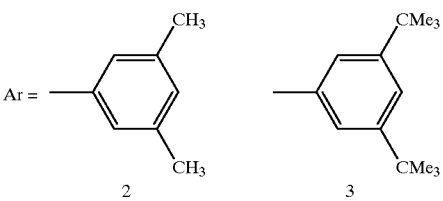

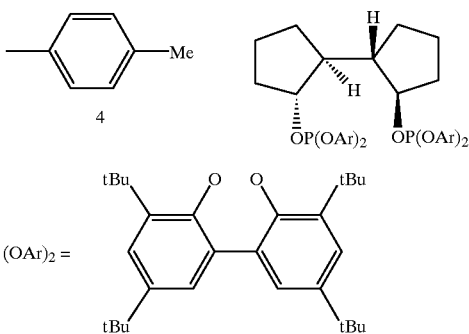

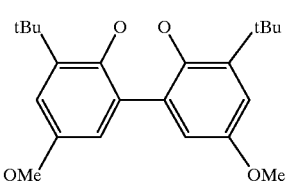

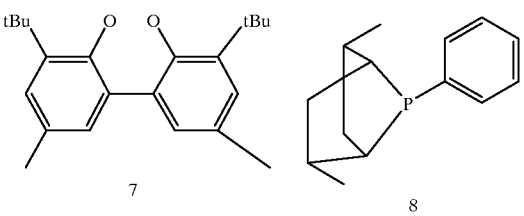

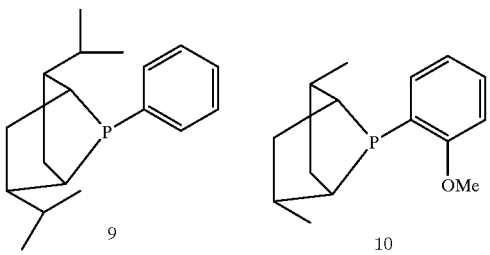

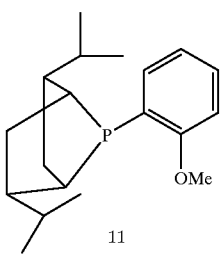

-continued

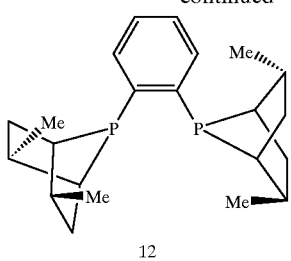

12

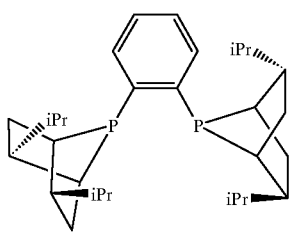

13

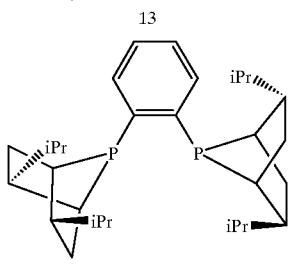

14

5. A process according to claim 1, wherein the substrate is of formula (S1) or (S2) to provide a product of formula (P1) or (P2):

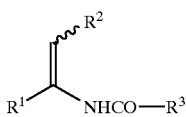
(S1)

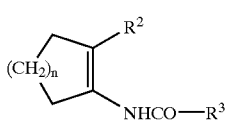
(S2)

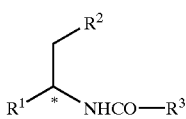
(P1)

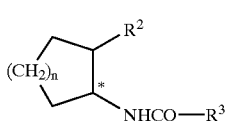
(P2)

wherein:

$R^1$ is hydrogen, or unsubstituted or substituted alkyl or aryl;

$R^2$ is hydrogen, unsubstituted or substituted C1–C12 alkyl, unsubstituted or substituted aryl, —COOR$^{18}$, wherein $R^{18}$ is unsubstituted or substituted C1–C12 alkyl or aryl, or OR$^{19}$, wherein $R^{19}$ is hydrogen, unsubstituted or substituted C1–C12 alkyl or aryl, or a hydroxy protecting group;

$R^3$ is hydrogen, unsubstituted or substituted C1—C12 alkyl, or unsubstituted or substituted aryl; and n ranges from 0 to 6 to form an optionally substituted ring, wherein at least one saturated carbon atom is optionally replaced by an atom chosen from N, O, and S, and said ring is optionally fused to a second ring having 3 to 10 carbons, further wherein said second ring is a group chosen from aliphatic groups and aromatic groups, wherein at least one carbon of said second ring is optionally replaced by an atom chosen from N, O, and S.

6. A process according to claim 5, wherein the substrate is (S1)

(S1)

wherein:

$R^1$ is unsubstituted or substituted phenyl or naphthyl;

$R^2$ is unsubstituted or substituted C1–C5 wherein $R^{18}$ is unsubstituted or substituted C1–C5 alkyl, or OR$^{18}$ wherein $R^{19}$ is a hydroxy protecting group; and $R^3$ is unsubstituted C1–C5 alkyl;

and the catalyst comprises rhodium and

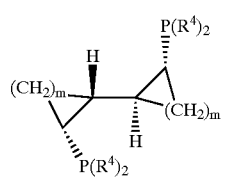

wherein:

m ranges from 3 to 4 to form an unsubstituted or substituted ring;

$R^4$ is unsubstituted or substituted phenyl.

7. A process according to claim 5, wherein the substrate is:

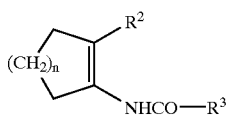

wherein:

n ranges from 1 to 3 to form an optionally substituted ring, wherein at least one saturated ring carbon atom is optionally replaced by an atom chosen from N, O, and S, and said ring is optionally fused to a second ring having 3 to 10 carbons, further wherein said second ring is a group chosen from aliphatic groups and aromatic groups, wherein the at least one carbon of said second ring is optionally replaced by an atom chosen from N, O, and S;

$R^2$ is hydrogen or unsubstituted C1–C5 alkyl; and $R^3$ is unsubstituted C1–C5 alkyl; and the catalyst comprises rhodium and

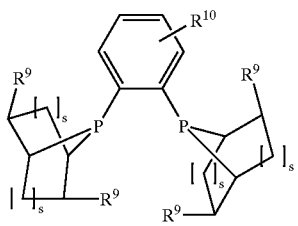

wherein:
  s ranges from 1 to 2;
  $R^9$ is unsubstituted or substituted C1–C4 alkyl; and
  $R^{10}$ is hydrogen.

8. A process according to claim 5, wherein the product formed is an aminotetralin or an aminoindan.

9. A process according to claim 1, wherein the substrate is a compound of formula (S3) to provide a compound of formula (P3):

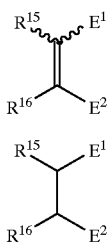

(S3)

(P3)

wherein:
  $E^1$ and $E^2$ are independently O—(C=O)—$R^{18}$, COOR$^8$, HN(C=O)RI$^8$, or O—$R^{19}$, wherein $R^{18}$ is hydrogen, or unsubstituted or substituted aryl or alkyl, and $R^{19}$ is hydrogen, unsubstituted or substituted aryl or alkyl, or a hydroxy protecting group; and
  $R^{15}$ and $R^{16}$ are independently hydrogen, or unsubstituted or substituted aryl or alkyl;
  wherein $R^{15}$ and $R^{16}$ or $R^{16}$ and $E^2$ together may form an unsubstituted or substituted ring of 3 to 10 carbons, wherein said ring may contain an atom of N, O, or S and wherein said ring may be fused to a second ring of 3 to 10 carbons, wherein said second ring may be aliphatic or aromatic and may contain an atom of N, O, or S.

10. A process according to claim 1, wherein the substrate is a β-keto ester and the catalyst comprises a compound of formula (L1),

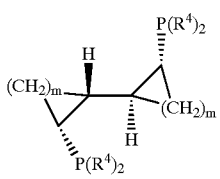

(L1)

wherein
  m ranges from 2 to 4 to form an unsubstituted ring; and
  $R^4$ is a phenyl group substituted with at least one C1–C5 alkyl group in the meta or para positions.

11. A process according to claim 1, wherein said process is a hydroformylation reaction.

12. A process according to claim 11, wherein a substrate is subjected to hydroformylation in the presence of a catalyst comprising ruthenium and a compound of formula (L2),

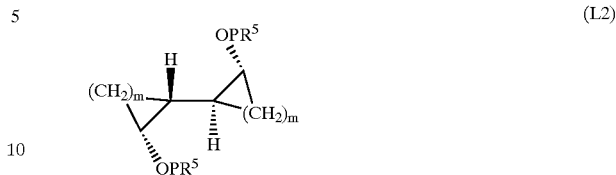

(L2)

wherein:
  m ranges from 2 to 4 to form an unsubstituted ring; and
  $R^5$ is

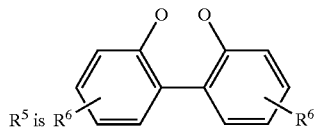

wherein each $R^6$ independently represents two substituents which are independently C1–C5 alkyl or alkoxy groups, each meta to the bond joining the phenyl rings.

13. A process according to claim 1, wherein said process is a hydrovinylation reaction.

14. A process according to claim 13, wherein a substrate is subjected to hydrovinylation in the presence of a catalyst comprising nickel and a compound of formula (L4),

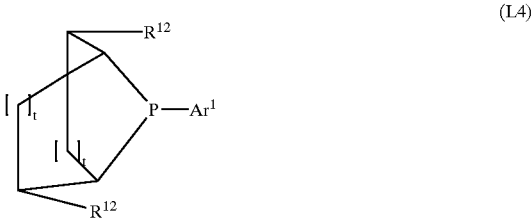

(L4)

wherein:
  t ranges from 1 to 2;
  $R^{12}$ is a C1–C5 alkyl; and
  $Ar^1$ is phenyl, unsubstituted or substituted by C1–C4 alkyl.

15. A process according to claim 15, wherein the substrate is an imine.

16. A process according to claim 15, wherein the substrate is a compound of formula (S4):

(S4)

wherein:
  $R^{21}$, $R^{22}$, $R^{23}$, and $R^{24}$ are independently hydrogen, or unsubstituted or substituted aryl or alkyl;
  wherein $R^{21}$ and $R^{22}$ together may form an unsubstituted or substituted ring of 3 to 10 carbons, wherein said ring may contain an atom of N, O, or S and wherein said ring may be fused to a second ring of 3 to 10 carbons, wherein said second ring may be aliphatic or aromatic and may contain an atom of N, O, or S, and wherein $R^{21}$ and $R^{23}$, $R^{22}$ and $R^{24}$, or $R^{23}$ and $R^{24}$ may together form an unsubstituted or substituted ring containing 3 to 10 carbons in addition to the imine nitrogen, wherein said ring may be fused to a second ring, wherein said second ring is as defined above.

17. A process according to claim 16, wherein the catalyst comprises iridium and compound of formula (L1).

UNITED STATES PATENT AND TRADEMARK OFFICE
CERTIFICATE OF CORRECTION

PATENT NO. : 6,399,787 B1
DATED : June 4, 2002
INVENTOR(S) : Xumu Zhang

It is certified that error appears in the above-identified patent and that said Letters Patent is hereby corrected as shown below:

Column 76,
Line 24, after "C1-C5" insert -- alkyl, -COOR$^{18}$ --.
Line 25, "OR$^{18}$" should read -- OR$^{19}$ --.

Column 77,
Line 35, "COOR$^8$" should read -- COOR$^{18}$ --.
Line 36, "HN(C=O)RI$^8$" should read -- HN(C=O)R$^{18}$ --.

Column 78,
Line 21, delete "R$^5$ is" before -- R$^6$ --.

Signed and Sealed this

Thirteenth Day of August, 2002

Attest:

JAMES E. ROGAN
*Attesting Officer*   *Director of the United States Patent and Trademark Office*